United States Patent
Roninson et al.

(10) Patent No.: US 11,572,369 B2
(45) Date of Patent: Feb. 7, 2023

(54) BICYCLIC PYRIDINE COMPOSITIONS AND METHODS OF USING THE SAME FOR CANCER THERAPY

(71) Applicants: UNIVERSITY OF SOUTH CAROLINA, Columbia, SC (US); SENEX BIOTECHNOLOGY, INC., Columbia, SC (US)

(72) Inventors: Igor B. Roninson, Lexington, SC (US); Mengqian Chen, Lexington, SC (US); Jing Li, West Columbia, SC (US); Jiaxin Liang, Columbia, SC (US); Li Zhang, West Columbia, SC (US); Campbell McInnes, Irmo, SC (US)

(73) Assignees: UNIVERSITY OF SOUTH CAROLINA, Columbia, SC (US); SENEX BIOTECHNOLOGY, INC., Columbia, SC (US)

( * ) Notice: Subject to any disclaimer, the term of this patent is extended or adjusted under 35 U.S.C. 154(b) by 0 days.

(21) Appl. No.: 17/427,487

(22) PCT Filed: Feb. 3, 2020

(86) PCT No.: PCT/US2020/016394
§ 371 (c)(1),
(2) Date: Jul. 30, 2021

(87) PCT Pub. No.: WO2020/160537
PCT Pub. Date: Aug. 6, 2020

(65) Prior Publication Data
US 2022/0135583 A1      May 5, 2022

Related U.S. Application Data

(60) Provisional application No. 62/800,239, filed on Feb. 1, 2019.

(51) Int. Cl.
*C07D 495/02* (2006.01)
*A61P 35/02* (2006.01)
*A61P 35/04* (2006.01)

(52) U.S. Cl.
CPC ............ *C07D 495/02* (2013.01); *A61P 35/02* (2018.01); *A61P 35/04* (2018.01)

(58) Field of Classification Search
None
See application file for complete search history.

(56) References Cited

U.S. PATENT DOCUMENTS

| 4,271,723 | A | 6/1981 | Shaffer |
| 5,811,436 | A | 9/1998 | Leonard |
| 6,964,956 | B2 | 11/2005 | Cywin |
| 7,405,225 | B2 | 7/2008 | Cywin |
| 8,598,344 | B2 | 12/2013 | Porter |
| 9,321,737 | B2 | 4/2016 | Roninson |
| 9,636,342 | B2 | 5/2017 | Chen |
| 9,789,107 | B2 | 10/2017 | Homman |
| 9,937,153 | B2 | 4/2018 | Cooper |
| 11,014,906 | B2 | 5/2021 | Roninson |
| 2007/0207201 | A1 | 9/2007 | Krishnan |
| 2007/0219234 | A1 | 9/2007 | Oizumi |
| 2014/0309224 | A1 | 10/2014 | Porter |
| 2016/0000787 | A1 | 1/2016 | Broude |
| 2018/0319814 | A1 | 11/2018 | Shair |

FOREIGN PATENT DOCUMENTS

| WO | 2003103661 A1 | 12/2003 |
| WO | 2014194201 A2 | 12/2014 |
| WO | 2016018511 A2 | 2/2016 |
| WO | 2016100782 A1 | 6/2016 |
| WO | 2017076968 A1 | 5/2017 |

OTHER PUBLICATIONS

Amirhosseini, M., et al. "Cyclin-dependent kinase 8/19 inhibition suppresses osteoclastogenesis by downregulating RANK and promotes osteoblast mineralization and cancellous bone healing." Journal of cellular physiology 234.9 (2019): 16503-16516.
Chen, J., et al. "Small molecule screens identify CDK8-inhibitors as candidate Diamond-Blackfan anemia drugs." Blood 132 (2018): 753.
Cheong, J. K., et al. "Casein kinase 1a-dependent feedback loop controls autophagy in RAS-driven cancers." The Journal of clinical investigation 125.4 (2015): 1401-1418.
Ellis, L., et al. "Development of a castrate resistant transplant tumor model of prostate cancer." The Prostate 72.6 (2012): 587-591.
Fabian, M.A. et al. A small molecule-kinase interaction map for clinical kinase inhibitors. Nat. Biotechnol. 23, 329-336 (2005).
Hall, D. D., et al. "Ectopic expression of Cdk8 induces eccentric hypertrophy and heart failure." JCI insight 2.15 (2017).017, 2.
Han, X., et al. "Discovery of potent and selective CDK8 inhibitors through FBDD approach." Bioorganic & medicinal chemistry letters 27.18 (2017): 4488-4492.
Hatcher, J. M., et al. "Development of highly potent and selective steroidal inhibitors and degraders of CDK8." ACS medicinal chemistry letters 9.6 (2018): 540-545.
International Searching Authority. International Search Report and Written Opinion for application PCT/US2020/016394, dated May 22, 2020. 15 pages.
International Searching Authority. International Search Report and Written Opinion for application PCT/US2020/033937, dated Aug. 14, 2020. 15 pages.
Johannessen, L., et al. "Small-molecule studies identify CDK8 as a regulator of IL-10 in myeloid cells." Nature chemical biology 13.10 (2017): 1102-1108.

(Continued)

*Primary Examiner* — Brian J Davis
(74) *Attorney, Agent, or Firm* — Quarles & Brady LLP

(57) ABSTRACT

Disclosed herein are bicyclic pyridines, such as thienopyridine, pyrrolopyridine, furopyridine compounds, and methods for treating cancers.

20 Claims, 27 Drawing Sheets

(56) References Cited

OTHER PUBLICATIONS

Kapoor, A., et al. "The histone variant macroH2A suppresses melanoma progression through regulation of CDK8." Nature 468. 7327 (2010): 1105-1109.

Kim, S. Y., et al. "CK1e is required for breast cancers dependent on B-catenin activity." PloS one 5.2 (2010): e8979.

Li et al., Characterizing CDK8/19 Inhibitors through a NF?B-Dependent Cell-Based Assay, Cells 2019, 8(10), 1208.

Liang, J., et al. "CDK8 selectively promotes the growth of colon cancer metastases in the liver by regulating gene expression of TIMP3 and matrix metalloproteinases." Cancer research 78.23 (2018): 6594-6606.

Manni, S. et al. "Role of protein kinases CK1a and CK2 in multiple myeloma: regulation of pivotal survival and stress-managing pathways." Journal of hematology & oncology 10.1 (2017): 1-10.

McDermott, MSJ, et al. "Inhibition of CDK8 mediator kinase suppresses estrogen dependent transcription and the growth of estrogen receptor positive breast cancer" Oncotarget 8.8 (2017): 12558.

Mohamed, A. A., et al. "Identification of a small molecule that selectively inhibits ERG-positive cancer cell growth." Cancer research 78.13 (2018): 3659-3671.

Nakamura, A., et al. "CDK8/19 inhibition induces premature G1/S transition and ATR-dependent cell death in prostate cancer cells." Oncotarget 9.17 (2018): 13474.

Olson, B. M., et al. "Prostate cancer cells express more androgen receptor (AR) following androgen deprivation, mproving recognition by AR-specific T cells." Cancer immunology research 5.12 (2017): 1074-1085.

Pelish, H. E., et al. "Mediator kinase inhibition further activates super-enhancer-associated genes in AML." Nature 526.7572 (2015): 273-276.

Philip, S., et al. "Cyclin-dependent kinase 8: a new hope in targeted cancer therapy? Miniperspective." Journal of medicinal chemistry 61.12 (2017): 5073-5092.

Porter, D. C., et al. "Cyclin-dependent kinase 8 mediates chemotherapy-induced tumor-promoting paracrine activities." Proceedings of the National Academy of Sciences 109.34 (2012): 13799-13804.

Richter, J., et al. "CK1a overexpression correlates with poor survival in colorectal cancer." BMC cancer 18.1 (2018): 1-11.

Saito, K., et al. "Discovery and structure-activity relationship of thienopyridine derivatives as bone anabolic agents." Bioorganic & medicinal chemistry 21.7 (2013): 1628-1642.

Saito, K., et al. "Synthesis and structure-activity relationship of 4-alkoxy-thieno [2, 3-b] pyridine derivatives as potent alkaline phosphatase enhancers for osteoporosis treatment." Bioorganic & medicinal chemistry letters 29.14 (2019): 1769-1773.

Toyoshima, M., et al. "Functional genomics identifies therapeutic targets for MYC-driven cancer." Proceedings of the National Academy of Sciences 109.24 (2012): 9545-9550.

Varghese, R. T., et al. "Casein Kinase 1 Epsilon Regulates Glioblastoma Cell Survival." Scientific Reports 8 (2018).

Watson, P. A., et al. "Context-dependent hormone-refractory progression revealed through characterization of a novel murine prostate cancer cell line." Cancer research 65.24 (2005): 11565-11571.

Xu, W., et al. "Mutated K-ras activates CDK8 to stimulate the epithelial-to-mesenchymal transition in pancreatic cancer in part via the Wnt/-catenin signaling pathway." Cancer letters 356.2 (2015): 613-627.

Yang, WS, et al. "Inhibition of casein kinase 1-epsilon induces cancer-cell-selective, PERIOD2-dependent growth arrest." Genome Biology 9.6 (2008): R92.

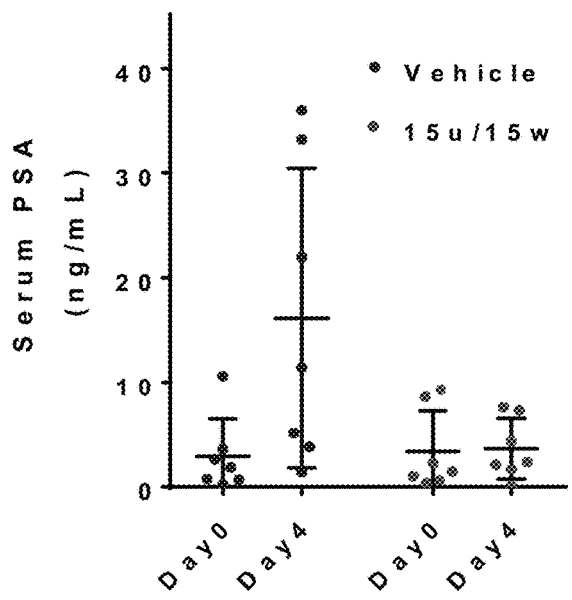
Figure 6D
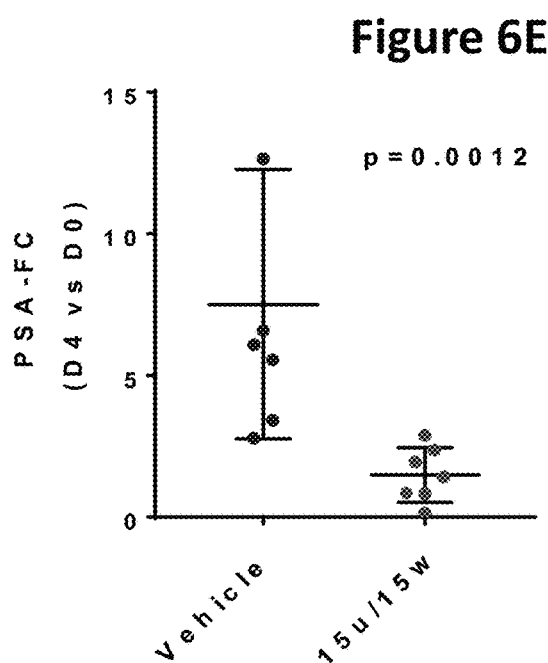
Figure 6E
Figure 6F
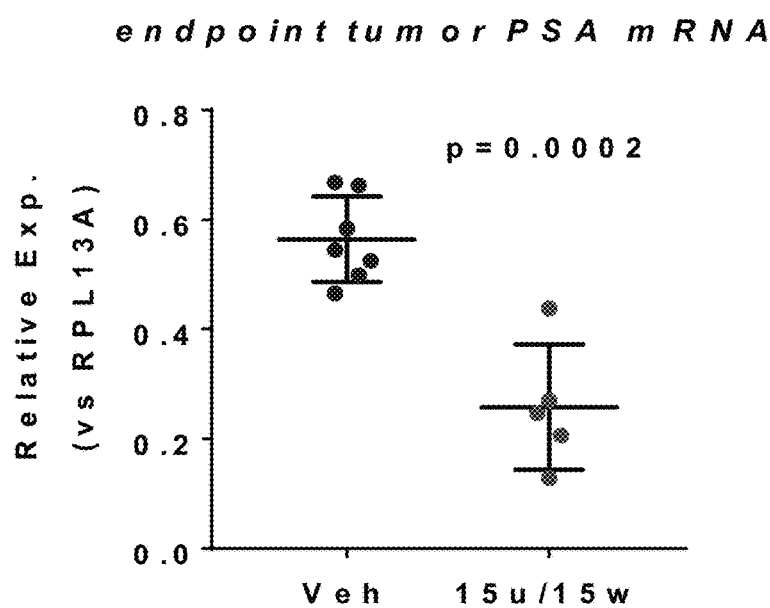

Figure 7A
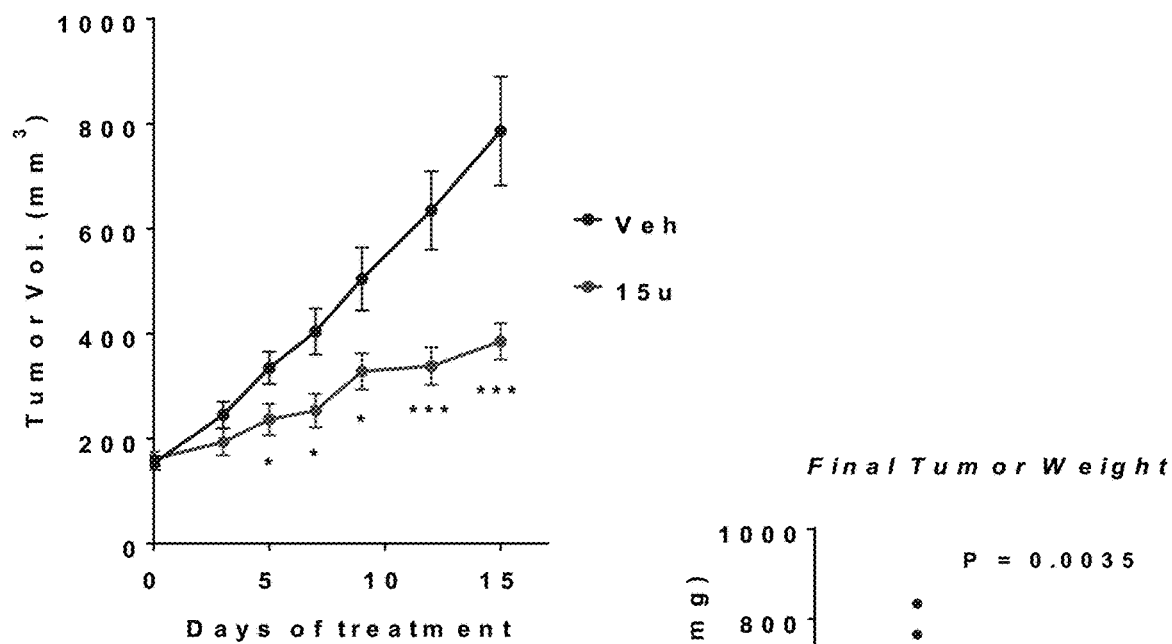
Figure 7B
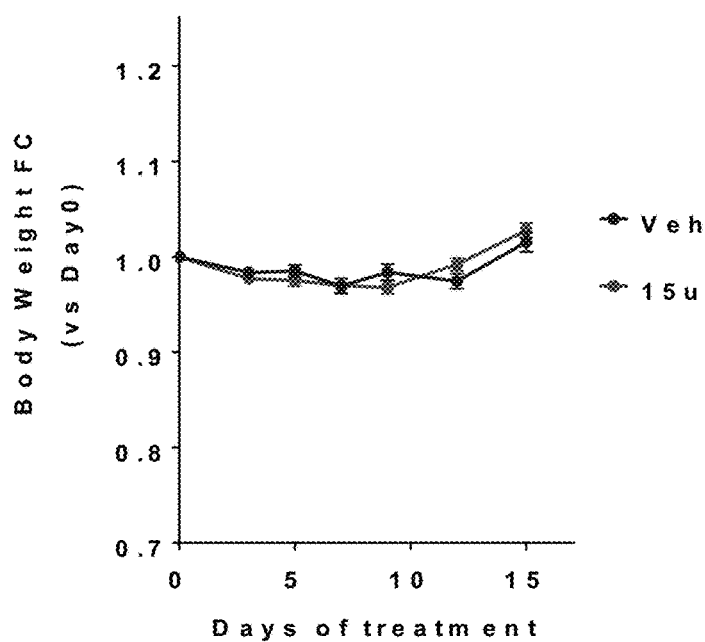
Figure 7C

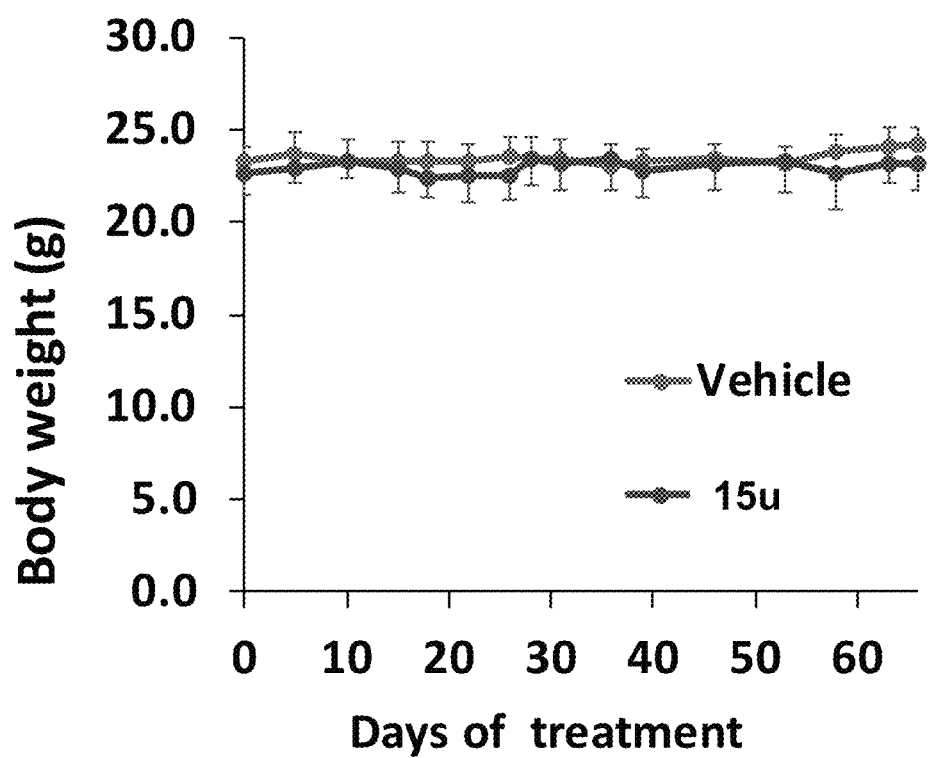

BICYCLIC PYRIDINE COMPOSITIONS AND METHODS OF USING THE SAME FOR CANCER THERAPY

CROSS-REFERENCE TO RELATED APPLICATIONS

This patent application is a national stage filing under 35 U.S.C. § 371 of International Patent Application No. PCT/US2020/016394, filed Feb. 3, 2020, which claims benefit of priority to U.S. Provisional Application Ser. No. 62/800,239, filed Feb. 1, 2019, the contents of each are incorporated herein by reference in their entireties.

BACKGROUND

CDK8 and CDK19, two closely related transcription-regulating kinases, have become a burgeoning novel cancer drug target (Philip, S. et al., *J Med Chem* 2018, 61, 5073-5092). In particular, CDK8/19 inhibitors were shown to be efficacious in castration-refractory prostate cancer (CRPC) (Chen, Roninson, U.S. Pat. No. 9,636,342), in acute myeloid leukemia (Pelish et al., Nature. 2015 Oct. 8; 526(7572):273-276), in hepatic metastases of colon cancer (Liang et al., Cancer Res. 2018 Dec. 1; 78(23):6594-6606), in estrogen receptor-positive breast cancer when combined with anti-estrogens (McDermott et al., Oncotarget. 2017 Feb. 21; 8(8):12558-12575), and in HER2-positive breast cancer when combined with HER2-targeting agents (McDermott et al., International Patent Pub. No. WO 2016/018511). Furthermore, CDK8/19 inhibitors prevent the induction of genes that promote metastasis and drug resistance in cancer cells of different tumor types, treated with conventional DNA-damaging chemotherapeutic agents or radiation (Porter, D. C., et al., *Proc Natl Acad Sci USA* 2012, 109, 13799-804). In vivo administration of a CDK8/19 inhibitor also improved the effect of a chemotherapeutic drug doxorubicin in a lung cancer model (Porter et al., ibid.), indicating the utility of CDK8/19 inhibitors for the treatment of different cancers when combined with a variety of DNA-damaging agents.

Aside from cancer, CDK8/19 inhibitors show promise in inflammation-associated diseases (US Patent Pub. No. 2014/0309224 to Porter, D. C.; Johnannessen, L., et al., *Nat Chem Biol* 2017, 13, 1102-1108); cardiovascular diseases (Hall, D., et al., *JCI Insight* 2017, 2; International Patent Pub. No. WO 2016/100782 to Roninson, I. B.); ribosomopathies; conditions characterized by reduced number of hematopoietic stem cells and/or progenitor cells; and bone anabolic disorders (International Patent Pub. No. WO 2017/076968 to Flygare, J.).

A number of CDK8/19 inhibitors have been reported (Philip et al., J Med Chem. 2018 Jun. 28; 61(12):5073-5092. doi: 10.1021/acs.jmedchem.7b00901). These include certain quinazoline-based compounds developed by some of the instant inventors that are highly selective for CDK8/19, such as SNX2-1-53 (a.k.a. Senexin A) (Porter, D. C., et al., *Proc Natl Acad Sci USA* 2012, 109, 13799-804; U.S. Pat. No. 8,598,344 to Porter, D. C.) and SNX2-1-165 (a.k.a. Senexin B) (U.S. Pat. No. 9,321,737 to Roninson, I. B.), as well as highly CDK8/19-selective quinoline-based compounds [U.S. Patent Appl. Nos. 62/720,774 and 62/720,776]. Other CDK8/19 inhibitors have been reported recently (Hatcher, J. M. et al., ACS Med Chem Lett 2018, 9, 540-545; Nakamura, A. et al., Oncotarget 2018, 9, 13474-13487; Han, X., et al., Bioorg Med Chem Lett 2017, 27, 4488-4492).

Thienopyridines are a class of compounds having a bicyclic aromatic ring. Various thienopyridines have been disclosed, including in U.S. Pat. No. 6,964,956, U.S. Patent Pub. 2007/0219234, International Patent Pub. WO 2017/076968, Saito, K. et al., *Bioorg Med Chem* 2013, 21, 1628-42, and Saito et al., *Bioorg Med Chem Lett* 2019, 29, 1769-73. U.S. Pat. No. 6,964,956 discloses several thienopyridines inhibit the IKB kinase (IKK) complex. Saito and U.S. Patent Pub. 2007/021923 disclosed several thienopyridines having potential bone anabolic activity. Compound 15w was shown to have the highest bone anabolic activity in a cell-based assay (Saito, 2013). Kinome profiling also showed 15w (or DBA-7) and 15k (or DBA-6) to be selective inhibitors of CDK8 and CDK19 (WO 2017/076968). Despite 15w showing high bone anabolic activity in vitro, 15w had poor pharmacokinetics (PK) with low $C_{max}$ (Saito, 2013).

None of the CDK8/19 inhibitors have yet demonstrated clinical efficacy, which is determined not only by the ability of a compound to inhibit CDK8/19 but also by its off-target activities, which can be either beneficial for therapy or may cause adverse effects, as well as by the pharmacokinetics (PK) of the compound.

BRIEF SUMMARY OF THE INVENTION

Disclosed herein are bicyclic pyridine compounds for use in the treatment of cancer. The bicyclic pyridine compounds comprise a compound of Formula 1

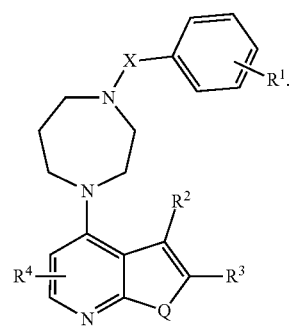

(Formula 1)

Q may be selected from sulfur, —NH—, or oxygen. X may be selected from —$(CH_2)_n$— and n is selected from 0, 1, or 2. $R^4$ may be hydrogen or a saturated or unsaturated, branched or unbranched, substituted or unsubstituted $C_1$-$C_6$ alkyl. $R^3$ may be selected from hydrogen, cyano, a halo, a substituted or unsubstituted amino, a substituted or unsubstituted amido; or a substituted or unsubstituted sulfonamido. $R^2$ may be selected from hydrogen, cyano, a halo, a substituted or unsubstituted amino, a substituted or unsubstituted amido; or a substituted or unsubstituted sulfonamido. $R^1$ may be selected from hydrogen; a cyano; a deuterated or undeuterated hydroxyl, a deuterated or undeuterated carboxy, a halo, a substituted or unsubstituted, deuterated or undeuterated amino; a substituted or unsubstituted, deuterated or undeuterated amido; a substituted or unsubstituted, deuterated or undeuterated sulfonamide, a saturated or unsaturated, branched or unbranched, substituted or unsubstituted, deuterated or undeuterated $C_1$-$C_6$ alkyl; a saturated or unsaturated, branched or unbranched, substituted or unsubstituted, deuterated or undeuterated $C_1$-$C_6$ alkoxyl. In some embodiments, when Q is sulfur, n is 0, $R^4$ is hydrogen, $R^3$ is —C(O)NH$_2$, and $R^2$ is —NH$_2$, $R^1$ is selected from a deuterated hydroxyl, a deuterated carboxy, a substituted or unsubstituted, deuterated amino; a substituted or unsubstituted, deuterated amido; a substituted or unsubstituted, deuterated or undeuterated sulfonamide, a saturated or unsaturated, branched or unbranched, substituted or unsubstituted, deuterated $C_1$-$C_6$ alkyl; a saturated or unsaturated, branched or unbranched, substituted or unsubstituted, deuterated $C_1$-$C_6$ alkoxyl. In some embodiments, when at least one of Q is not sulfur, n is not 0, $R^4$ is not hydrogen, $R^3$ is not —C(O)NH$_2$, and $R^2$ is not —NH$_2$, $R^1$ is selected from a cyano; a deuterated or undeuterated hydroxyl, a deuterated or undeuterated carboxy, a halo, a substituted or unsubstituted, deuterated or undeuterated amino; a substituted or unsubstituted, deuterated or undeuterated amido; a substituted or unsubstituted, deuterated or undeuterated sulfonamide, a saturated or unsaturated, branched or unbranched, substituted or unsubstituted, deuterated or undeuterated $C_1$-$C_6$ alkyl; a saturated or unsaturated, branched or unbranched, substituted or unsubstituted, deuterated or undeuterated $C_1$-$C_6$ alkoxyl. In particular embodiments, the compound has the formula

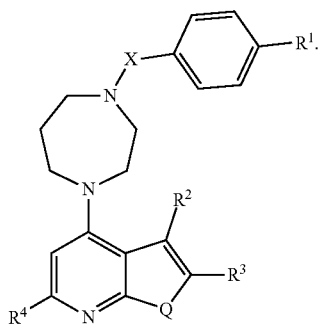

In some embodiments, $R^1$ is

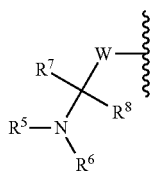

W may be selected from —(CH$_2$)$_m$— or —(CD$_2$)$_m$— and m may be selected from 0, 1, or 2. $R^5$ and $R^6$ may be independently selected from hydrogen, deuterium, a deuterated or undeuterated, saturated or unsaturated, branched or unbranched, substituted or unsubstituted $C_1$-$C_6$ alkyl. $R^7$ and $R^8$ may be hydrogen, $R^7$ and $R^8$ may be deuterium, or $R^7$ and $R^8$ together may be oxo. In particular embodiments, when Q is sulfur, n is 0, $R^4$ is hydrogen, $R^3$ is —C(O)NH$_2$, and $R^2$ is —NH$_2$, $R^1$ comprises at least one deuterium.

In some embodiments, $R^1$ is

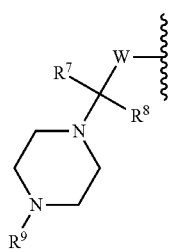

W may be selected from —(CH$_2$)$_m$— or —(CD$_2$)$_m$— and m may be selected from 0, 1, or 2. $R^9$ may be selected from hydrogen, deuterium, or a deuterated or undeuterated, saturated or unsaturated, branched or unbranched, substituted or unsubstituted $C_1$-$C_6$ alkyl. $R^7$ and $R^8$ may be hydrogen, $R^7$ and $R^8$ may be deuterium, or $R^7$ and $R^8$ together may be oxo. In some embodiments, the $C_4N_2$ heterocycle is deuterated.

Another aspect of the invention is a method for treatment of a subject having a cancer. The method may comprise administering a therapeutically effective amount of any of the compositions described herein. In some embodiments, the cancer is a prostate cancer, a leukemia, a breast cancer, colon cancer, ovarian cancer, pancreatic cancer, or melanoma. In particular embodiments, the cancer is a prostate cancer, such as a castration refractory prostate cancer or a prostate cancer resistant to an androgen deprivation therapy. In other embodiments, the cancer is a leukemia, such as acute myeloid leukemia. In yet other embodiments, the cancer is a breast cancer such as a metastatic breast cancer or a triple negative breast cancer.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIGS. 6D-6F shows the effect of a mixture of 15u and 15w on PSA serum protein fold-change (FIG. 6D) and tumor-sample PSA mRNA expression (FIG. 6E and FIG. 6F) in male NSG mice bearing C4-2 xenografts after 4 days treatment at 30 mg/kg q.d. of each compound.

FIG. 7A shows the effect of 15u on xenograft tumor growth of CRPC cell line 22rv1 (P-value style: (*) 0.05-0.01; () 0.01-0.001; (*)<0.001).

FIG. 7B shows the weight of tumors at the end of the same study.

FIG. 7C shows body weight changes of control and 15u-treated mice in the same study.

FIG. 10B shows in vivo bioluminescence images of treated mice. FIG. 10C shows a line graph of bioluminescent signal as total flux in photons per second (p/s). FIG. 10D shows a survival curve of treated mice.

FIGS. 11A-11C demonstrate the effect of 15u on in vivo growth of MDA-MB-468 triple-negative breast cancer (TNBC) xenografts. FIG. 11A is a graph showing the dynamics of tumor volumes in control and 15u-treated mice. ***: p<0.02. FIG. 11B is a bar graph showing the final tumor weights after treatment. FIG. 11C is a graph showing the dynamics of mouse body weights.

FIG. 12A shows the dynamics of body weight in male and female CD-1 mice treated with 15u in solution formulation by gavage twice daily (b.i.d.) at different doses for 2 weeks. FIG. 12B show the dynamics of body weight in male and female CD-1 mice treated with 15u via medicated diet at different dose strengths for 4-5 weeks.

FIG. 14A shows a UV chromatograph of 15u_D6. FIG. 14B shows an ES+TIC chromatograph of 15u_D6. FIG. 14C shows the parent ion of 15u_D6 as a further confirmation of the synthesis of the compounds.

DETAILED DESCRIPTION OF THE INVENTION

Figure 1A:
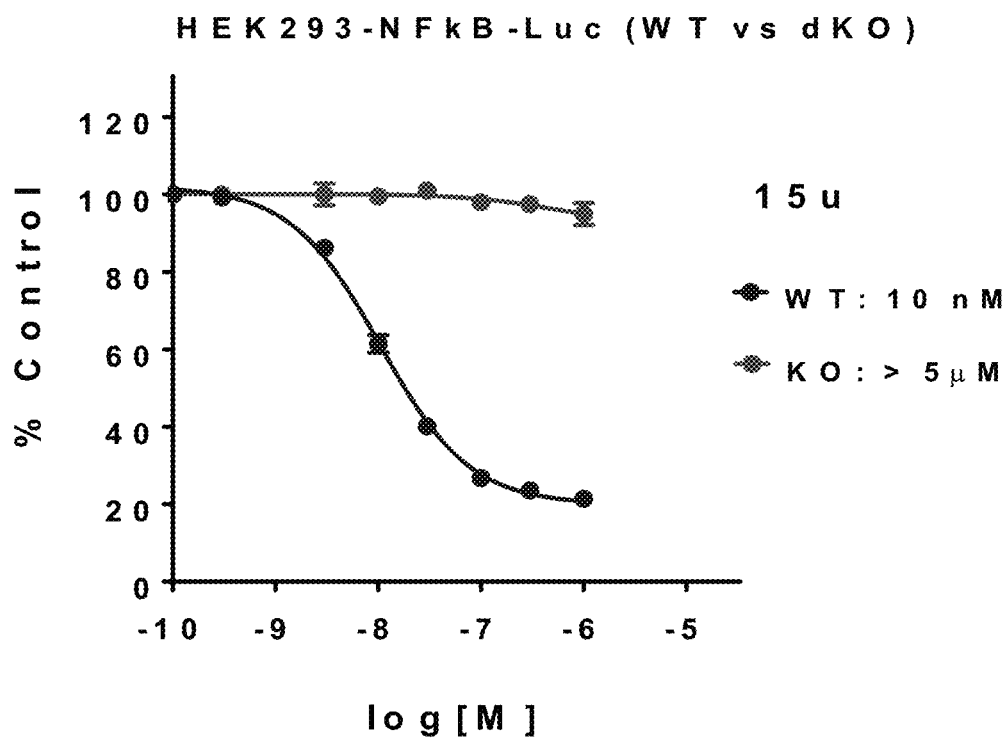
FIGS. 1A and 1B show the effects of different concentrations of 15u (FIG. 1A) and 15w (FIG. 1B) in the NFκB reporter assay in parental and CDK8/19 double-knockout reporter cells.

Disclosed herein are bicyclic pyridines, such as thienopyridine, pyrrolopyridine, furopyridine compounds, and methods for treating cancers. The compositions may selectively inhibit kinases CDK8 and CDK19 and, in some cases, RIOK2, CSNK1A1, and CSNK1E as well. The inhibition of each of these kinases are beneficial for the treatment of conditions such as cancer.

The Examples that follow demonstrate the suitability of these compounds for the preparation of pharmaceutical compositions based on pharmacokinetics and for treatment of subjects suffering from cancer. Intravenous and oral administration of the compounds disclosed herein results in high AUC and very slow clearance, making them suitable for the preparation of pharmaceutical compositions and for use in the treatment of cancers. 15u, deuterated compounds 15u_D6 and 15w_D6, and compound 6304 demonstrate surprisingly good PK. 15u has a high AUC and very slow clearance, as the average serum concentration of 15u at a late time point (8 hrs) was 64.4% of $C_{max}$ (Example 3). The deuterated analogue 15u_D6 also had a high AUC, which is comparable to or better than 15u (Examples 4 and 12). 15w_D6 not only had greater inhibitory power than its nondeuterated counterpart, 15w, but it also had a superior AUC (Examples 4 and 12). The compounds disclosed herein also specifically inhibit kinases CDK8 and CDK19. For example, compounds 15u and 15u_D6 demonstrated high specificity for these kinase targets (Example 3).

The compounds disclosed herein demonstrate the ability to treat or inhibit the progression of various cancers. For example, the compounds disclosed herein have shown in vivo efficacy against prostate cancer, breast cancer, and leukemia (Examples 5 and -9).

Because the compounds disclosed herein possess favorable PK, in vivo activity against several different cancers, together with favorable kinome profiles, the compounds are effective CDK8/19 inhibitors for the treatment of cancers linked to CDK8/19 activity.

Bicyclic Pyridine Compounds

Disclosed herein are bicyclic pyridine compounds such as thienopyridine, pyrrolopyridine, and furopyridine compounds. The compounds comprise a compound of Formula 1

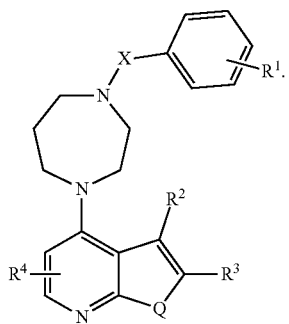

In some embodiments, the compound is a compound of formula

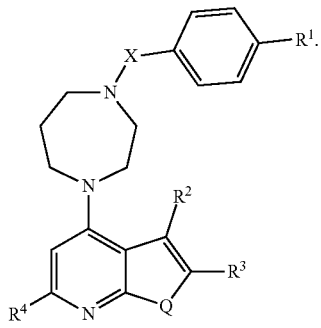

Q may be selected from sulfur, resulting in a thienopyridine, an —NH—, resulting in a pyrrolopyridine, or oxygen, resulting in the furopyridine. In some embodiments, Q is sulfur.

X comprises —(CH$_2$)$_n$— where n is selected from 0, 1, or 2. Suitably X is methylene (i.e., n=1), ethylene (i.e., n=2), or a covalent bond (i.e., n=0) between the seven-membered ring and the R$^1$ substituted aryl. In some embodiments, n is 0.

R$^4$ is hydrogen or a saturated or unsaturated, branched or unbranched, substituted or unsubstituted C$_1$-C$_6$ alkyl. Suitably, R$^4$ may be hydrogen or a methyl.

R$_3$ may be selected from hydrogen, cyano, a halo, a substituted or unsubstituted amino, a substituted, or unsubstituted amido or a substituted or unsubstituted sulfonamido. Suitably R$^3$ may be selected from a substituted or unsubstituted amido such as —C(O)NH$_2$.

R$_2$ may be selected from hydrogen, cyano, a halo, a substituted or unsubstituted amino, a substituted or unsubstituted amido, or a substituted or unsubstituted sulfonamido. Suitably, R$^2$ may be selected from a substituted or unsubstituted amino such as —NH$_2$.

R$^1$ may be selected from hydrogen; a cyano; a deuterated or undeuterated hydroxyl, a deuterated or undeuterated carboxy, a halo, a substituted or unsubstituted, deuterated or undeuterated amino; a substituted or unsubstituted, deuterated or undeuterated amido; a substituted or unsubstituted, deuterated or undeuterated sulfonamide, a saturated or unsaturated, branched or unbranched, substituted or unsubstituted, deuterated or undeuterated C$_1$-C$_6$ alkyl; a saturated or unsaturated, branched or unbranched, substituted or unsubstituted, deuterated or undeuterated C$_1$-C$_6$ alkoxyl.

Exemplary compounds include, without limitation, compounds disclosed in TABLE 6.

In some embodiments, when Q is sulfur, n is 0, R$^4$ is hydrogen, R$^3$ is —C(O)NH$_2$, and R$^2$ is —NH$_2$, R$^1$ is selected from a deuterated hydroxyl, a deuterated carboxy, a substituted or unsubstituted, deuterated amino; a substituted or unsubstituted, deuterated amido; a substituted or unsubstituted, deuterated or undeuterated sulfonamide, a saturated or unsaturated, branched or unbranched, substituted or unsubstituted, deuterated C$_1$-C$_6$ alkyl; a saturated or unsaturated, branched or unbranched, deuterated C$_1$-C$_6$ alkoxyl.

In some embodiments, when at least one of Q is not sulfur, n is not 0, R$^4$ is not hydrogen, R$^3$ is not —C(O)NH$_2$, and R$^2$ is not —NH$_2$, R$^1$ is selected from a cyano; a deuterated or undeuterated hydroxyl, a deuterated or undeuterated carboxy, a halo, a substituted or unsubstituted, deuterated or undeuterated amino; a substituted or unsubstituted, deuterated or undeuterated amido; a substituted or unsubstituted, deuterated or undeuterated sulfonamide, a saturated or unsaturated, branched or unbranched, substituted or unsubstituted, deuterated or undeuterated C$_1$-C$_6$ alkyl; a saturated or unsaturated, branched or unbranched, substituted or unsubstituted, deuterated or undeuterated C$_1$-C$_6$ alkoxyl.

In some embodiments, R$^1$ is

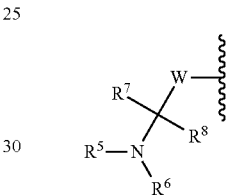

W may be selected from —(CH$_2$)$_m$— or —(CD$_2$)$_m$— and m may be selected from 0, 1, or 2. R$^5$ and R$^6$ may be independently selected from hydrogen, deuterium, a deuterated or undeuterated, saturated or unsaturated, branched or unbranched, substituted or unsubstituted C$_1$-C$_6$ alkyl. R$^7$ and R$^8$ may be hydrogen, R$^7$ and R$^8$ may be deuterium, or R$^7$ and R$^8$ together may be oxo. In particular embodiments, when Q is sulfur, n is 0, R$^4$ is hydrogen, R$^3$ is —C(O)NH$_2$, and R$^2$ is —NH$_2$, R$^1$ comprises at least one deuterium.

In some embodiments, W is selected from —(CH$_2$)$_m$— or —(CD$_2$)$_m$— and m is 0.

In some embodiments, W is selected from —(CH$_2$)$_m$— and m is 1. In other embodiments, W is selected from —(CD$_2$)$_m$— and m is 1.

In some embodiments, R$^7$ and R$^8$ together are an oxo. In some embodiments, R$^7$ and R$^8$ are each hydrogen.

In some embodiments, R$^5$ and R$^6$ are each methyl. In other embodiments, are each methyl-d3.

In some embodiments, one of R$^5$ and R$^6$ is hydrogen and the other methyl. In other embodiments, one of R$^5$ and R$^6$ is deuterium and the other methyl-d3.

In some embodiments, at least one of R$^5$ or R$^6$ is a deuterated or undeuterated, saturated or unsaturated, branched or unbranched, substituted or unsubstituted C$_1$-C$_6$ alkyl. Exemplary substitutions include without limitation, hydroxyl substitutions, amino substitutions, or carbamate substitutions.

Exemplary R$^1$ include, without limitation, N,N-bis(methyl-d3)formamide, N,N-bis(methyl-d3)acetamide, N,N-dimethylacetamide-2,2-d2, N,N-dimethylformamide, N,N-dimethylacetamide, N-methylformamide, N-(3-hydroxypropyl)formamide, N-(3-aminopropyl)-N-methylformamide, or tert-butyl (3-(N-methylformamido)propyl)carbamate.

In some embodiments, $R^1$ is

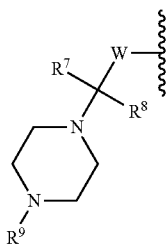

W may be selected from —(CH$_2$)$_m$— or —(CD$_2$)$_m$— and m may be selected from 0, 1, or 2. $R^9$ may be selected from hydrogen, deuterium, or a deuterated or undeuterated, saturated or unsaturated, branched or unbranched, substituted or unsubstituted $C_1$-$C_6$ alkyl. $R^7$ and $R^8$ may be hydrogen, $R^7$ and $R^8$ may be deuterium, or $R^7$ and $R^8$ together may be oxo. In some embodiments, the $C_4N_2$ heterocycle is deuterated.

In some embodiments, W is selected from —(CH$_2$)$_m$— or —(CD$_2$)$_m$— and m is 0.

In some embodiments, W is selected from —(CH$_2$)$_m$— and m is 1. In other embodiments, W is selected from —(CD$_2$)$_m$— and m is 1.

In some embodiments, $R^7$ and $R^8$ together are an oxo. In other embodiments, $R^7$ and $R^8$ are each hydrogen.

In some embodiments, $R^9$ is hydrogen, methyl, or C(O)OC(CH$_3$).

Exemplary $R^1$ include, without limitation, (4-methylpiperazin-1-yl)methylene, 4-methylpiperazine-1-carbaldehyde, piperazine-1-carbaldehyde, or tert-butyl 4-formylpiperazine-1-carboxylate.

As demonstrated in the examples that follow, some of the bicyclic pyridine compounds have surprisingly good PK. For example, thienopyridines 15u, 15u_D6, 15w_D6, and 604 demonstrate suitable PK characteristics for the preparation of pharmaceutical compositions and for use in the treatment of cancers. As demonstrated in the Examples, intravenous and oral administration of these compounds results in high $C_0$ and $C_{max}$ concentrations, slow elimination, and large AUCs in in vivo mouse models.

Definitions

As used herein, an asterisk "*" or a plus sign "+" may be used to designate the point of attachment for any radical group or a substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group. An exemplary alkylene group is —CH$_2$CH$_2$—.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like The term "heteroalkyl" as used herein refers to an "alkyl" group in which at least one carbon atom has been replaced with a heteroatom (e.g., an O, N, or S atom). Suitably, the heteroalkyl group may be an "alkoxyl" group, an "amino" group, or a "sulfanyl".

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of an cycloalkyl group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number of ring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines, wherein substituents may include, for example, alkyl, cycloalkyl, heterocyclyl, alkenyl, and aryl. Suitably, the amino may be unsubstituted (i.e., —$NH_2$) or a substituted amino of formula —NHR or —NRR' wherein R and R' are independently selected from a C1-C12 alkyl or a C1-C6 alkyl such as methyl or ethyl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

An "epoxide" is a cyclic ether with a three-atom ring typically include two carbon atoms and whose shape approximates an isosceles triangle. Epoxides can be formed by oxidation of a double bound where the carbon atoms of the double bond form an epoxide with an oxygen atom. The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl. Suitably, the carboxamido may comprise —C(O)NRR' wherein R and R' are independently selected from a C1-C12 alkyl or a C1-C6 alkyl such as methyl or ethyl.

The term "carboxy" as used herein refers to the radical —COOH or its corresponding salts, e.g. —COONa, etc.

The term "amide" or "amido" as used herein refers to a radical of the form —$R^1C(O)N(R^2)$—, —$R^1C(O)N(R^2)R^3$—, —$C(O)N R^2R^3$, or —$C(O)NH_2$, wherein $R^1$, $R^2$ and $R^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro. Suitably, the amido may comprise —$C(O)NR^2R^3$ wherein $R^2$ and $R^3$ are independently selected from hydrogen or a C1-C12 alkyl or a C1-C6 alkyl. Suitably $R^2$ and $R^3$ may be independently selected from hydrogen, methyl, or ethyl.

The term "sulonamido" as used herein refers to a radical of the form —$R^1C(S)_2N(R^2)$—, —$R^1C(S)_2N(R^2) R^3$—, —$C(S)_2N R^2R^3$, or —$C(S)_2NH_2$, wherein $R^1$, $R^2$ and $R^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro. Suitably, the sulfonamido may comprise —$C(S)_2NR^2R^3$ wherein $R^2$ and $R^3$ are independently selected from hydrogen or a C1-C12 alkyl or a C1-C6 alkyl. Suitably $R^2$ and $R^3$ may be independently selected from hydrogen, methyl, or ethyl.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereo isomers of these compounds and mixtures thereof.

Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Compositions comprising substantially purified stereoisomers, epimers, or enantiomers, or analogs or derivatives thereof are contemplated herein (e.g., a composition comprising at least about 90%, 95%, or 99% pure stereoisomer, epimer, or enantiomer.)

Pharmaceutical Compositions

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action is about 1 nM to 100 µM.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (Pro-Solv SMCC™) Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acesulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride. Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurized aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form that is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods disclosed herein may be administered as a single compound or a combination of compounds. For example, a compound that treats cancer activity may be administered as a single compound or in combination with another compound that treats cancer or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds that are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

Methods of Treatment

The compositions described are useful for treating a subject. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein, a "subject" may be interchangeable with "patient" or "individual" and means an animal, which may be a human or non-human animal, in need of treatment. A "subject in need of treatment" may include a subject having a disease, disorder, or condition that is responsive to therapy with the pyridine compounds disclosed herein. For example, a "subject in need of treatment" may include a subject having a CDK8/19-associated disease, disorder, or condition such as cancer, inflammation-associated diseases, cardiovascular diseases, ribosomopathies, conditions characterized by reduced number of hematopoietic stem cells and/or progenitor cells, and bone anabolic disorders. A CDK8/19-associated disease, disorder, or condition includes any disease, disorder, or condition for which the subject may be treated by the inhibition of CDK8 or CDK19.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a CDK8/19-associated disease.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

In some embodiments, the CDK8/19-associated disease is a prostate cancer, suitably a castration refractory prostate cancer or a prostate cancer resistant to an androgen deprivation therapy. As used herein, "castration refractory prostate cancer" or "castrate-resistant prostate cancer" or "CRPC" is a prostate cancer that keeps growing even when the amount of testosterone in the body is reduced to very low levels. Many early-stage prostate cancers need substantially normal levels of testosterone to grow, whereas CRPC does not.

Androgen deprivation therapy (or androgen suppression therapy) is a prostate cancer hormone therapy. Androgen deprivation therapy may include a treatment to lower androgen levels, such as surgical or chemical castration, or a treatment to inhibit the activity of cancer-promoting activity of androgens. Lowering androgen levels or inhibiting androgen activity may result in slowing of the growth of the prostate tumor, and in some cases shrinkage of the tumor. Suitable treatments to inhibit the activity of cancer-promoting androgens include the administration of anti-androgens, which may bind to an androgen receptor. Anti-androgens include, without limitation, cyproterone acetate, megestrol acetate, chlormadinone acetate, spironolactone, oxendolone, flutamide, bicalutamide, nilutamide, topilutamide, enzalutamide, abiraterone or apalutamide.

The presently disclosed methods may be useful for treating subjects who are unresponsive to androgen deprivation therapy. Some prostate cancers, such as CRPC, may not respond to or become resistant to androgen deprivation therapy. As demonstrated in the Examples, 15u is effective in suppressing prostate tumor growth of CRPC. As a result, 15u may be administered to a subject having previously undergone an androgen deprivation therapy or to those subjects unresponsive to androgen deprivation therapy.

The presently disclosed methods may also be useful for treating subjects currently undergoing androgen deprivation therapy. As demonstrated in the Examples, 15u is effective in suppressing prostate tumor growth of CRPC when co-administered with an anti-androgen. As a result, 15u may be administered to a subject currently undergoing androgen deprivation therapy.

In some embodiments, the CDK8/19-associated disease is a leukemia, suitably an acute myeloid leukemia.

In some embodiments, the CDK8/19-associated disease is a breast cancer, suitably a metastatic breast cancer.

Methods of Inhibiting CDK8 or CDK19

The compositions described are useful for inhibiting CDK8 and/or CDK19. As used herein, "inhibiting CDK8" or "inhibiting CDK19" means to inhibit the activity of CDK8 or CDK18, respectively, by any suitable mechanism, including competitive binding. The method of inhibiting CDK8 and/or CDK19 may comprise contacting any of the compounds or compositions described herein with CDK8 or CDK19. The extent of inhibition may be measured by the assays taught in the Examples in this Specification, including assay conditions employed by the service providers utilized herein. Results of these assays are commonly expressed herein as percent of control (POC), with the control being no compound being present. Alternatively, the results may be expressed as IC50. In some embodiments, the POC is less than 35%, suitably less than 30%, 25%, 20%, 15%, 10%, 5%, or 1% for an effective amount of any of the compounds of compositions described herein. In some embodiments, the IC50 is less than 2000 nM, 1500 nM, 1000 nM, 750 nM, 500 nM, 250 nM, 200 nM 150 nM, 100 nM, 75 nM, 50, nM, 40 nM, 30 nM, or 25 nM.

In some embodiments, the compounds and compositions disclosed herein specifically inhibit CDK8 or CDK19. As used herein, a compound or composition that "specifically inhibits CDK8" or "specifically inhibits CDK19" is a compound or composition that inhibits one or more CDK8 or CDK19, respectively, to a greater extent than it inhibits certain other CDKs. In some embodiments, such compounds further inhibit CDK8 and/or CDK19 to a greater extent than CDK2, CDK3, CDK4, CDK5, CDK7, CDK9, CDK11A, CDK11B, CDK13, CDK14, CDK15, CDK16, CDK17, CDK18, CDKL1, CDKL3, or CDKL5. In preferred embodiments, such greater extent is at least 2-fold more, or at least 3-fold more, than CDK2, CDK3, CDK4, CDK5, CDK7, CDK9, CDK11A, CDK11B, CDK13, CDK14, CDK15, CDK16, CDK17, CDK18, CDKL1, CDKL3, or CDKL5.

Miscellaneous

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Example 1. Thienopyridine Derivatives Inhibit CDK8/19 Activity in a Cell-Based Assay NFκB Activity Assay. We used a cell-based assay to measure the inhibition of CDK8/19 activity by thienopyridine derivatives. This assay, based on the role of CDK8/19 in NFκB-driven transcription (Li et al., Characterizing CDK8/19 Inhibitors through a NFκB-Dependent Cell-Based Assay, Cells 2019, 8(10), 1208), measures the effects of CDK8/19 on the expression of firefly luciferase reporter from a NFκB-dependent promoter in 293 cells. Lentiviral vector pHAGE-NFKB-TA-LUC-UBC-dTomato-W (Addgene #49335) was introduced into 293 cells and a clonal cell line showing the strongest induction of luciferase expression upon TNFα treatment was established and used as the reporter cell line. As a control for CDK8/19 dependence of NFκB inhibition, we have also introduced the same reporter construct into 293 cells with CRISPR/CAS9 knockout of both CDK8 and CDK19.

Figure 1B:
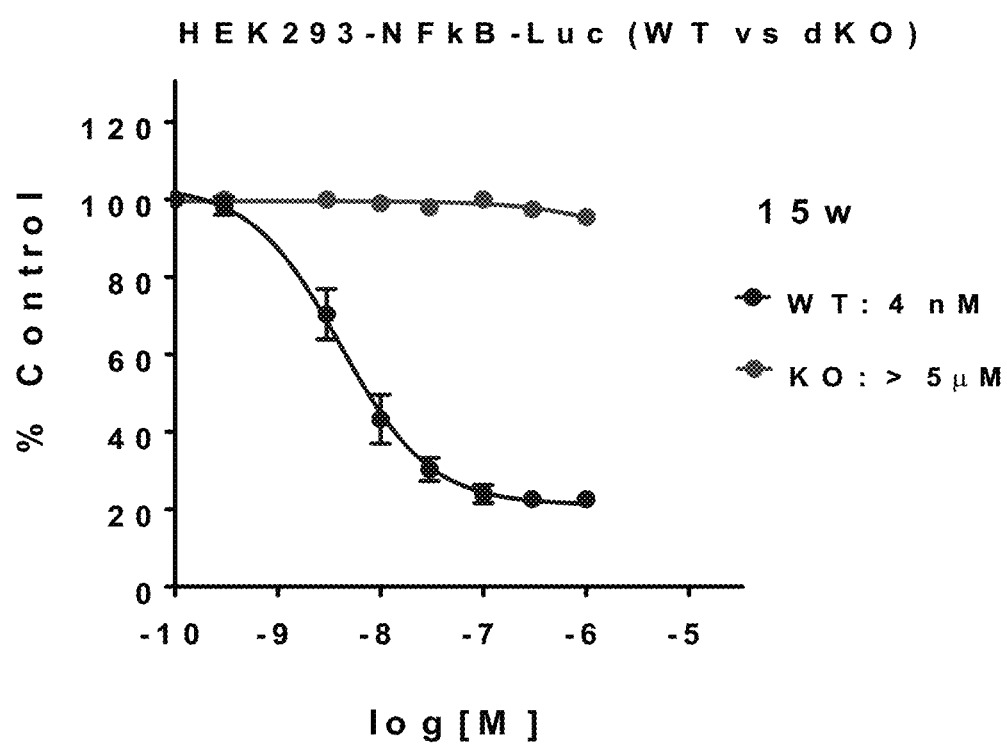

NFκB Activity Results. FIGS. 1A and 1B show the effects of different concentrations of 15u and 15w on NFκB reporter activity in parental 293 and in CDK8/19 deficient (double-knockout) reporter cells. While these compounds inhibited the reporter induction at IC50 values of 10 and 4 nM, respectively, they had no effect on NFκB activation in CDK8/19-deficient cells, demonstrating that the inhibitory effects of both compounds depend on the presence of CDK8/19 and not on other determinants of NFκB activity, such as IKK.

Figure 1C:
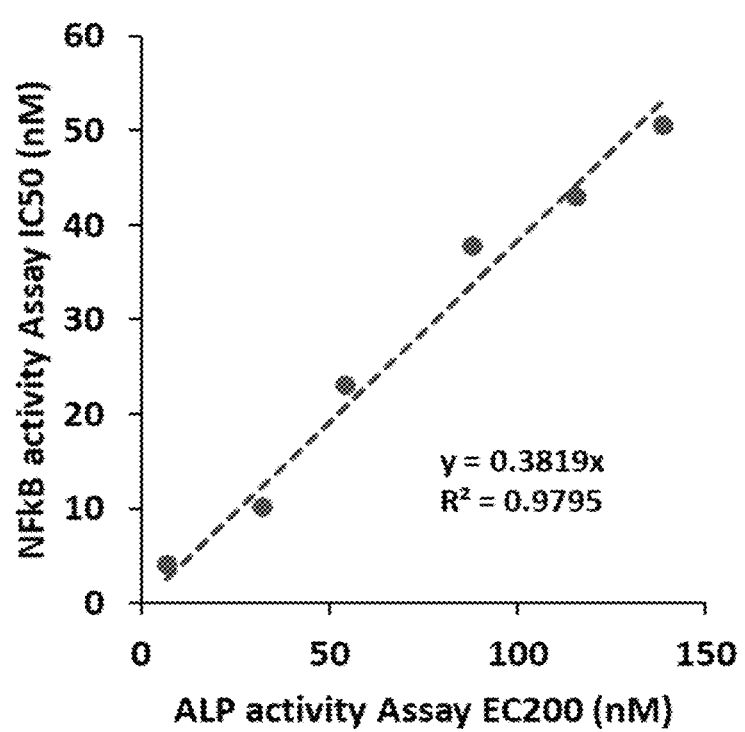
FIG. 1C compares the IC50 values for different thienopyridines measured in the NFκB reporter assay in a parental 293-derived reporter cell line to the cell-based activity values measured for the same compounds by Saito (2013) based on their effect on alkaline phosphatase (ALPase) in the mouse bone marrow stromal cell line ST2.
Figure 2A:
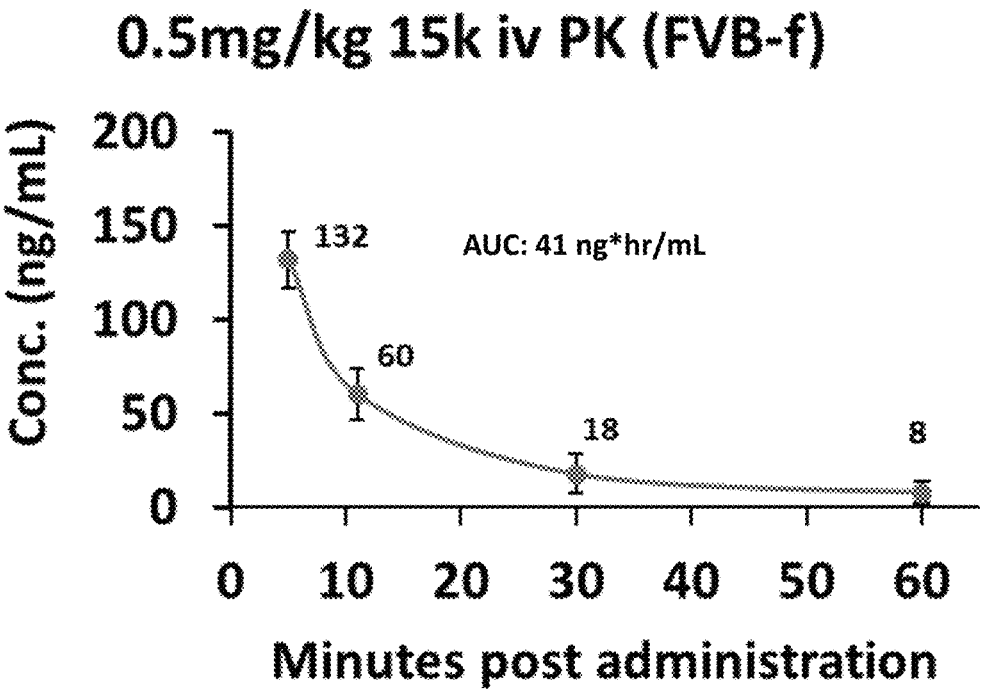
FIGS. 2A-2D shows the PK profiles and calculated parameters in female FVB mice for 15k (FIG. 2A), 15v (FIG. 2B), 15u (FIG. 2C), and Senexin B (FIG. 2D) administered to mice intravenously (i.v.) at 0.5 mg/kg of each compound.
Figure 2B:
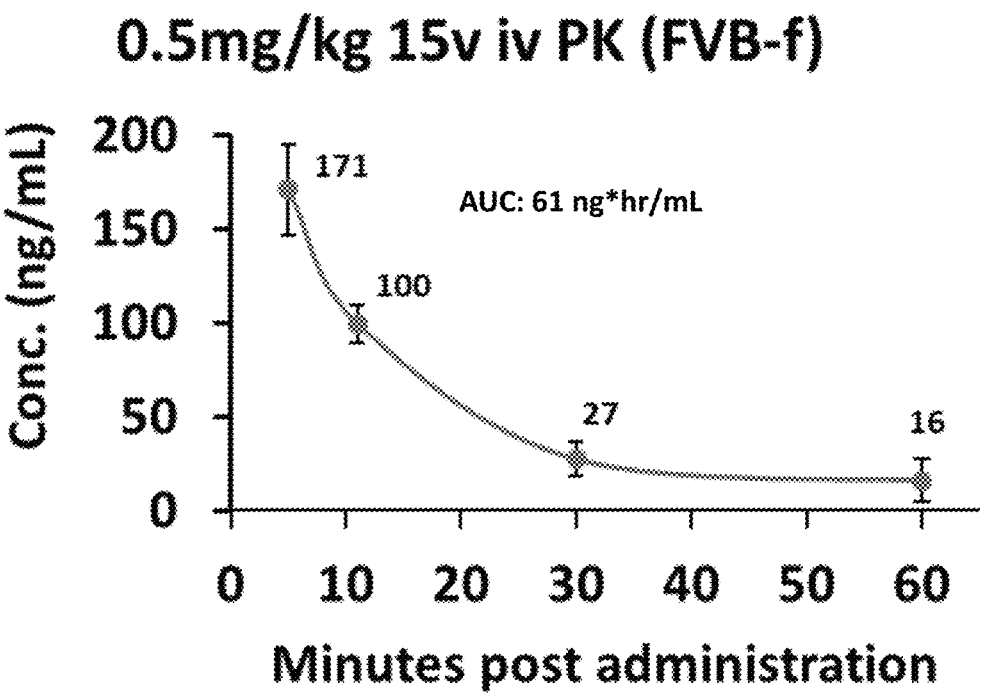
Figure 2C:
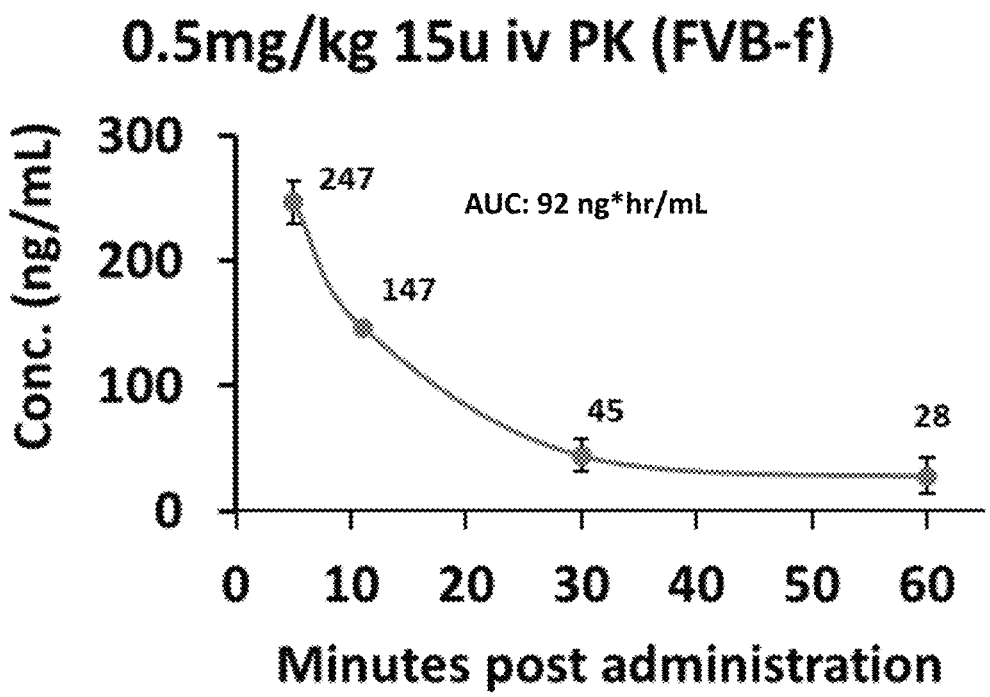
Figure 2D:
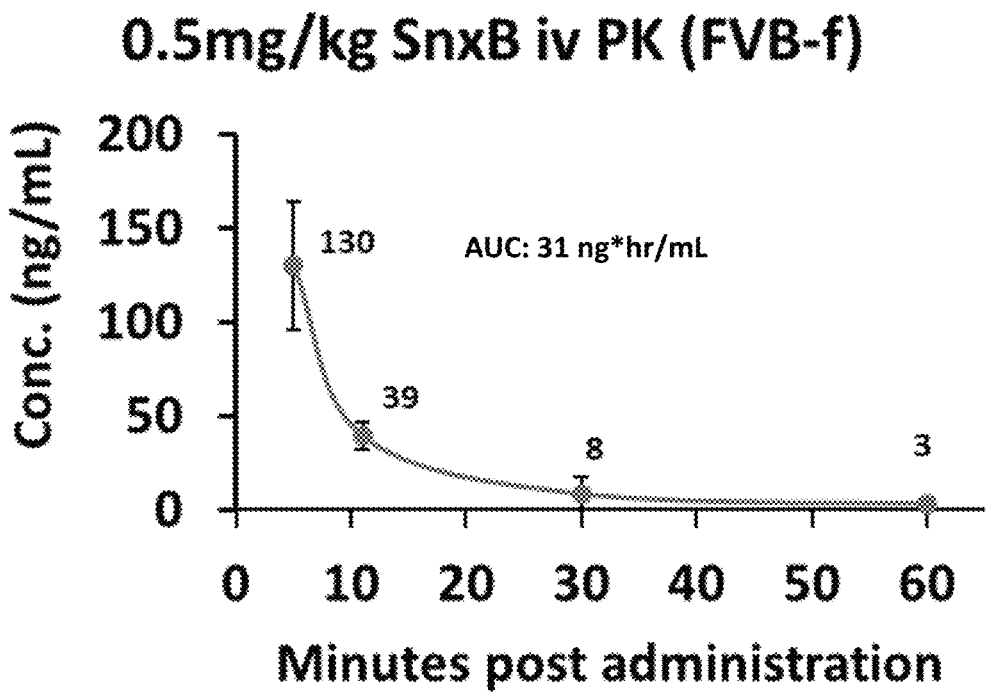

FIG. 1C and Table 1 compares the IC50 values for different thienopyridines measured in the NFκB reporter assay in parental 293-derived reporter cell line to the cell-based activity values measured for the same compounds by Saito (2013) based on their effect on alkaline phosphatase (ALPase), an indicator of differentiation to osteoblasts in the mouse bone marrow stromal cell line ST2. The latter effects are expressed as $EC_{200}$, a concentration that enhances ALPase activity to 200% of control. The IC50 values in the CDK8/19 NFkB assay are very strongly correlated with ALPase $EC_{200}$ values (FIG. 1), indicating that the ALPase effect is most likely mediated through CDK8/19 inhibition.

TABLE 1

Comparison of ALP and NFκB activity

|     | ALP activity Assay EC200 (nM) | NFκB activity Assay IC50 (nM) |
| --- | --- | --- |
| 15k | 138.8 | 50.6 |
| 15q | 115.4 | 43.1 |
| 15n | 88.1 | 37.8 |
| 15u | 31.9 | 10.3 |
| 15v | 54.2 | 23.1 |
| 15w | 6.6 | 4.1 |

Example 2. Kinome Profiling of Thienopyridine Derivatives

Table 2 shows the kinome profile of 15u_D6 and 15u as measured via the KINOMEscan™ site-directed competition binding assay at 2000 nM concentration. Compounds that bind the kinase active site and directly (sterically) or indirectly (allosterically) prevent kinase binding to the immobilized ligand, will reduce the amount of kinase captured on the solid support. Conversely, test molecules that do not bind the kinase have no effect on the amount of kinase captured on the solid support. Screening "hits" are identified by measuring the amount of kinase captured in test versus control samples by using a quantitative, precise and ultra-sensitive qPCR method that detects the associated DNA label. In a similar manner, dissociation constants (Kds) for test compound-kinase interactions are calculated by measuring the amount of kinase captured on the solid support as a function of the test compound concentration. A detailed description of the assay technology may be found in Fabian, M. A. et al. A small molecule-kinase interaction map for clinical kinase inhibitors. Nat. Biotechnol. 23, 329-336 (2005).

Percent Control (% Ctrl). The compounds were screened at a 10 nM concentration, and results for primary screen binding interactions are reported as "% Ctrl" or "POC", where lower numbers indicate stronger hits in the matrix. % Ctrl is defined as (eqn 1):

$$\% \text{ Ctrl} = 100 \times (TS-CPOS)/(CNEG-CPOS) \quad \text{(eqn 1)}$$

where TS is the test compound signal, CPOS is the positive control signal (0% Ctrl), CNEG is the DMSO negative control (100% Ctrl).

Results. Table 2 compares the results of kinome profiling between 15u and 15u_D6. Both 15u and 15u_D6 are highly selective for CDK8 and CDK19. Although 15u_D6 showed somewhat greater inhibition for most of the off-target kinases, the effect of 15u_D6 on CDK8 and CDK19 was much greater than the effect of 15u. The % Ctrl of 15u for CDK8 and CDK19 are 2.6 and 13, respectively. The % Ctrl of 15u_D6 for CDK8 and CDK19 are 0.25 and 0, respectively. Hence, the structural difference between 15u and 15u_D6 results in a major difference in target selectivity.

TABLE 2

ScanMAX panel of 15u and 15u_D6 at 2000 nM.

| Entrez Gene Symbol | 15u (% Ctrl) | 15u_D6 (% Ctrl) | Entrez Gene Symbol | 15u (% Ctrl) | 15u_D6 (% Ctrl) |
|---|---|---|---|---|---|
| AAK1 | 94 | 90 | MAX | 100 | 91 |
| ABL1(E255K)-phosphorylated | 100 | 82 | MAP3K1 | 84 | 90 |
| ABL1(F317I)-nonphosphorylated | 100 | 93 | MAP3K15 | 97 | 92 |
| ABL1(F317I)-phosphorylated | 88 | 84 | MAP3K2 | 98 | 86 |
| ABL1(F317L)-nonphosphorylated | 99 | 100 | MAP3K3 | 100 | 72 |
| ABL1(F317L)-phosphorylated | 97 | 82 | MAP3K4 | 90 | 100 |
| ABL1(H396P)-nonphosphorylated | 100 | 76 | MAP4K2 | 84 | 66 |
| ABL1(H396P)-phosphorylated | 94 | 77 | MAP4K3 | 91 | 95 |
| ABL1(M351T)-phosphorylated | 100 | 77 | MAP4K4 | 100 | 93 |
| ABL1(Q252H)-nonphosphorylated | 94 | 83 | MAP4K5 | 100 | 97 |
| ABL1(Q252H)-phosphorylated | 94 | 75 | MAPKAPK2 | 91 | 99 |
| ABL1(T315I)-nonphosphorylated | 100 | 85 | MAPKAPK5 | 100 | 64 |
| ABL1(T315I)-phosphorylated | 90 | 78 | MARK1 | 100 | 100 |
| ABL1(Y253F)-phosphorylated | 100 | 81 | MARK2 | 100 | 96 |
| ABL1-nonphosphorylated | 95 | 78 | MARK3 | 98 | 100 |
| ABL1-phosphorylated | 90 | 77 | MARK4 | 100 | 98 |
| ABL2 | 85 | 91 | MAST1 | 92 | 92 |
| ACVR1 | 100 | 100 | MEK1 | 93 | 83 |
| ACVR1B | 100 | 99 | MEK2 | 88 | 82 |
| ACVR2A | 95 | 92 | MEK3 | 68 | 47 |
| ACVR2B | 100 | 86 | MEK4 | 69 | 74 |
| ACVRL1 | 99 | 100 | MEK5 | 86 | 65 |
| ADCK3 | 90 | 100 | MEK6 | 100 | 96 |
| ADCK4 | 95 | 83 | MELK | 75 | 84 |
| AKT1 | 100 | 100 | MERTK | 89 | 100 |
| AKT2 | 86 | 99 | MET | 99 | 92 |
| AKT3 | 97 | 100 | MET(M1250T) | 100 | 96 |
| ALK | 81 | 78 | MET(Y1235D) | 100 | 100 |
| ALK(C1156Y) | 100 | 78 | MINK | 100 | 87 |
| ALK(L1196M) | 96 | 92 | MKK7 | 100 | 85 |
| AMPK-alpha1 | 100 | 100 | MKNK1 | 94 | 79 |
| AMPK-alpha2 | 80 | 95 | MKNK2 | 83 | 69 |
| ANKK1 | 100 | 91 | MLCK | 96 | 100 |
| ARK5 | 57 | 77 | MLK1 | 95 | 92 |
| ASK1 | 100 | 100 | MLK2 | 100 | 95 |
| ASK2 | 90 | 88 | MLK3 | 99 | 100 |
| AURKA | 98 | 99 | MRCKA | 94 | 100 |
| AURKB | 91 | 90 | MRCKB | 96 | 100 |
| AURKC | 100 | 100 | MST1 | 100 | 98 |
| AXL | 99 | 96 | MST1R | 97 | 99 |
| BIKE | 100 | 96 | MST2 | 100 | 84 |
| BLK | 100 | 92 | MST3 | 97 | 84 |
| BMPR1A | 100 | 100 | MST4 | 95 | 89 |
| BMPR1B | 100 | 62 | MTOR | 88 | 97 |
| BMPR2 | 79 | 88 | MUSK | 94 | 82 |
| BMX | 93 | 100 | MYLK | 74 | 71 |
| BRAF | 100 | 96 | MYLK2 | 100 | 100 |
| BRAF(V600E) | 100 | 84 | MYLK4 | 100 | 94 |
| BRK | 100 | 99 | MYO3A | 100 | 100 |
| BRSK1 | 86 | 97 | MYO3B | 87 | 100 |
| BRSK2 | 100 | 100 | NDR1 | 100 | 80 |
| BTK | 81 | 77 | NDR2 | 99 | 36 |
| BUB1 | 88 | 80 | NEK1 | 80 | 96 |
| CAMK1 | 83 | 95 | NEK10 | 93 | 61 |
| CAMK1B | 100 | 70 | NEK11 | 90 | 86 |
| CAMK1D | 87 | 93 | NEK2 | 95 | 95 |
| CAMK1G | 99 | 99 | NEK3 | 100 | 76 |
| CAMK2A | 90 | 100 | NEK4 | 100 | 95 |
| CAMK2B | 92 | 87 | NEK5 | 94 | 100 |
| CAMK2D | 99 | 92 | NEK6 | 92 | 100 |
| CAMK2G | 100 | 100 | NEK7 | 100 | 86 |
| CAMK4 | 96 | 79 | NEK9 | 100 | 89 |
| CAMKK1 | 96 | 100 | NIK | 100 | 97 |

TABLE 2-continued

ScanMAX panel of 15u and 15u_D6 at 2000 nM.

| Entrez Gene Symbol | 15u (% Ctrl) | 15u_D6 (% Ctrl) | Entrez Gene Symbol | 15u (% Ctrl) | 15u_D6 (% Ctrl) |
|---|---|---|---|---|---|
| CAMKK2 | 100 | 87 | NIM1 | 56 | 78 |
| CASK | 71 | 96 | NLK | 98 | 98 |
| CDC2L1 | 63 | 100 | OSR1 | 100 | 88 |
| CDC2L2 | 100 | 100 | p38-alpha | 93 | 99 |
| CDC2L5 | 71 | 80 | p38-beta | 100 | 97 |
| CDK11 (CDK19) | 13 | 0 | p38-delta | 96 | 97 |
| CDK2 | 100 | 99 | p38-gamma | 98 | 100 |
| CDK3 | 92 | 97 | PAK1 | 96 | 92 |
| CDK4 | 73 | 71 | PAK2 | 91 | 94 |
| CDK4-cyclinD1 | 94 | 96 | PAK3 | 80 | 40 |
| CDK4-cyclinD3 | 95 | 97 | PAK4 | 87 | 100 |
| CDK5 | 84 | 94 | PAK6 | 82 | 99 |
| CDK7 | 100 | 78 | PAK7 | 100 | 80 |
| CDK8 | 2.6 | 0.25 | PCTK1 | 92 | 64 |
| CDK9 | 66 | 100 | PCTK2 | 62 | 100 |
| CDKL1 | 100 | 92 | PCTK3 | 100 | 100 |
| CDKL2 | 86 | 96 | PDGFRA | 70 | 65 |
| CDKL3 | 100 | 100 | PDGFRB | 100 | 93 |
| CDKL5 | 100 | 84 | PDPK1 | 100 | 96 |
| CHEK1 | 94 | 100 | PFCDPK1 (P.falciparum) | 94 | 61 |
| CHEK2 | 92 | 92 | PFPK5(P.falciparum) | 68 | 67 |
| CIT | 51 | 65 | PFTAIRE2 | 100 | 80 |
| CLK1 | 88 | 68 | PFTK1 | 96 | 100 |
| CLK2 | 75 | 83 | PHKG1 | 94 | 97 |
| CLK3 | 100 | 95 | PHKG2 | 86 | 83 |
| CLK4 | 59 | 66 | PIK3C2B | 89 | 87 |
| CSF1R | 98 | 95 | PIK3C2G | 94 | 82 |
| CSF1R-autoinhibited | 88 | 83 | PIK3CA | 100 | 79 |
| CSK | 86 | 92 | PIK3CA(C420R) | 100 | 86 |
| CSNK1A1 | 33 | 12 | PIK3CA(E542K) | 92 | 74 |
| CSNK1A1L | 67 | 37 | PIK3CA(E545A) | 100 | 92 |
| CSNK1D | 20 | 22 | PIK3CA(E545K) | 96 | 91 |
| CSNK1E | 25 | 12 | PIK3CA(H1047L) | 94 | 80 |
| CSNK1G1 | 90 | 80 | PIK3CA(H1047Y) | 79 | 100 |
| CSNK1G2 | 77 | 69 | PIK3CA(I800L) | 97 | 74 |
| CSNK1G3 | 95 | 80 | PIK3CA(M1043I) | 96 | 95 |
| CSNK2A1 | 100 | 59 | PIK3CA(Q546K) | 66 | 72 |
| CSNK2A2 | 92 | 100 | PIK3CB | 100 | 95 |
| CTK | 92 | 100 | PIK3CD | 94 | 71 |
| DAPK1 | 92 | 88 | PIK3CG | 79 | 76 |
| DAPK2 | 75 | 85 | PIK4CB | 65 | 33 |
| DAPK3 | 81 | 83 | PIKFYVE | 91 | 98 |
| DCAMKL1 | 100 | 89 | PIM1 | 88 | 100 |
| DCAMKL2 | 100 | 100 | PIM2 | 85 | 89 |
| DCAMKL3 | 91 | 100 | PIM3 | 89 | 98 |
| DDR1 | 82 | 90 | PIP5K1A | 100 | 100 |
| DDR2 | 80 | 52 | PIP5K1C | 64 | 25 |
| DLK | 93 | 89 | PIP5K2B | 92 | 95 |
| DMPK | 97 | 97 | PIP5K2C | 80 | 64 |
| DMPK2 | 93 | 94 | PKAC-alpha | 95 | 100 |
| DRAK1 | 100 | 100 | PKAC-beta | 83 | 100 |
| DRAK2 | 100 | 87 | PKMYT1 | 91 | 94 |
| DYRK1A | 50 | 22 | PKN1 | 96 | 100 |
| DYRK1B | 69 | 100 | PKN2 | 100 | 100 |
| DYRK2 | 100 | 97 | PKNB (M.tuberculosis) | 100 | 90 |
| EGFR | 100 | 87 | PLK1 | 95 | 89 |
| EGFR(E746-A750del) | 100 | 100 | PLK2 | 100 | 86 |
| EGFR(G719C) | 97 | 100 | PLK3 | 86 | 90 |
| EGFR(G719S) | 100 | 100 | PLK4 | 95 | 92 |
| EGFR(L747-E749del, A750P) | 99 | 100 | PRKCD | 100 | 92 |
| EGFR(L747-S752del, P753S) | 99 | 100 | PRKCE | 93 | 97 |
| EGFR(L747-T751del, Sins) | 87 | 100 | PRKCH | 80 | 96 |
| EGFR(L858R) | 99 | 93 | PRKCI | 100 | 100 |
| EGFR(L858R,T790M) | 100 | 87 | PRKCQ | 90 | 87 |
| EGFR(L861Q) | 78 | 100 | PRKD1 | 88 | 92 |
| EGFR(S752-I759del) | 86 | 100 | PRKD2 | 56 | 90 |
| EGFR(T790M) | 98 | 87 | PRKD3 | 94 | 100 |
| EIF2AK1 | 93 | 78 | PRKG1 | 88 | 100 |
| EPHA1 | 92 | 95 | PRKG2 | 98 | 90 |
| EPHA2 | 95 | 100 | PRKR | 100 | 100 |
| EPHA3 | 100 | 87 | PRKX | 94 | 95 |
| EPHA4 | 100 | 100 | PRP4 | 100 | 88 |
| EPHA5 | 89 | 96 | PYK2 | 97 | 84 |

TABLE 2-continued

ScanMAX panel of 15u and 15u_D6 at 2000 nM.

| Entrez Gene Symbol | 15u (% Ctrl) | 15u_D6 (% Ctrl) | Entrez Gene Symbol | 15u (% Ctrl) | 15u_D6 (% Ctrl) |
|---|---|---|---|---|---|
| EPHA6 | 100 | 100 | QSK | 89 | 97 |
| EPHA7 | 92 | 81 | RAF1 | 97 | 100 |
| EPHA8 | 94 | 83 | RET | 93 | 86 |
| EPHB1 | 88 | 88 | RET(M918T) | 98 | 98 |
| EPHB2 | 99 | 95 | RET(V804L) | 100 | 100 |
| EPHB3 | 96 | 94 | RET(V804M) | 100 | 100 |
| EPHB4 | 100 | 100 | RIOK1 | 100 | 100 |
| EPHB6 | 95 | 89 | RIOK2 | 35 | 3.9 |
| ERBB2 | 100 | 89 | RIOK3 | 100 | 95 |
| ERBB3 | 100 | 88 | RIPK1 | 99 | 100 |
| ERBB4 | 85 | 100 | RIPK2 | 100 | 93 |
| ERK1 | 100 | 97 | RIPK4 | 89 | 68 |
| ERK2 | 78 | 92 | RIPK5 | 100 | 72 |
| ERK3 | 88 | 94 | ROCK1 | 77 | 67 |
| ERK4 | 72 | 100 | ROCK2 | 100 | 80 |
| ERK5 | 59 | 98 | ROS1 | 95 | 100 |
| ERK8 | 98 | 99 | RPS6KA4(Kin.Dom.1-N-terminal) | 96 | 100 |
| ERN1 | 100 | 80 | RPS6KA4(Kin.Dom.2-C-terminal) | 100 | 74 |
| FAK | 100 | 96 | RPS6KA5(Kin.Dom.1-N-terminal) | 75 | 100 |
| FER | 99 | 100 | RPS6KA5(Kin.Dom.2-C-terminal) | 95 | 100 |
| FES | 100 | 100 | RSK1(Kin.Dom.1-N-terminal) | 98 | 96 |
| FGFR1 | 98 | 92 | RSK1(Kin.Dom.2-C-terminal) | 100 | 86 |
| FGFR2 | 99 | 98 | RSK2(Kin.Dom.1-N-terminal) | 90 | 64 |
| FGFR3 | 98 | 99 | RSK2(Kin.Dom.2-C-terminal) | 94 | 92 |
| FGFR3(G697C) | 95 | 100 | RSK3(Kin.Dom.1-N-terminal) | 99 | 77 |
| FGFR4 | 100 | 96 | RSK3(Kin.Dom.2-C-terminal) | 100 | 89 |
| FGR | 100 | 100 | RSK4(Kin.Dom.1-N-terminal) | 78 | 80 |
| FLT1 | 100 | 100 | RSK4(Kin.Dom.2-C-terminal) | 94 | 79 |
| FLT3 | 94 | 86 | S6K1 | 95 | 89 |
| FLT3(D835H) | 63 | 76 | SBK1 | 100 | 83 |
| FLT3(D835V) | 33 | 14 | SGK | 86 | 83 |
| FLT3(D835Y) | 46 | 100 | SgK110 | 95 | 100 |
| FLT3 (ITD) | 82 | 72 | SGK2 | 100 | 81 |
| FLT3(ITD, D835V) | 41 | 34 | SGK3 | 79 | 80 |
| FLT3(ITD, F691L) | 95 | 75 | SIK | 84 | 79 |
| FLT3(K663Q) | 96 | 91 | SIK2 | 96 | 100 |
| FLT3(N841I) | 90 | 86 | SLK | 56 | 54 |
| FLT3(R834Q) | 100 | 68 | SNARK | 100 | 78 |
| FLT3-autoinhibited | 72 | 77 | SNRK | 100 | 75 |
| FLT4 | 92 | 98 | SRC | 100 | 96 |
| FRK | 100 | 97 | SRMS | 81 | 93 |
| FYN | 99 | 97 | SRPK1 | 100 | 97 |
| GAK | 88 | 94 | SRPK2 | 93 | 100 |
| GCN2(Kin.Dom.2, S808G) | 73 | 88 | SRPK3 | 65 | 96 |
| GRK1 | 98 | 81 | STK16 | 80 | 87 |
| GRK2 | 88 | 70 | STK33 | 100 | 100 |
| GRK3 | 99 | 87 | STK35 | 87 | 93 |
| GRK4 | 62 | 98 | STK36 | 100 | 100 |
| GRK7 | 100 | 92 | STK39 | 93 | 94 |
| GSK3A | 31 | 34 | SYK | 95 | 100 |
| GSK3B | 79 | 77 | TAK1 | 93 | 62 |
| HASPIN | 20 | 8.9 | TAOK1 | 100 | 73 |
| HCK | 96 | 96 | TAOK2 | 92 | 93 |
| HIPK1 | 86 | 71 | TAOK3 | 98 | 73 |
| HIPK2 | 100 | 81 | TBK1 | 99 | 97 |
| HIPK3 | 77 | 81 | TEC | 91 | 81 |
| HIPK4 | 100 | 100 | TESK1 | 83 | 100 |
| HPK1 | 98 | 100 | TGFBR1 | 100 | 100 |
| HUNK | 99 | 100 | TGFBR2 | 100 | 100 |
| ICK | 84 | 66 | TIE1 | 90 | 96 |
| IGF1R | 92 | 91 | TIE2 | 72 | 100 |
| IKK-alpha | 77 | 90 | TLK1 | 97 | 85 |
| IKK-beta | 89 | 71 | TLK2 | 100 | 97 |

TABLE 2-continued

ScanMAX panel of 15u and 15u_D6 at 2000 nM.

| Entrez Gene Symbol | 15u (% Ctrl) | 15u_D6 (% Ctrl) | Entrez Gene Symbol | 15u (% Ctrl) | 15u_D6 (% Ctrl) |
|---|---|---|---|---|---|
| IKK-epsilon | 100 | 100 | TNIK | 100 | 91 |
| INSR | 97 | 80 | TNK1 | 100 | 100 |
| INSRR | 99 | 89 | TNK2 | 100 | 100 |
| IRAK1 | 94 | 84 | TNNI3K | 100 | 100 |
| IRAK3 | 93 | 89 | TRKA | 93 | 78 |
| IRAK4 | 89 | 78 | TRKB | 88 | 78 |
| ITK | 88 | 87 | TRKC | 91 | 85 |
| JAK1(JH1domain-catalytic) | 57 | 82 | TRPM6 | 100 | 80 |
| JAK1(JH2domain-pseudokinase) | 89 | 89 | TSSK1B | 80 | 99 |
| JAK2(JH1domain-catalytic) | 100 | 93 | TSSK3 | 93 | 100 |
| JAK3(JH1domain-catalytic) | 83 | 80 | TTK | 83 | 80 |
| JNK1 | 68 | 30 | TXK | 93 | 100 |
| JNK2 | 99 | 54 | TYK2(JH1domain-catalytic) | 95 | 82 |
| JNK3 | 91 | 44 | TYK2(JH2domain-pseudokinase) | 73 | 59 |
| KIT | 95 | 95 | TYRO3 | 100 | 100 |
| KIT(A829P) | 97 | 51 | ULK1 | 96 | 72 |
| KIT (D816H) | 91 | 66 | ULK2 | 90 | 83 |
| KIT(D816V) | 93 | 79 | ULK3 | 96 | 79 |
| KIT(L576P) | 96 | 75 | VEGFR2 | 67 | 84 |
| KIT(V559D) | 98 | 91 | VPS34 | 85 | 65 |
| KIT(V559D, T670I) | 100 | 96 | VRK2 | 84 | 56 |
| KIT(V559D, V654A) | 100 | 100 | WEE1 | 100 | 88 |
| KIT-autoinhibited | 90 | 90 | WEE2 | 97 | 88 |
| LATS1 | 89 | 97 | WNK1 | 100 | 93 |
| LATS2 | 94 | 31 | WNK2 | 96 | 94 |
| LCK | 91 | 100 | WNK3 | 97 | 100 |
| LIMK1 | 100 | 100 | WNK4 | 60 | 98 |
| LIMK2 | 91 | 98 | YANK1 | 89 | 97 |
| LKB1 | 100 | 87 | YANK2 | 89 | 84 |
| LOK | 84 | 69 | YANK3 | 81 | 97 |
| LRRK2 | 94 | 70 | YES | 99 | 100 |
| LRRK2(G2019S) | 90 | 76 | YSK1 | 76 | 98 |
| LTK | 90 | 77 | YSK4 | 74 | 53 |
| LYN | 100 | 98 | ZAK | 94 | 100 |
| LZK | 100 | 87 | ZAP70 | 95 | 87 |

The effects on all the kinases that showed >65 inhibition by 2,000 nM 15u in this screen (CDK8, CDK19, RIOK2, CSNK1A1, CSNK1E, SCNK1D, HASPIN, GSK3A) were then further investigated by measuring Kd values of 15u in the DiscoverX assay. The Kd assays were carried out in duplicates and the results are presented in Table 3. This table also shows the results of Kd determination for 15w versus CDK8, CDK19 and RIOK2.

TABLE 3

Kd values for 15u and 15w in Kd Elect binding assays with susceptible kinases.

| Compound Name | DiscoveRx Gene Symbol | Entrez Gene Symbol | $K_d$ (nM) |
|---|---|---|---|
| 15u | CDK11 | CDK19 | 65 |
| 15u | CDK8 | CDK8 | 78 |
| 15u | RIOK2 | RIOK2 | 240 |
| 15u | CSNK1A1 | CSNK1A1 | 230 |
| 15u | CSNK1D | CSNK1D | 860 |
| 15u | CSNK1E | CSNK1E | 280 |
| 15u | HASPIN | GSG2 | 1100 |
| 15u | GSK3A | GSK3A | 5600 |
| 15w | CDK11 | CDK19 | 18 |
| 15w | CDK8 | CDK8 | 55 |
| 15w | RIOK2 | RIOK2 | 130 |

Notably, the CDK8 and CDK19 $K_d$ values for 15u and 15w are almost an order of magnitude higher than their IC50 values for CDK8/19 inhibition in a cell-based assay (FIGS. 1A and 1B), indicating that the competition for ATP analog binding does not fully reflect the inhibitory activity of these compounds. The principal other kinases inhibited by 15u with $K_d$ values less than 4 times higher than for CDK8 are RIOK2 (also strongly inhibited by 15w). CSNK1A1 and CSNK1E were not tested against 15w.

Remarkably, the reported evidence suggests that the inhibition of these three kinases may be beneficial rather than detrimental for cancer treatment. Thus RIOK2, an atypical kinase regulating ribosomal biogenesis was identified as the target of a compound that selectively inhibited growth of prostate cancer cell lines carrying an oncogenic gene fusion that activates ERG gene in many prostate cancers. The same RIOK2-binding compound had only minimal effect on normal prostate or endothelial cells or ERG-negative tumor cell lines (Mohamed, A A et al., Cancer Res. 2018 Jul. 1; 78(13):3659-3671. doi: 10.1158/0008-5472.CAN-17-2949). CSNK1A1 has been implicated as an oncogenic factor in a variety of leukemias and solid tumors (Mannis, S. et al. J Hematol Oncol. 2017 Oct. 2; 10(1):157. doi: 10.1186/s13045-017-0529-5; Richter, J. et al., BMC Cancer. 2018 Feb. 6; 18(1):140. doi: 10.1186/s12885-018-4019-0) and CSNK1A1 inhibitors synergized with lysosomotropic agents to inhibit growth and promote tumor cell death in KRAS-driven cancers (Cheong, J. K. et al., J Clin Invest. 2015 April; 125(4):1401-18. doi: 10.1172/JCI78018). CSNK1E inhibition was reported to have selective antiproliferative activity in several types of tumor cells (Yang, W S, et al., Genome Biol. 2008; 9(6):R92. doi: 10.1186/gb-2008-

9-6-r92; Kim, S. Y. et al., PLoS One. 2010 Feb. 1; 5(2): e8979. doi: 10.1371/journal.pone.0008979; Toyoshima, M., et al., Proc Natl Acad Sci USA. 2012 Jun. 12; 109(24):9545-50. doi: 10.1073/pnas.1121119109; Varghese, R. T., et al., Sci Rep. 2018 Sep. 11; 8(1):13621. doi: 10.1038/s41598-018-31864-x.) Hence, 15u has unexpected activities for cancer therapy in addition to CDK8/19 inhibition.

Example 3. Pharmacokinetics of Thienopyridine Derivatives

Pharmacokinetics (PK) Assay. To measure mouse pharmacokinetics (PK), thienopyridine derivatives were dissolved in 5% dextrose and administered to female FVB mice at different dosing conditions; blood samples were collected at different time points and compound concentrations in the serum were measured by LC/MS/MS.

PK Results. FIGS. 2A-2D and Table 4 show the PK curves and calculated parameters for 15k, 15v, and 15u, which were mixed and administered to mice intravenously (i.v.) at 0.5 mg/kg of each compound. In this assay, 15u showed the highest and 15k the lowest availability i.v., as indicated by the values of Area Under the Curve (AUC) and Elimination half-time ($t_{1/2}$).

TABLE 4

Comparison of pharmacokinetics of 15k, 15v, and 15u administered intravenously

|  | 15k | 15v | 15u |
|---|---|---|---|
| $C_0$ (ng/mL) | 168.0 | 233.9 | 328.3 |
| $V_d$ (L/kg) | 2.98 | 2.14 | 1.52 |
| Elimination rate (hr$^{-1}$) | 4.59 | 4.33 | 4.03 |
| $t_{1/2}$ (hr) | 0.15 | 0.16 | 0.17 |
| AUC (ng * hr/mL) | 40.81 | 61.23 | 92.13 |

Figure 3A:
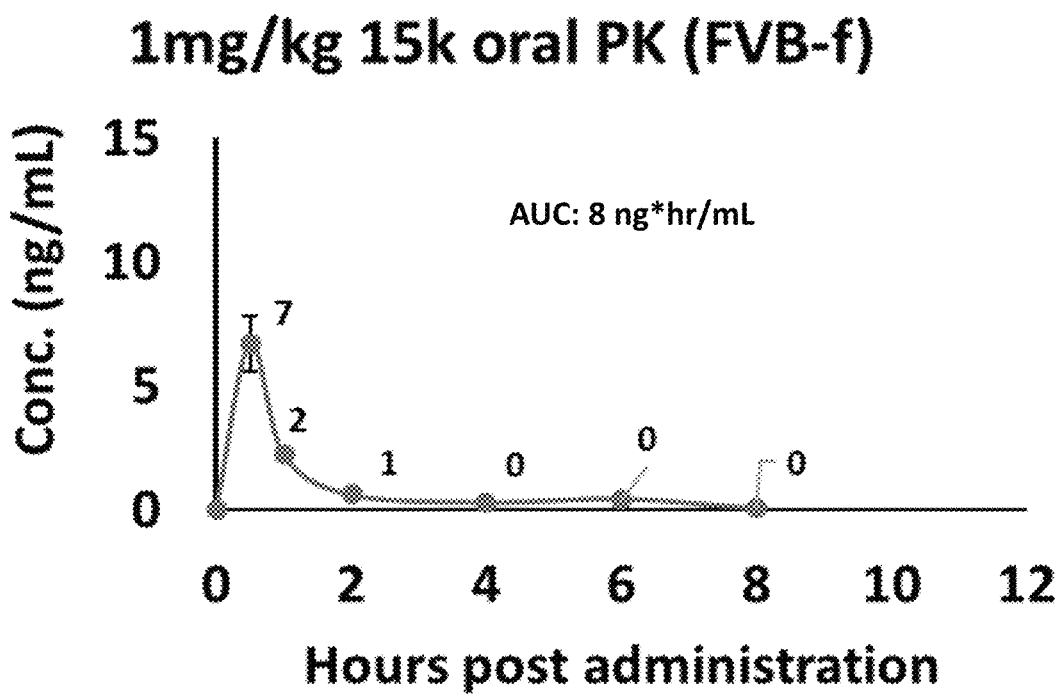
FIGS. 3A-3E shows the PK curves and calculated parameters for 15k (FIG. 3A), 15v (FIG. 3B), 15u (FIG. 3C), 15w (FIG. 3D), and Senexin B (FIG. 3E), administered to mice orally at 1 mg/kg of each compound.
Figure 3B:
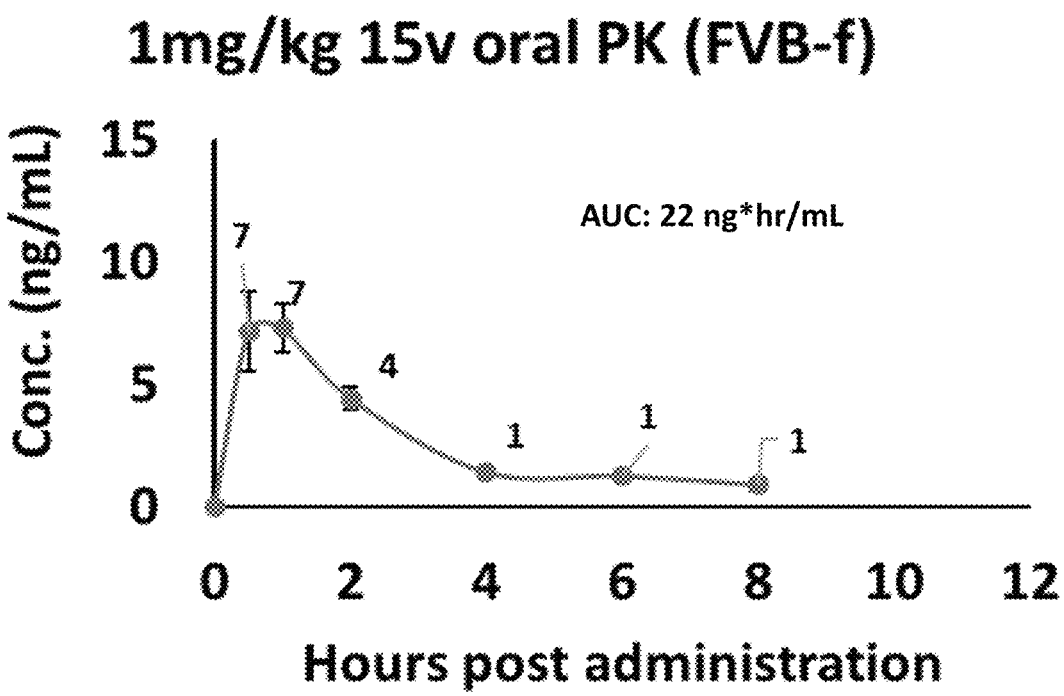
Figure 3C:
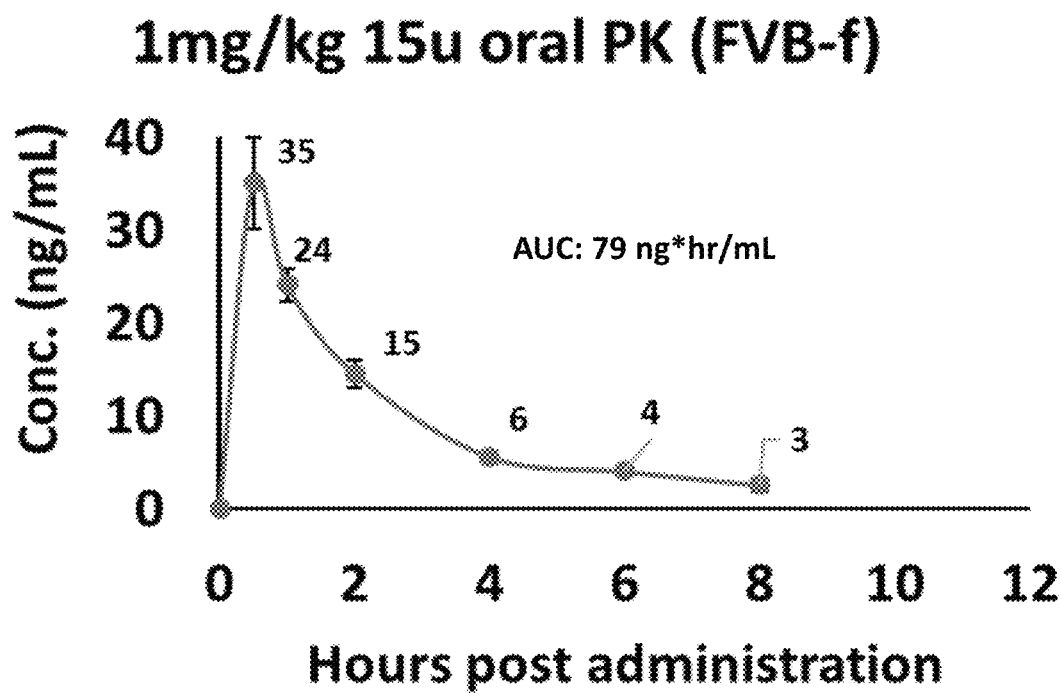
Figure 3D:
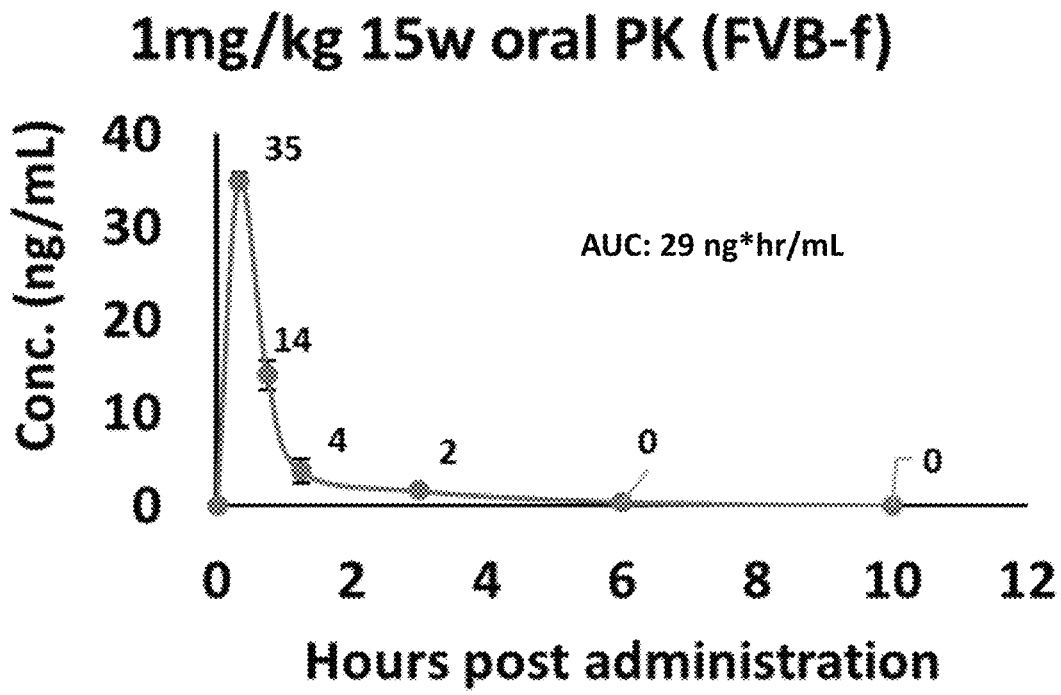
Figure 3E:
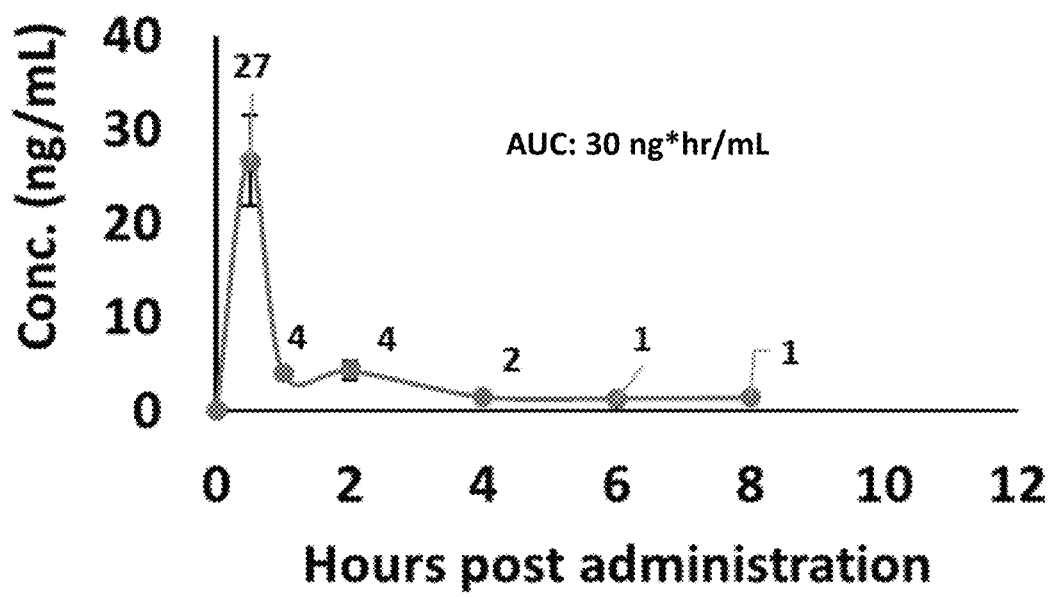

FIGS. 3A-3C and Table 5 shows the PK curves and calculated parameters for the same mixture of 15k, 15v, and 15u, administered orally (by gavage) at 1 mg/kg of each compound. In a separate study shown in FIG. 3D, 15w was also administered orally at 1 mg/kg. In these assays, 15u showed by far the highest availability (AUC value), followed by 15w, 15v and 15k. SnxB showed a similar AUC to 15w (FIG. 3E).

TABLE 5

Comparison of pharmacokinetics of 15k, 15v, 15u, and 15w administered orally

|  | 15k | 15v | 15u | 15w |
|---|---|---|---|---|
| $C_{max}$ (ng/mL) | 6.7 | 7.2 | 35.1 | 35.0 |
| $t_{1/2}$ (hr) | 0.3 | 1.2 | 1.3 | 0.3 |
| AUC (ng * hr/mL) | 7.6 | 21.8 | 79.3 | 29.2 |
| Bioavailability (F %) | 9% | 18% | 43% |  |

Figure 4A:
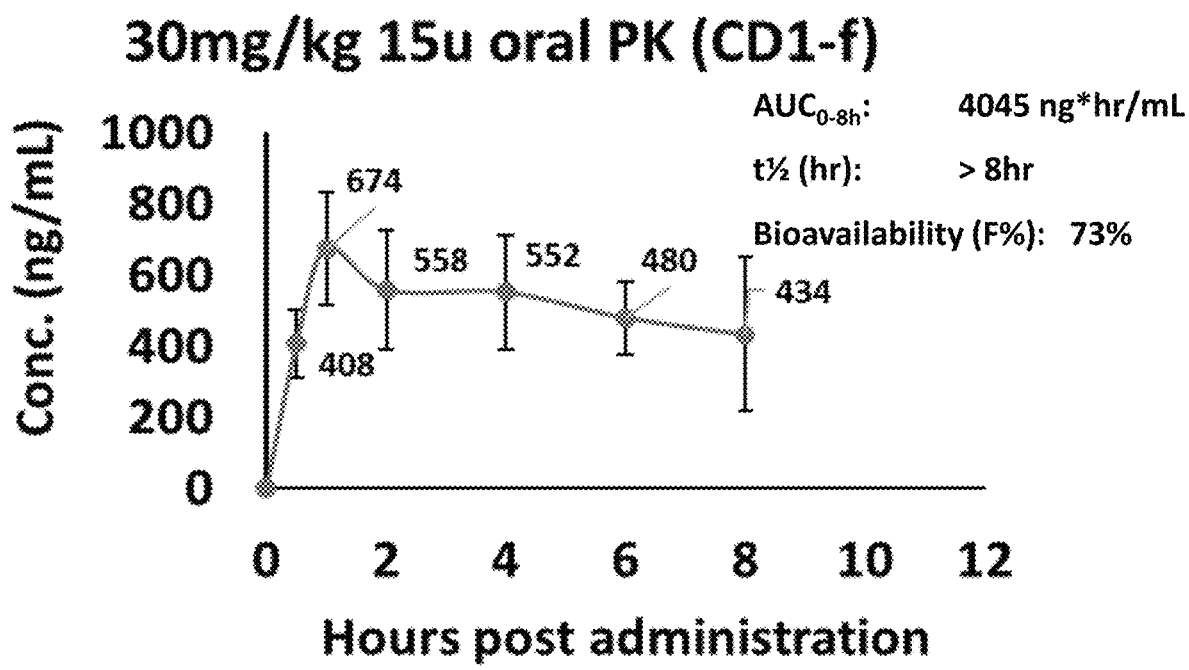
FIGS. 4A and 4B show the PK curves and calculated parameters for a mixture of 15u (FIG. 4A) and 15w (FIG. 4B), administered to female CD1 mice at 30 mg/kg of each compound.
Figure 4B:
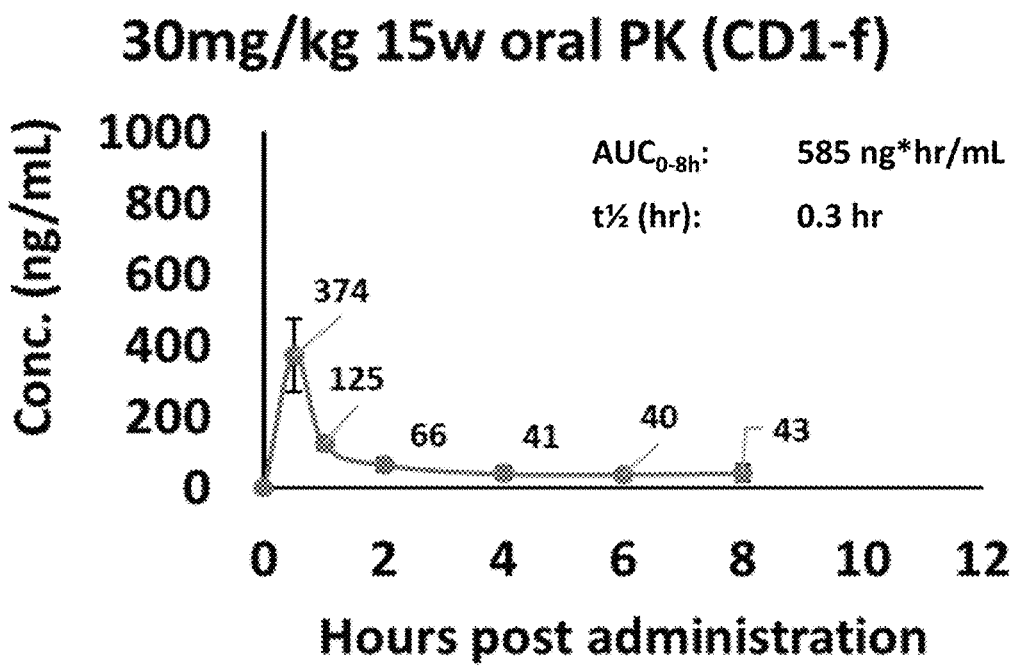

Oral PK was also determined at higher dosages, approximating the expected therapeutic doses, for a mixture of the two most active compounds, 15w and 15u, administered to female CD1 mice at 30 mg/kg of each compound in 0.5% carboxylmethyl cellulose. The results shown in FIGS. 4A and 4B demonstrate that 15u (but not 15w) shows excellent PK, with high AUC (6.9 times higher than the AUC of 15w) and very slow clearance, as the average serum concentration of 15u at the latest timepoint (8 hrs) was 64.4% of $C_{max}$ (vs. 11.5% for 15w).

This PK analysis demonstrated that 15u, alone of the tested thienopyridine derivatives, demonstrated highly appealing PK properties, with very high bioavailability and stability after oral administration.

Example 4. Pharmacokinetics Profile of Deuterated Derivatives of 15u and 15w

Figure 5A:
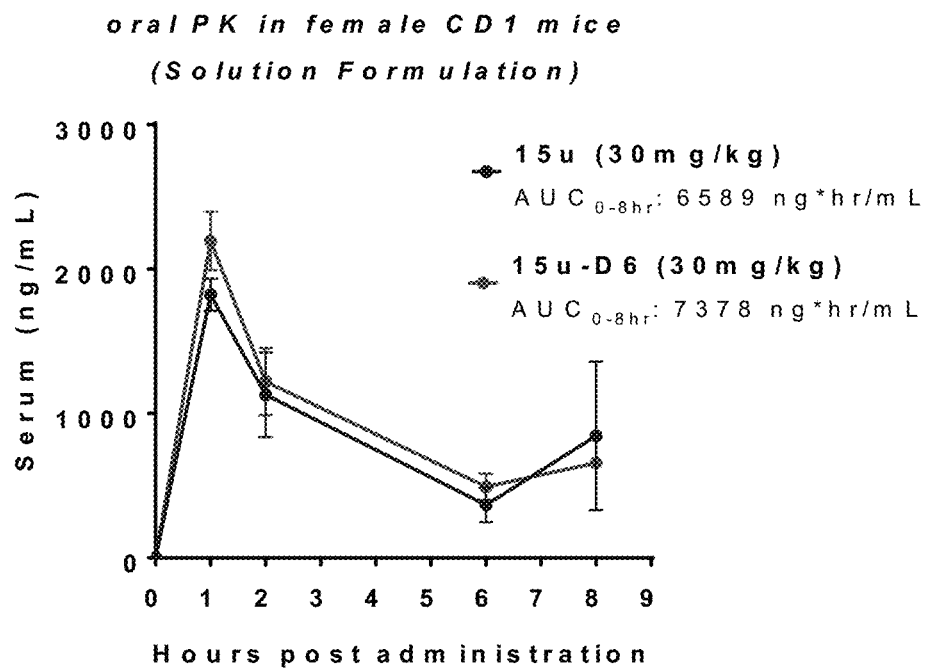
FIG. 5A shows the PK profiles of deuterated 15u_D6 and non-deuterated 15u administered to female CD-1 mice at 30 mg/kg of each compound.
Figure 5B:
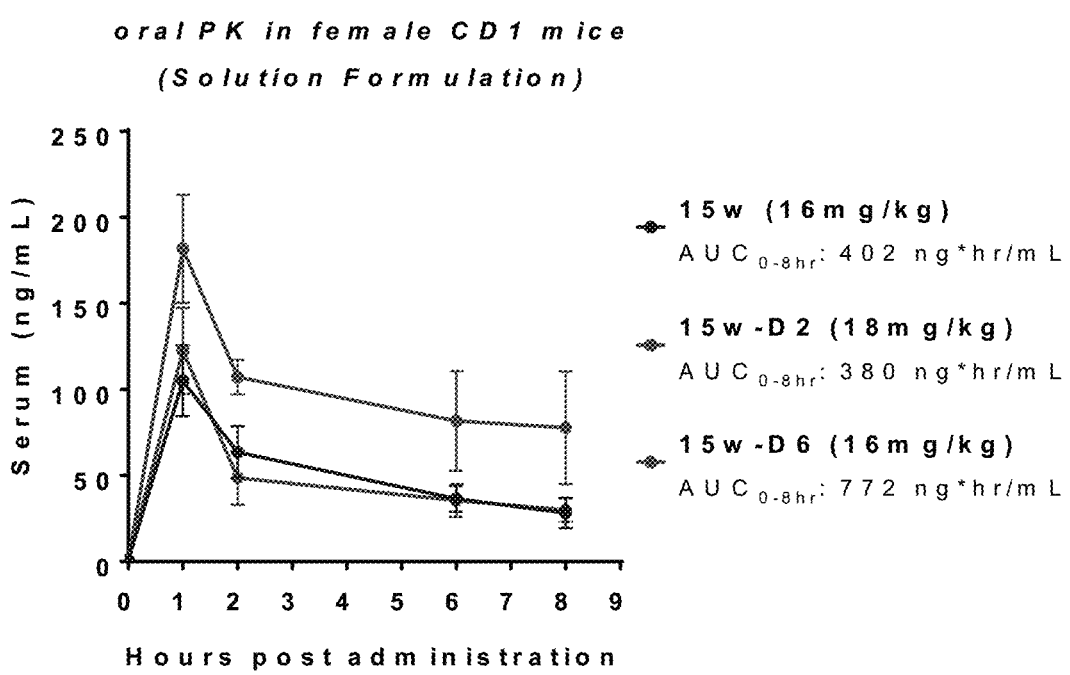
FIG. 5B shows the PK profiles of deuterated 15w_D2 and 15w_D6 and non-deuterated 15w administered to female CD-1 mice at 16 or 18 mg/kg of each compound.

To determine PKs of deuterated derivatives of 15u and 15w, eight to twelve-week-old female CD-1 mice were treated with 15u or 15u-D6 at 30 mg/kg or 15w, 15w-D2, 15w-D6 at 16 or 18 mg/kg by oral gavage in solution. Blood samples (70~100 μL) were collected into BD Microtainer blood collection tubes for serum separation at different time points (1, 2, 6, 8 hours post administration) with heparinized microhematocrit capillary tubes from retro-orbital veins of anesthetized animals. Serum samples were processed for LCMSMS to determine drug concentration using compound-specific MRMs (15u: 439-394; 15u-D6: 445-394; 15w: 453-436; 15w-D2: 455-438; 15w-D6: 459-442). Drug concentrations were plotted against time points to generate PK curves with GraphPad software and AUCs (area under the curve) within the first eight hours after dosing were calculated with Excel Software to compare PK profiles of undeuterated and deuterated compounds. These two PK studies indicate that replacing hydrogens of the dimethylamine group with deuterium (the D6 derivatives) slightly improved the PK for 15u (FIG. 5A) and much improved the PK for 15w (FIG. 5B). In contrast to D6, the D2 derivative did not improve the PK of 15w (FIG. 5B).

Example 5. In Vivo Effects of 15u in Castration-Refractory Prostate Cancer

Figure 6A:
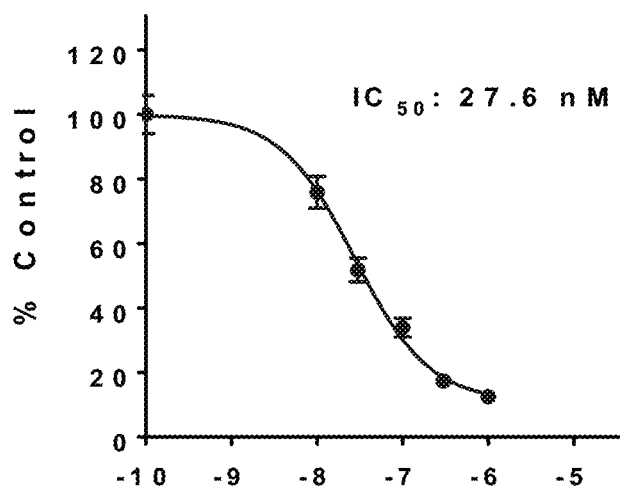
FIGS. 6A-6C shows the effects of different concentrations of thienopyridine derivatives 15u (FIG. 6A) and 15w (FIG. 6B) as well as Senexin B (FIG. 6C) on PSA expression in cell culture supernatant of a CRPC cell line C4-2.
Figure 6B:
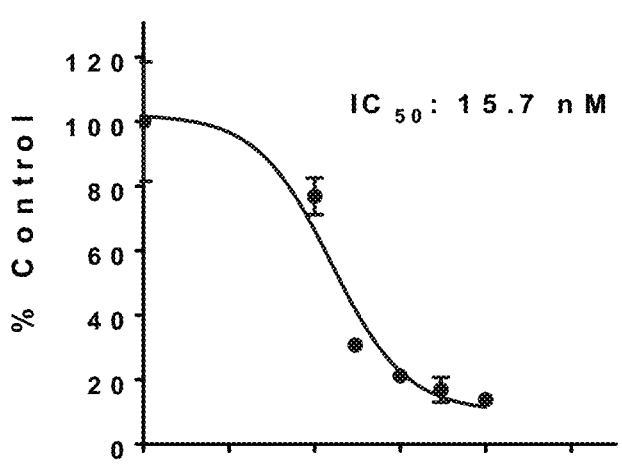
Figure 6C:
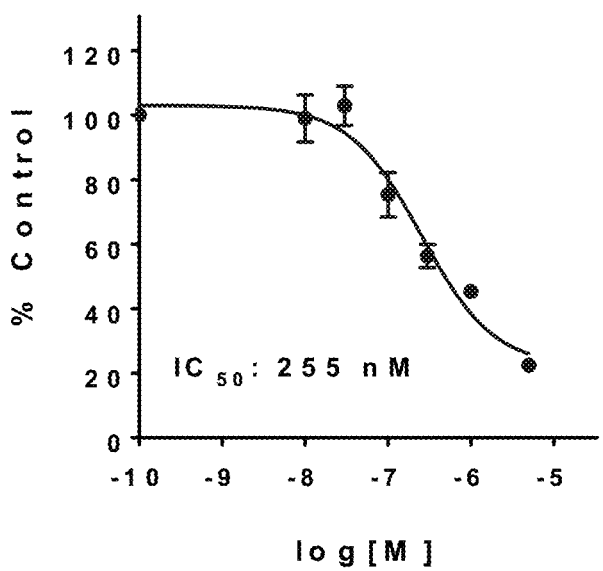

CDK8/19 inhibition decreases the expression of certain androgen-receptor (AR) inducible genes including PSA, the most common marker of prostate cancer, and the growth of castration-refractory prostate cancers (CRPC). FIGS. 6A-6C show the effects of different concentrations of three CDK8/19 inhibitors, thienopyridine derivatives 15u and 15w, and Senexin B, on PSA expression in cell culture supernatant of a CRPC cell line C4-2 after 4-day treatment in FBS-supplemented regular media. All 3 inhibitors suppressed PSA expression, with IC50 values of 27.6 nM for 15u, 15.7 nM for 15w, and 255 nM for Senexin B.

The in vivo effect of a mixture of 15u and 15w (the same mixture used for PK studies in Example 3), on PSA expression by C4-2 cells was analyzed after treatment of male NSG mice bearing C4-2 xenografts (grouped based on initial serum PSA level) for 4 days at 30 mg/kg administered orally daily for 4 days. Both the PSA protein levels in the serum and PSA mRNA levels in the tumor were strongly decreased by treatment with the mixture of 15u and 15w (FIGS. 6D-6F). Given the drastically different PK of 15u and 15w (Example 3), it appears likely that the effect on PSA was mediated by 15u.

In another in vivo study, CRPC cell line 22rv1 was grown as a xenograft in castrated male nude mice. When the tumors reached average size of 150~200 mm³, mice were randomized into two groups (n=13) and treated either with vehicle (0.5% carboxylmethyl cellulose) control or with 50 mg/kg 15u, given orally daily. As shown in FIG. 7A, 15u treatment strongly suppressed the tumor growth, as also demonstrated by the weight of tumors at the end of the study (FIG. 7B). Notably, 15u treatment showed no apparent adverse effects and no diminution of mouse body weight (FIG. 7C).

Example 6. Effects of 15u on Breast Cancer Metastasis

Figure 8A:
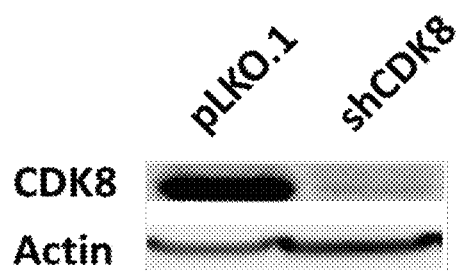
FIG. 8A shows immunoblotting analysis of CDK8 protein expression in murine 4T1 TNBC cells and their derivative expressing CDK8 shRNA.
Figure 8B:
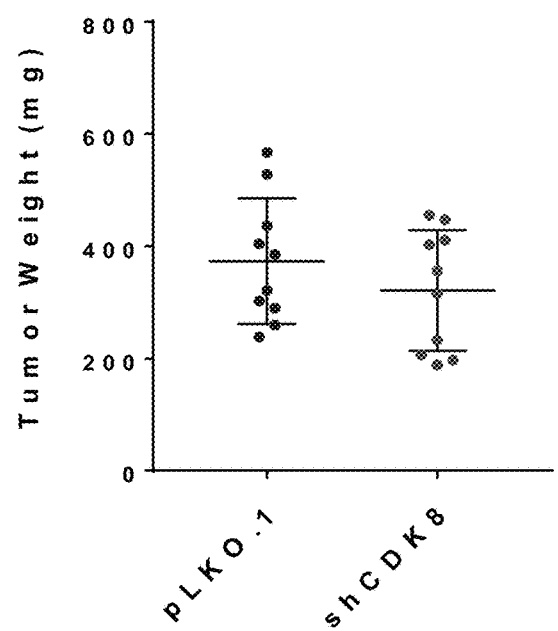
FIG. 8B shows the weights of the primary tumors formed by parental and CDK8 knockdown 4T1 cells.

4T1 is a murine triple-negative breast cancer (TNBC) cell line, which is highly metastatic to the lungs. The effect of CDK8 on lung metastasis in this model was demonstrated in the study shown in FIG. 8A-8C. CDK8-targeting shRNA was used to knock down CDK8 expression in 4T1 cells almost completely (FIG. 8A; these cells do not express detectable CDK19 protein). Parental and CDK8-knockdown 4T1 cells (n=10) were injected orthotopically in the mammary fat pad and the primary tumors were removed 17 days later. Following surgery, all the mice eventually died with lung metastases. The weights of the primary tumors showed no significant effect of CDK8 knockdown on tumor growth (FIG. 8B). However, the loss of CDK8 was associated with a strong increase in the survival of mice (FIG. 8C).

Figure 8C:
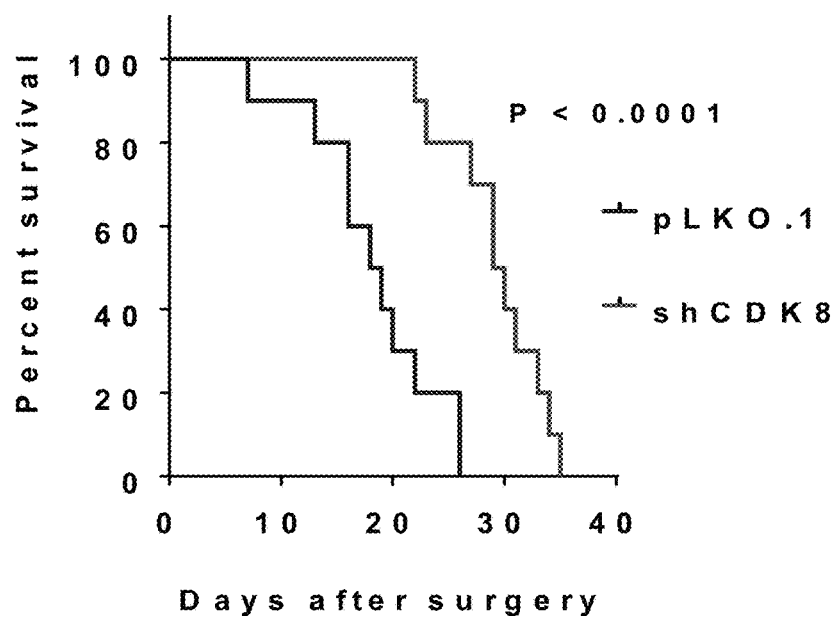
FIG. 8C shows the survival of mice after the removal of the primary tumors formed by parental and CDK8 knockdown 4T1 cells.
Figure 8D:
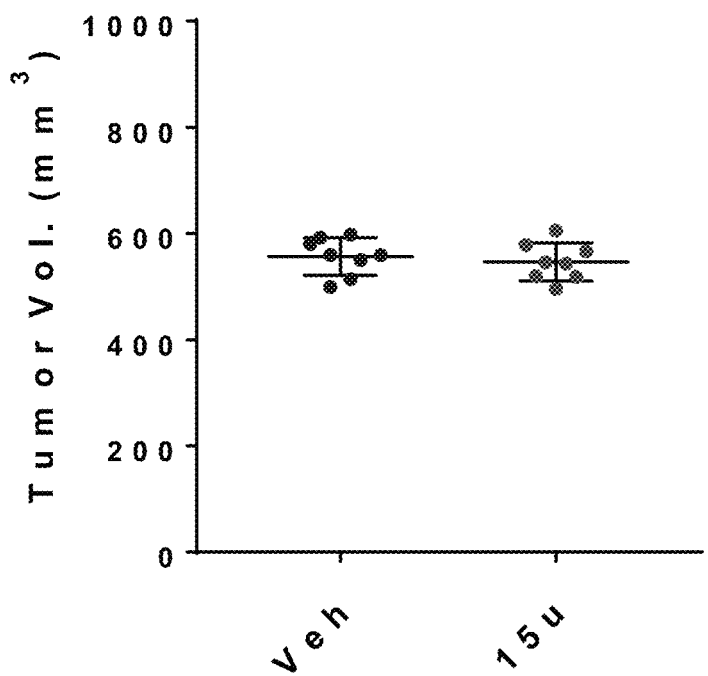
FIG. 8D shows primary tumor volume formed by parental 4T1 cells in the groups of mice that were subsequently treated with vehicle or 15u (25 mg/kg, bid).
Figure 8E:
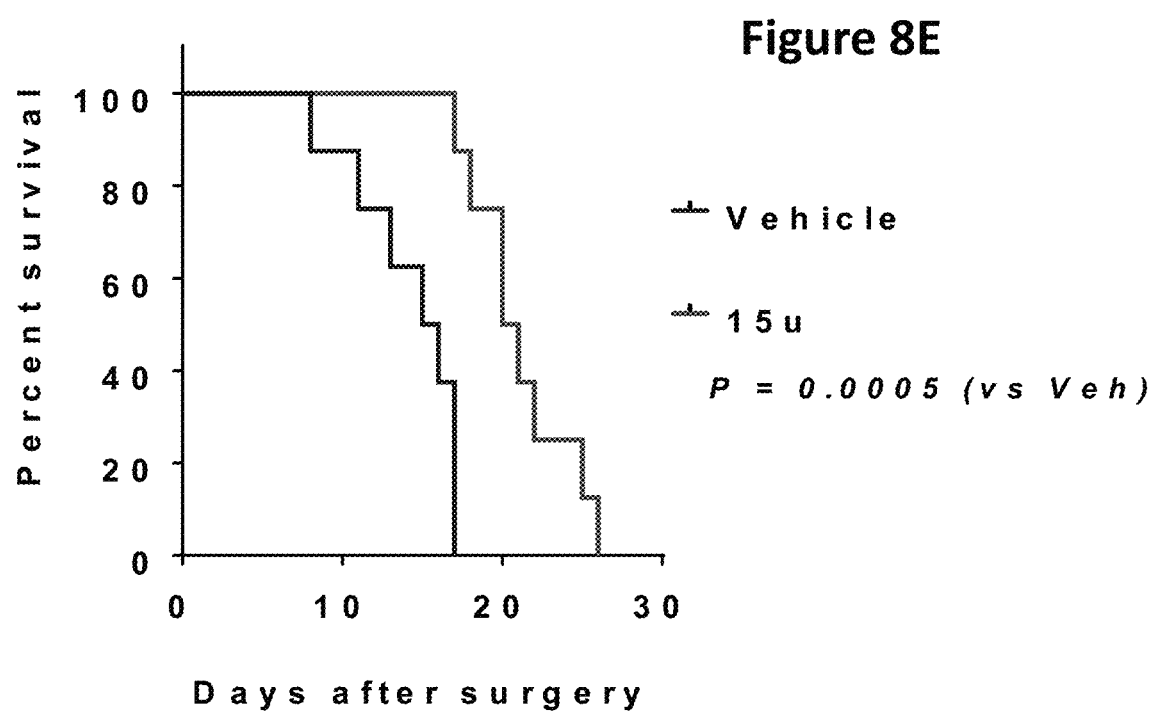
FIG. 8E shows the survival of mice treated with vehicle or 15u (25 mg/kg, bid) after the removal of the primary tumors.

In a similar study, following the removal of the primary tumor, mice were separated into three groups (FIG. 8D, n=8), which were then treated with vehicle (5% dextrose) or 15u (25 mg/kg, in 5% carboxylmethyl cellulose, oral, b.i.d.). 15u significantly increased mouse survival of the metastatic disease (FIG. 8E), with the effect similar to that of the CDK8 knockdown (FIG. 8C).

Figure 8F:
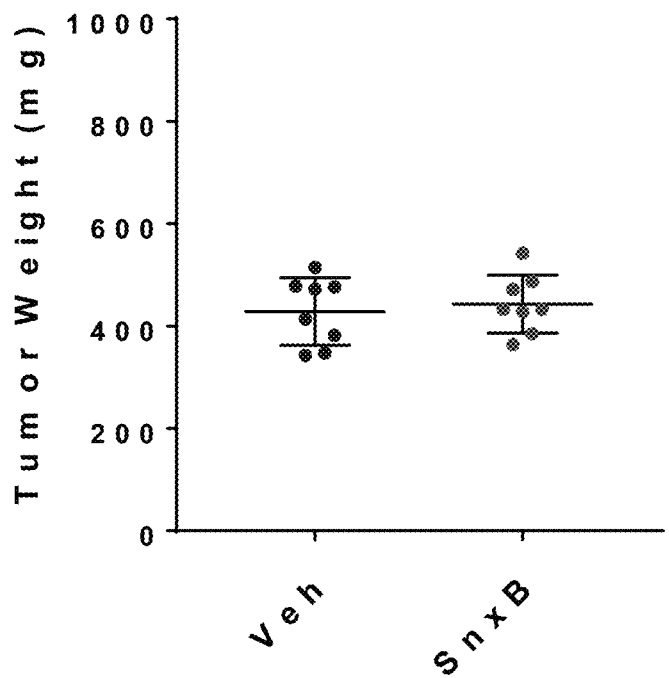
FIG. 8F shows primary tumor weights formed by parental 4T1 cells in the groups of mice that were subsequently treated with vehicle or Senexin B (50 mg/kg qd+350 ppm SnxB-medicated chow).
Figure 8G:
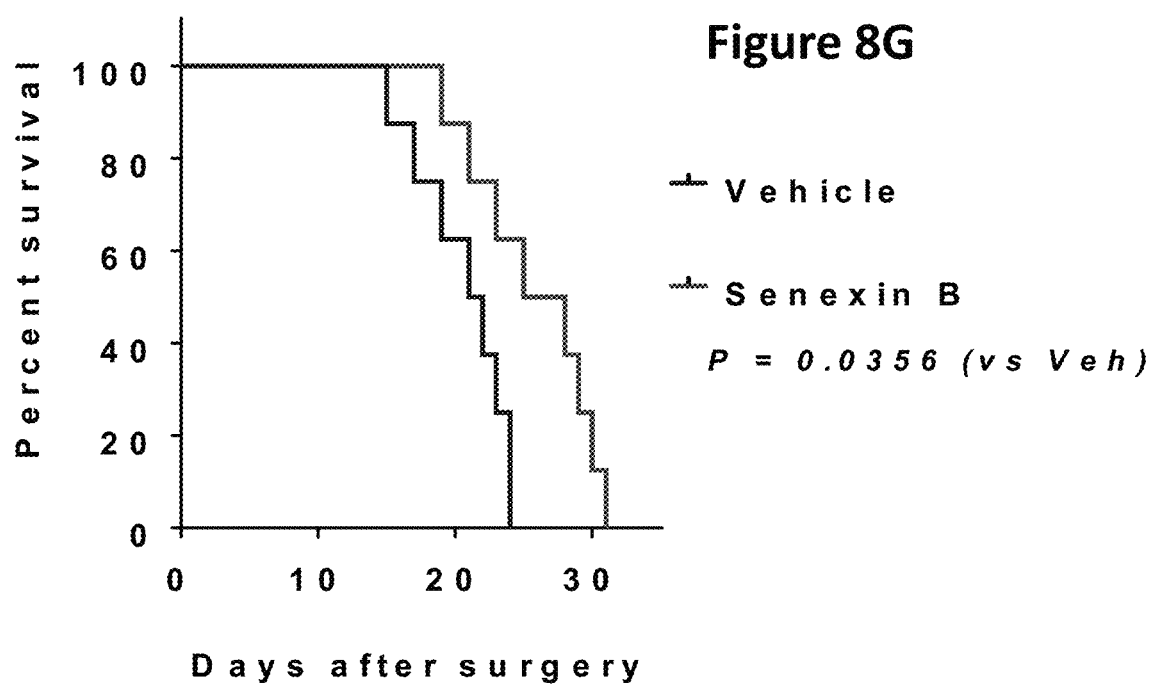
FIG. 8G shows the survival of mice treated with vehicle or Senexin B (50 mg/kg qd+350 ppm SnxB-medicated chow) after the removal of the primary tumors.

In another study with this model, tumors formed by parental 4T1 cells were removed and mice were randomized into two groups (FIG. 8F, n=8), treated with Senexin B (administered in medicated food (350 ppm) in combination with one oral dose 50 mg/kg as described in (Liang, 2018)) or receiving control food and vehicle. Senexin B treatment provided a statistically significant but moderate increase in survival (FIG. 8G).

In summary, the favorable PK of 15u (Example 3) and its in vivo activities (Examples 4,5), together with its favorable kinome profile (Example 2) indicate that 15u is an effective CDK8/19 inhibitor and composition for use in the treatment of cancers linked to CDK8/19 activity.

Figure 9A:
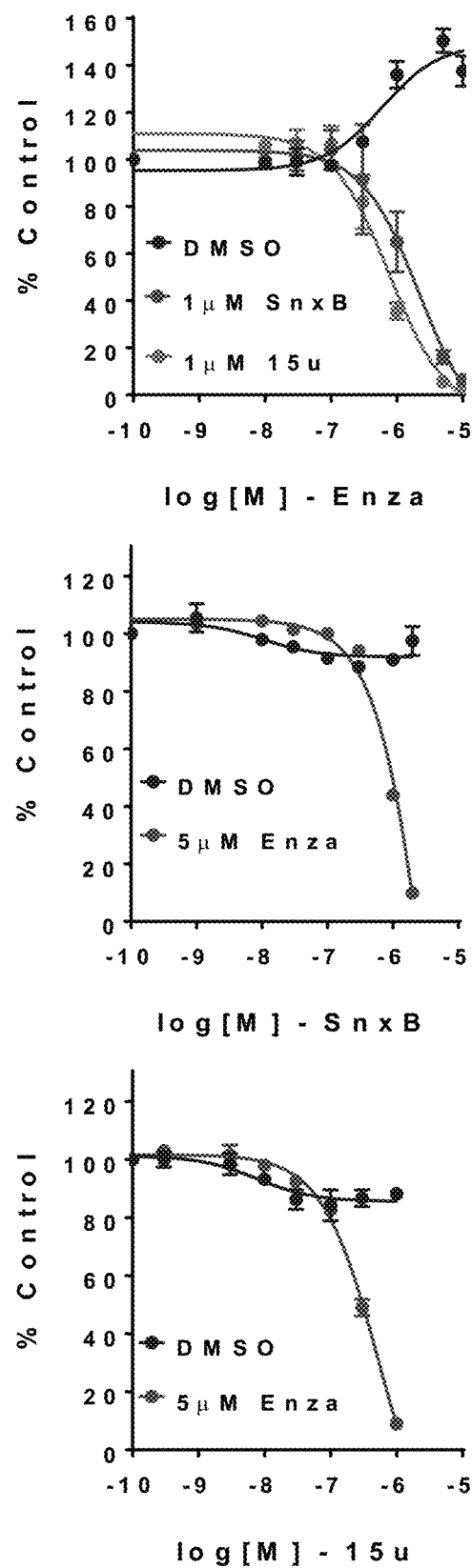
FIG. 9A examines the effect of the combination of either Senexin B (SnxB) or 15u with enzalutamide (Enza) on MYC-CAP-CR cell growth in androgen-containing media. The top panel shows effect on cell growth as a function of the Enza concentration. The middle panel shows the effect on cell growth as a function of concentration of SnxB. The lower panel shows the effect on cell growth as a function of 15u concentration.
Figure 9B:
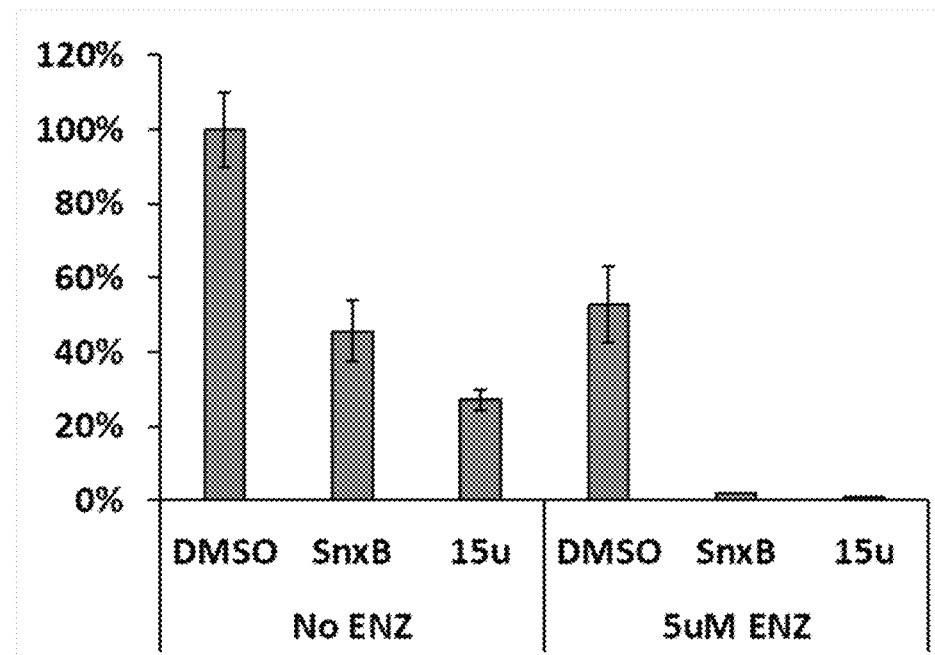
FIG. 9B shows the results of clonogenic assays comparing the effects of treatment with DMSO, 1 μM Senexin B (SnxB), 1 μM 15u, 5 μM enzalutamide (Enza)), a combination of 1 μM Senexin B and 5 μM enzalutamide (Enza), and a combination of 1 μM 15u and 5 μM enzalutamide (Enza).
Figure 9C:
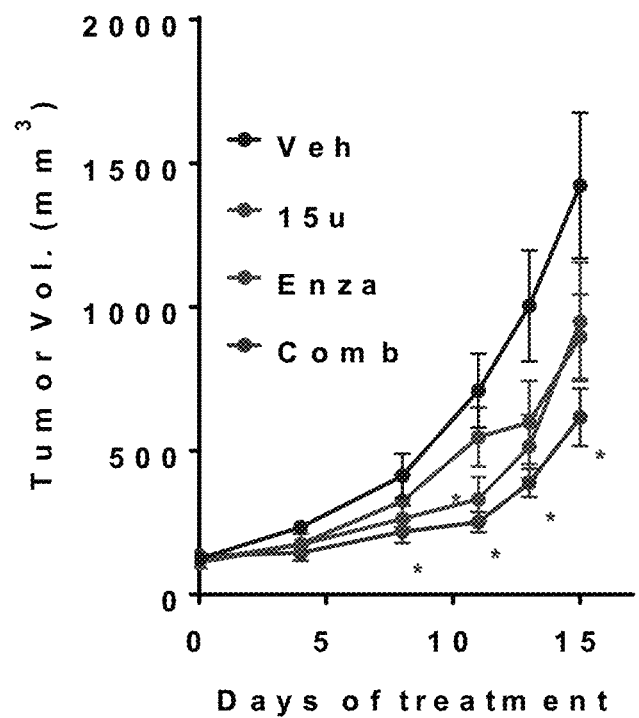
FIGS. 9C and 9D compare the volume (FIG. 9C) and weight (FIG. 9D) of MYC-CaP-CR tumors growing subcutaneously in intact (uncastrated) FVB male mice during treatment with vehicle (veh), 15u, enzalutamide (Enza), or a combination of 15u and enzalutamide (Comb).
Figure 9D:
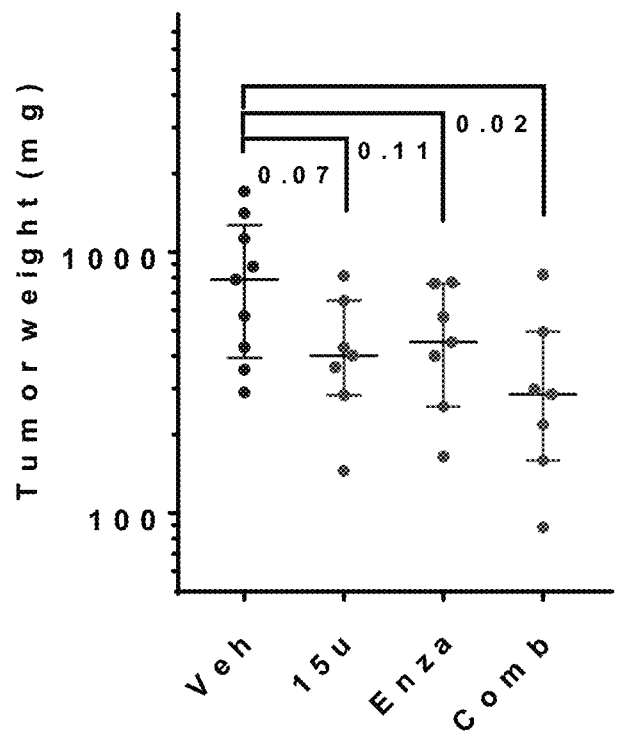

Example 7. In Vivo Effects of Treatment with Combined 15u and Enzalutamide in Castration-Refractory Prostate Cancer The combinatorial effects of 15u and anti-androgen enzalutamide in CRPC were analyzed in a murine MYC-Cap-CR model. MYC-CaP-CR cells (Ellis L. et al., 2012. Prostate 72(6):587-591) were selected for castration resistance from genetically engineered MYC-CaP cells that express MYC from an AR-responsive promoter (Watson P A, et al., 2005. Cancer Res 65(24):11565-11571). Castration resistance in these cells is associated with the overexpression of full-length AR rather than an AR variant, such as AR-V7 in 22rv1 (Olson B M, et al., 2017. Cancer immunology research 5(12):1074-1085). In a short-term cell proliferation assay, CDK8/19 inhibitors Senexin B and 15u showed little effect on MYC-CAP-CR cell growth in androgen-containing media, whereas enzalutamide paradoxically stimulated the growth of these cells (FIG. 9A). However, when enzalutamide was combined with either CDK8/19 inhibitor, MYC-CAP-CR cell growth was strongly inhibited (FIG. 9A), indicating that CDK8/19 inhibition may overcome enzalutamide resistance. In a long-term clonogenic assay, both Enzalutamide and CDK8/19 inhibitors decreased MYC-CaP-CR colony formation, and their combination produced an apparently synergistic effect (FIG. 9B). In vivo effects of 15u in combination with enzalutamide were tested in MYC-CaP-CR tumors growing subcutaneously in intact (uncastrated) FVB male mice. Both enzalutamide and 15u alone had a modest effect on tumor volume (FIG. 9C) and weight (FIG. 9D) when used alone, but their combination produced significant (p=0.02) tumor suppression.

These results suggest that 15u can be advantageously combined with enzalutamide (or other anti-androgens) in the treatment of CRPC. The strongest in vivo activity of 15u as a single agent in CRPC was observed in 22rv1 cells expressing AR-V7, suggesting that prostate cancers expressing AR-V7 and possibly other androgen-independent AR variants may be especially susceptible to CDK8/19 inhibition in vivo.

Example 8. Anti-Leukemic Effects of Thienopyridine Derivatives

Figure 10A:
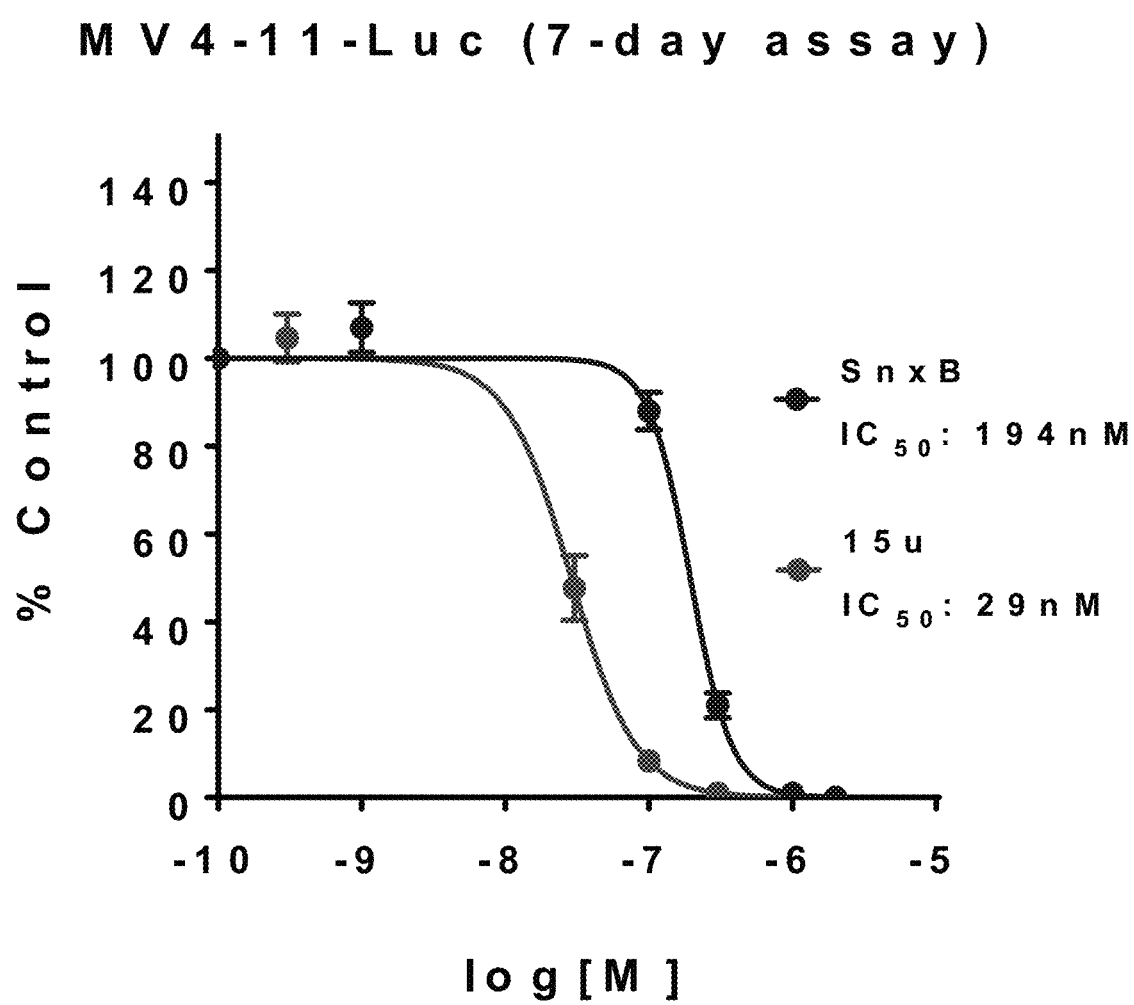
FIG. 10A shows the effect of various concentrations of 15u and Senexin B on the growth of luciferase-expressing MV4-11 cells, as detected by bioluminescence imaging.

The anti-leukemic properties of 15u were investigated in an acute myeloid leukemia (AML) cell line MV4-11, previously shown to be sensitive to CDK8/19 inhibition in vitro and in vivo (Pelish H E, et al., 2015. Nature 526(7572):273-276). The population of MV4-11 cells used for in vivo studies was made to express Luciferase and ZsGreen by lenviral infection with pHIV-Luc-ZsGreen, to enable leukemia growth analysis by bioluminescence imaging (BLI). The initial Luciferase-ZsGreen transduced cell population was sorted for ZsGreen positivity with fluorescence activated cell sorting. This MV4-11 cell population was tested for sensitivity to 15u. 15u strongly inhibited MV4-11 proliferation, and was deemed anti-proliferative with an IC50 value of 25 nM (FIG. 10A).

Assay protocol. For in vivo studies, 7-week-old female NSG mice (Jackson Laboratories) were injected with $2 \times 10^6$ luciferase-expressing MV4-11 cells in the tail vein. Following engraftment, BLI was performed on the inoculated mice 5 days after cell inoculation. After BLI, the mice were sorted into two matching cohorts of 10 mice and one cohort of 5 mice. BLI detection was done with IVIS Lumina II Series Hardware for In-Vivo Imaging with optional XFOV lens and Living Image software. The IVIS setting for sorting mice into cohorts was set for high sensitivity: Bin 8, F1.2, 180 sec. Subsequent exposures (week 1-5) were set for increased resolution: Bin 4, F1.2, 120 sec.

Figure 10B:
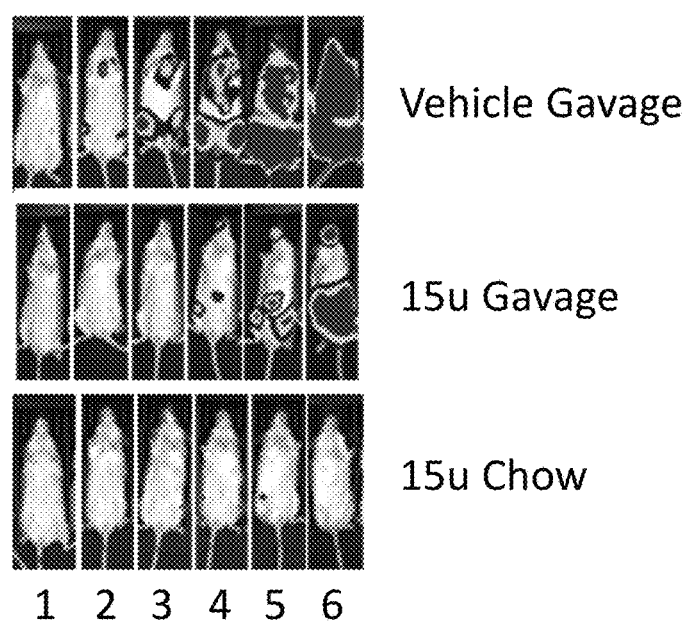
FIGS. 10B-10D compares tumor growth in mice injected with 2×10$^6$ luciferase-expressing MV4-11 cells following treatment with vehicle by gavage, 30 mg/kg of 15u suspended in vehicle by gavage twice a day, and medicated chow containing 15u at 1 g/kg.
Figure 10C:
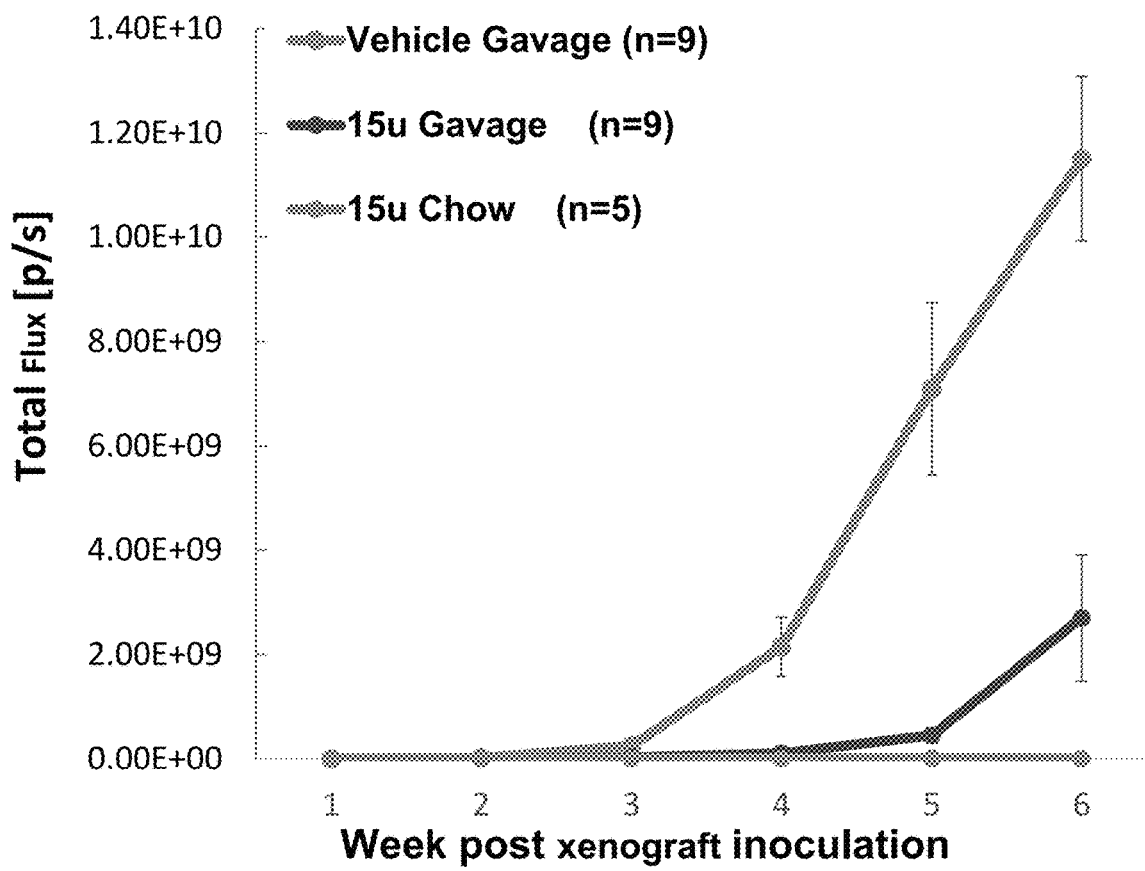

Treatment was initiated on day 6 following cell-inoculation and continued for 23 days. Ten mice received Vehicle only (5% carboxylmethyl cellulose) by gavage (200 μl). Ten mice received 30 mg/kg 15u suspended in the Vehicle twice daily by gavage (200 μl). 5 mice were treated with medicated food (chow) containing 15u at 1 g/kg in a custom Teklad diet prepared by Envigo (Madison, Wis.). This diet matches the diet used for normal mouse feeding, with the exception of added dye and 15u. The control MV4-11 xenografted mice (Vehicle) developed a vigorous tumor population as detected by BLI (FIG. 10B-10C). The 15u gavage treatment group shows a remarkable response with a 94% growth inhibition of leukemia growth, p=0.001. The 15u chow treatment group shows an even more remarkable leukemia suppression with a 99.7% inhibition of leukemia growth, p=0.002. Survival of the mice post treatment was monitored.

Figure 10D:
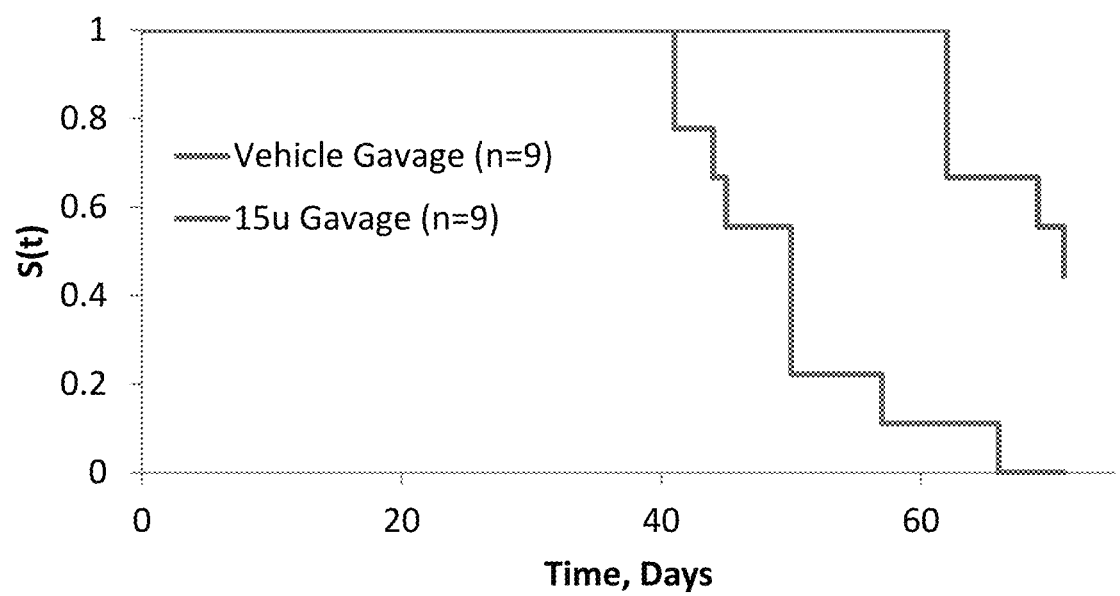

Results. As shown in FIG. 10D, mice treated with 15u by oral gavage demonstrated superior survival rates.

Figure 11A:
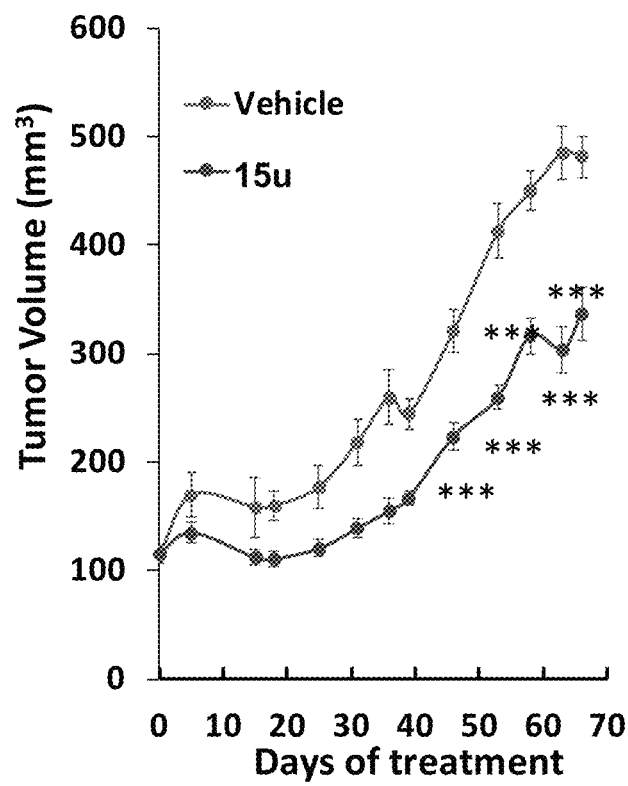
Figure 11B:
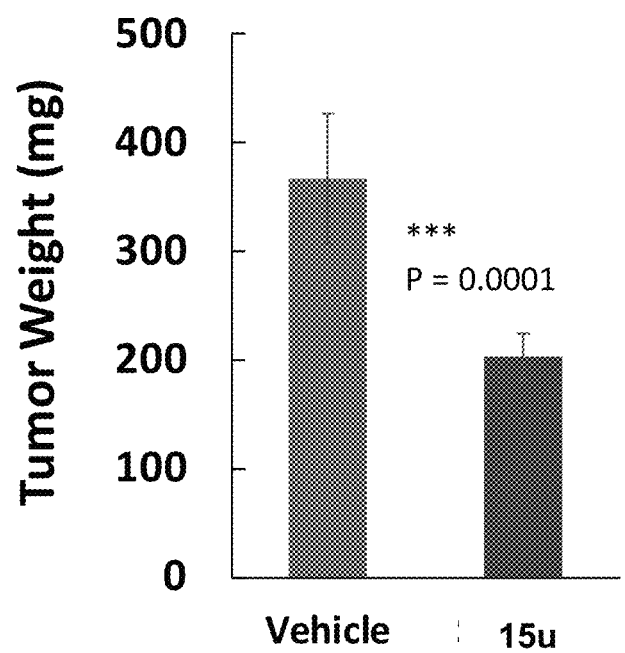

Example 9. Effect of 15u on In Vivo Growth of MDA-MB-468 Triple-Negative Breast Cancer (TNBC) Xenografts Human MDA-MB-468 triple-negative breast cancer (TNBC) cells were found to be responsive to 15u and other CDK8/19 inhibitors upon long-term treatment in vitro. To evaluate the effect of CDK8/19 inhibition on in vivo growth of MDA-MB-468 xenografts, 1 million cells with 40% Matrigel (100 ml total volume) were injected s.c. into the right flanks of immunodeficient NSG female mice (9 weeks old). 11 days after inoculation, mice were randomized by tumor size into two groups (n=9), with the average tumor volume 115 mm$^3$ in each group. Mice in the first group (control) received regular diet and mice in the second group (treatment) received medicated diet containing 250 ppm 15u. 13 days after the start of treatment, medicated diet was supplemented with daily oral gavage providing 5 mg/kg 15u solution in the treatment group or with vehicle alone (control group). 37 days after the start of treatment, the gavage dose in the treatment group was increased to 8 mg/kg; treatment was continued for a total of 66 days. Tumor volumes were measured with calipers twice a week (FIG. 11A), showing a significant reduction in tumor volume in the 15u treatment group. At the end of the study, mice were euthanized, tumors dissected and weighed; tumor weights were significantly lower in the 15u treatment group (FIG. 11B). Mouse body weights (FIG. 11C) showed no detrimental effects of long-term 15u treatment.

Example 10. Determination of Maximum Tolerated Dose (MTD) of 15u in CD-1 Mice

Figure 12A:
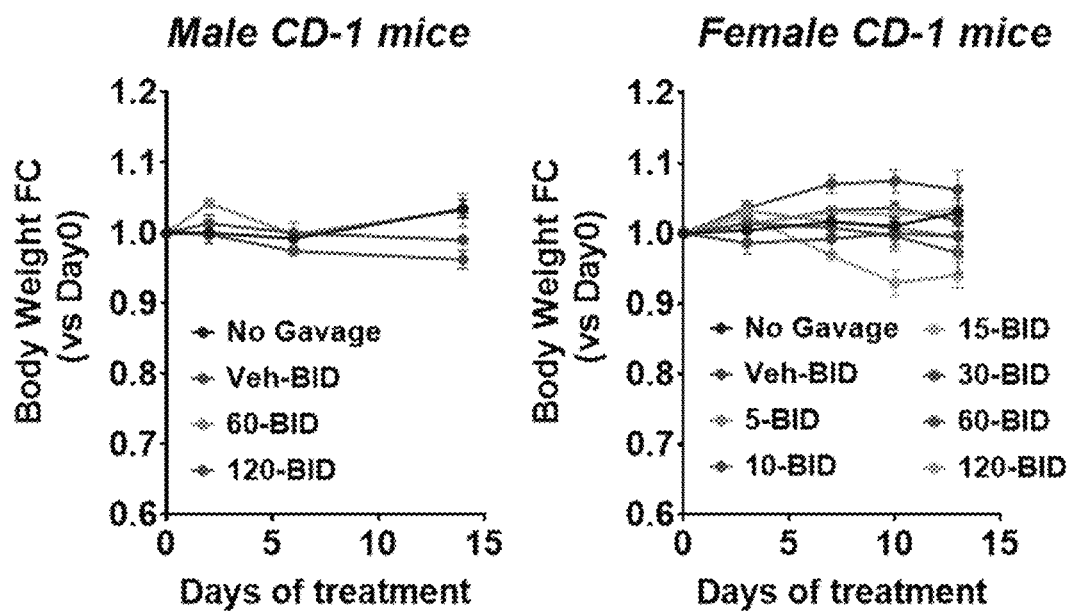
FIGS. 12A and 12B demonstrate the maximum tolerated dose (MTD) of 15u in CD-1 mice.

To determine the maximum tolerated dose (MTD), 8-week-old male or female CD-1 mice were randomly assigned to different dose groups and treated with 15u at escalating doses through either oral gavage in solution or medicated food. In one MTD in vivo study, female CD-1 mice were treated with gavage twice a day (b.i.d.) providing 5, 10, 15, 30, 60 or 120 mg/kg of 15u and male CD-1 mice were treated with gavage b.i.d. providing 60 or 120 mg/kg for 14 days. No detrimental effects were observed in male mice of any treated groups (60 and 120 mg/kg b.i.d.) and female mice of the groups treated with 15u at doses up to 60 mg/kg b.i.d. (FIG. 12A). The highest dose (120 mg/kg b.i.d.) caused about 10% body weight loss in female mice after 7-10 days of treatment but no further deterioration was observed through the rest of the treatment period (FIG. 12A).

Figure 12B:
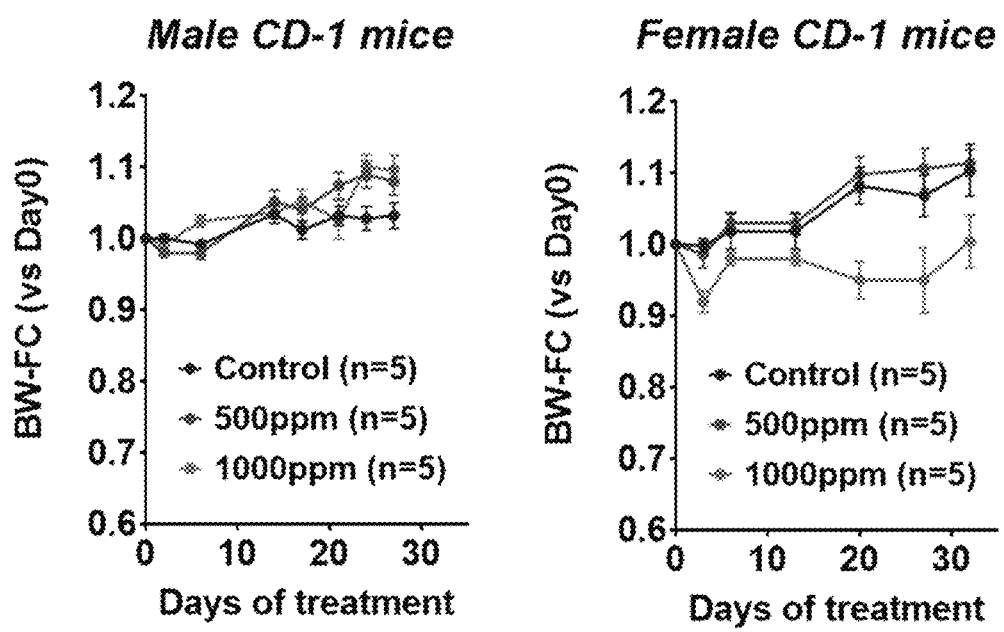

In another long-term MTD in vivo assay, groups of male and female CD-1 mice were fed regular diet (control) or 15u-medicated diet (500 ppm or 1000 ppm) for 4 or 5 weeks (FIG. 12B). The daily doses of 500 ppm and 1000 ppm groups were estimated to be about 50-100 mg/kg and 100-200 mg/kg, respectively, based on daily diet consumption. Only the highest dose (1000 ppm) caused significant weight loss (5-10%) in female mice during the first week while no further detrimental effects were observed for the rest of the treatment period.

Considering that maximal therapeutic effects can be achieved at 30 mg/kg daily dose in various mouse xenograft models, these two MTD assays suggested a high therapeutic index for 15u.

Example 11. In Silico Modeling of Thienopyridine and Pyrrolopyridine Binding to CDK8

A docking model for compounds 15u, 15w, 15w_APP, 15_PP, and 15u_CN binding to CDK8 was generated using Schrodinger Induced Fit docking. The Induced Fit protocol docks an active ligand with Glide and then to generate a diverse ensemble of ligand poses, the procedure uses reduced van der Waals radii and an increased Coulomb-vdW cutoff, to temporarily remove highly flexible side chains during the docking step. For each pose, a Prime structure prediction is then used to accommodate the ligand by reorienting nearby side chains. These residues and the ligand are then minimized. Finally, each ligand is re-docked into its corresponding low energy protein structures and the resulting complexes are ranked according to GlideScore. This model was used to guide the design of the following predicted novel structures.

Figure 13:
FIG. 13 shows the binding modes of 15u, 15w, 15w_APP, 15w_PP, 15w_CN with CDK8 overlaid.

FIG. 13 displays an overlay of the binding modes of 15u, 15w, 15w_APP, 15w_PP, 15w_CN with CDK8. The results indicate the similarly in binding between the different thienopyridines and pyrrolopyridines. Comparison of 15u and 15w to 15w_APP indicates that the —NH— group replacing the sulfur does not alter the binding mode. In addition, 15w_App and provides an extra H-bond donor to the hinge region of CDK8. The PP compounds display similar binding interactions to the APP analogs. The docking model predicts that —NH— provides an extra H-bond donor to the hinge region of CDK8 increasing potency while compensating for the loss of the 3-amino group. Comparison of 15u_CN to 15u and 15w suggests that the carbonitrile makes similar interactions to the amide.

Example 12. Structure Activity Relationship

Table 6 summarizes the structure activity relationship for compositions described herein. To determine the inhibition potency, the NFκB Activity Assay (HEK238-NFκB-Luc Assay) as described in Example 1 and the MV4-11 assay (MV4-11-Luc Assay) as described in Example 8. To determine the PK, eight to twelve-week-old female CD-1 mice were treated with tested inhibitors at indicated doses (15~30 mg/kg) through oral gavage in a solution formulation (10% N-Methyl-2-Pyrrolidone (NMP), 27% Propylene Glycol (PG), 63% polyethylene glycol 400 (PEG-400)). Blood samples (70~100 µL) were collected into BD Microtainer blood collection tubes for serum separation at different time points (1, 2, 6, 8 hours post administration) with heparinized microhematocrit capillary tubes from retro-orbital veins of anesthetized animals. Serum samples were processed for LCMSMS to determine drug concentration using compound-specific MRMs (15u: 439-394; 15u-D6: 445-394; 15w: 453-436; 15w-D2: 455-438; 15w-D6: 459-442; 6264: 483-394; 6300: 480-380; 6304: 453-408). Drug concentrations were plotted against time points to generate PK curves with GraphPad software and AUCs (area under the curve) within the first eight hours after dosing were calculated with Excel Software to compare PK profiles of different compounds.

TABLE 6

Structure activity relationships

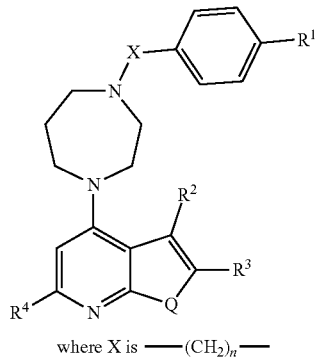

where X is —(CH$_2$)$_n$—

| Name | Q | R$^3$ | R$^2$ | n | R$^1$ | R$_4$ | Inhibition Potency HEK238-NFkB-Luc Assay | Inhibition Potency MV4-11-Luc Assay | Oral PK dose | AUC (0-8 hr) |
|---|---|---|---|---|---|---|---|---|---|---|
| 15k | S | CONH$_2$ | NH$_2$ | 0 | H | H | 50.6 nM | | | |
| 15n | S | CONH$_2$ | NH$_2$ | 0 | CH$_3$ | H | 43.1 nM | | | |
| 15q | S | CONH$_2$ | NH$_2$ | 0 | OCH$_3$ | H | 37.8 nM | | | |
| 15u | S | CONH$_2$ | NH$_2$ | 0 | N,N-dimethylformamide | H | 10.3 nM | 30 nM | 30 mg/kg | 6.6 μg*hr/mL |
| 15u_D6 | S | CONH$_2$ | NH$_2$ | 0 | N,N-bis(methyl-d3) formamide | H | 7.7 nM | | 30 mg/kg | 7.4 μg*hr/mL |
| 15v | S | CONH$_2$ | NH$_2$ | 0 | N-methylformamide | H | 23.1 nM | | | |
| 15w | S | CONH$_2$ | NH$_2$ | 0 | N,N-dimethylacetamide | H | 4.1 nM | | 16 mg/kg | 0.40 μg*hr/mL |
| 15w_D2 | S | CONH$_2$ | NH$_2$ | 0 | N,N-dimethyl-acetamide-2,2-d2 | H | 8.8 nM | | 18 mg/kg | 0.38 μg*hr/mL |

TABLE 6-continued

Structure activity relationships

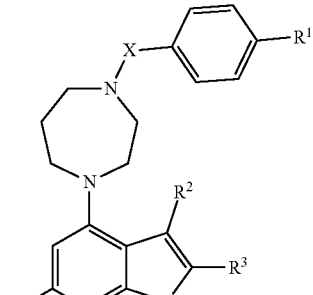

where X is —(CH$_2$)$_n$—

| | | | | | | | Inhibition Potency | | Oral | |
|---|---|---|---|---|---|---|---|---|---|---|
| Name | Q | R$^3$ | R$^2$ | n | R$^1$ | R$_4$ | HEK238-NFkB-Luc Assay | MV4-11-Luc Assay | PK dose | AUC (0-8 hr) |
| 15w_D6 | S | CONH$_2$ | NH$_2$ | 0 | 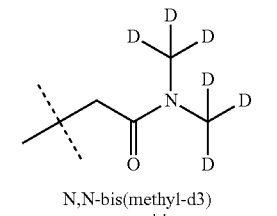 N,N-bis(methyl-d3) acetamide | H | 3.8 nM | | 16 mg/kg | 0.77 µg*hr/mL |
| 6263 | S | CONH$_2$ | NH$_2$ | 0 | 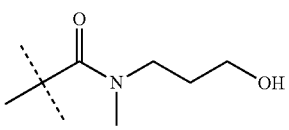 N-(3-hydroxypropyl)formamide | H | 169 nM | 83 nM | | |
| 6264 | S | CONH$_2$ | NH$_2$ | 0 | N-(3-hydroxypropyl)-N-methylformamide | H | 37 nM | 31 nM | 25 mg/kg | 0.47 µg*hr/mL |
| 6293 | S | CONH$_2$ | NH$_2$ | 0 | 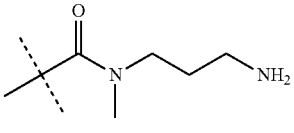 N-(3-aminopropyl)-N-methylformamide | H | 50 nM | | | |
| 6292 | S | CONH$_2$ | NH$_2$ | 0 | 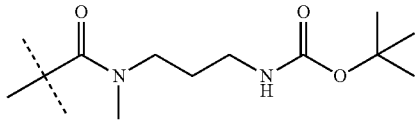 tert-butyl (3-(N-methylformamido)propyl)carbamate | H | 594 nM | | | |

TABLE 6-continued

Structure activity relationships

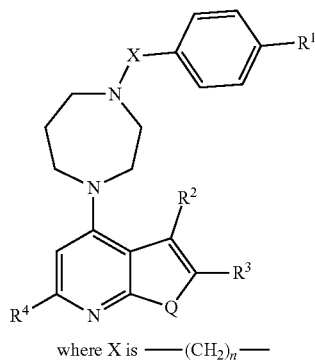

where X is —(CH$_2$)$_n$—

| Name | Q | R$^3$ | R$^2$ | n | R$^1$ | R$_4$ | Inhibition Potency HEK238-NFkB-Luc Assay | MV4-11-Luc Assay | Oral PK dose | AUC (0-8 hr) |
|---|---|---|---|---|---|---|---|---|---|---|
| 6300 | S | CONH$_2$ | NH$_2$ | 0 | (4-methylpiperazin-1-yl)methylene | H | 4.9 nM | | 30 mg/kg | 0.21 μg*hr/mL |
| 6268 | S | CONH$_2$ | NH$_2$ | 0 | 4-methylpiperazine-1-carbaldehyde | H | 31 nM | 42 nM | | |
| 6269 | S | CONH$_2$ | NH$_2$ | 1 | N,N-dimethyl-formamide | H | 1 uM | 683 nM | | |
| 6270 | S | CONH$_2$ | NH$_2$ | 0 | tert-butyl 4-formylpiperazine-1-carboxylate | H | | 40 nM | | |
| 6271 | S | CONH$_2$ | NH$_2$ | 0 | piperazine-1-carbaldehyde | H | 233 nM | 79 nM | | |

TABLE 6-continued

Structure activity relationships where X is —(CH$_2$)$_n$—

| Name | Q | R³ | R² | n | R¹ | R₄ | Inhibition Potency HEK238-NFkB- Luc Assay | MV4-11- Luc Assay | Oral PK dose | AUC (0-8 hr) |
|------|---|-----|-----|---|-----|-----|--------|--------|--------|--------|
| 6296 | S | CONH$_2$ | H | 0 | N,N-dimethylformamide | H | >1000 nM | | | |
| 6284 | N | CONH$_2$ | H | 0 | N,N-dimethylformamide | H | >1000 nM | | | |
| 6307 | N | CONH$_2$ | NH$_2$ | 0 | N,N-dimethylformamide | H | >1000 nM | | | |
| 6318 | O | CONH$_2$ | NH$_2$ | 0 | N,N-dimethylformamide | H | >1000 nM | | | |
| 6304 | S | CONH$_2$ | NH$_2$ | 0 | N,N-dimethylformamide | CH$_3$ | 13.6 nM | | 16 mg/kg | 2.2 μg*hr/mL |

TABLE 6-continued

Structure activity relationships

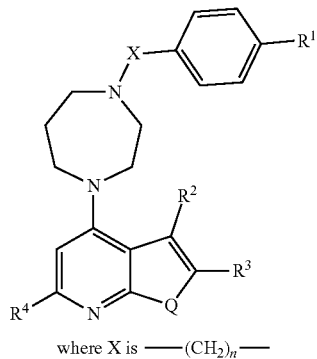

where X is —(CH$_2$)$_n$—

| Name | Q | R³ | R² | n | R¹ | R₄ | Inhibition Potency HEK238-NFkB- Luc Assay | MV4-11- Luc Assay | Oral PK dose | AUC (0-8 hr) |
|---|---|---|---|---|---|---|---|---|---|---|
| 6298 | S | CN | NH₂ | 0 | N,N-dimethylformamide | H | 379 nM | | | |

Example 13. Synthetic Schemes

Scheme 1 shows a general synthetic procedure for preparing compounds disclosed herein. Preparation of specific compounds is provided below.

Scheme 1. Small-scale synthesis of thyenopyridine derivatives.

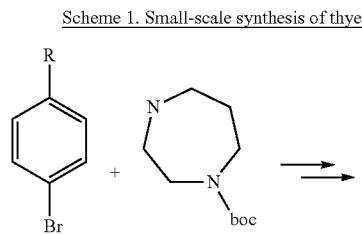

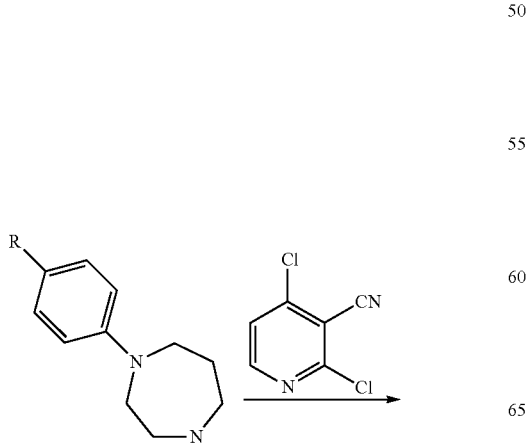

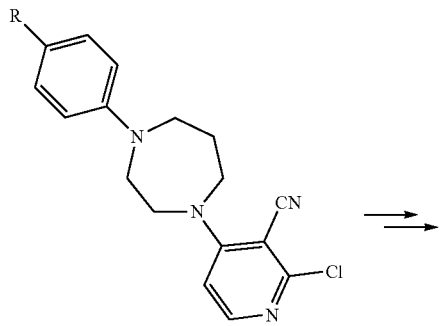

-continued

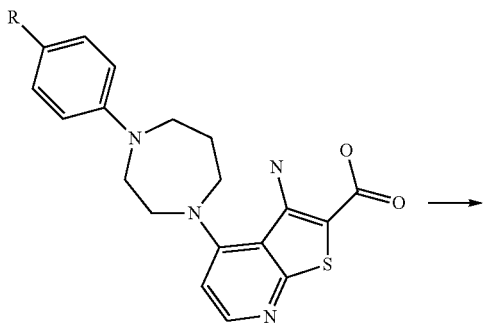

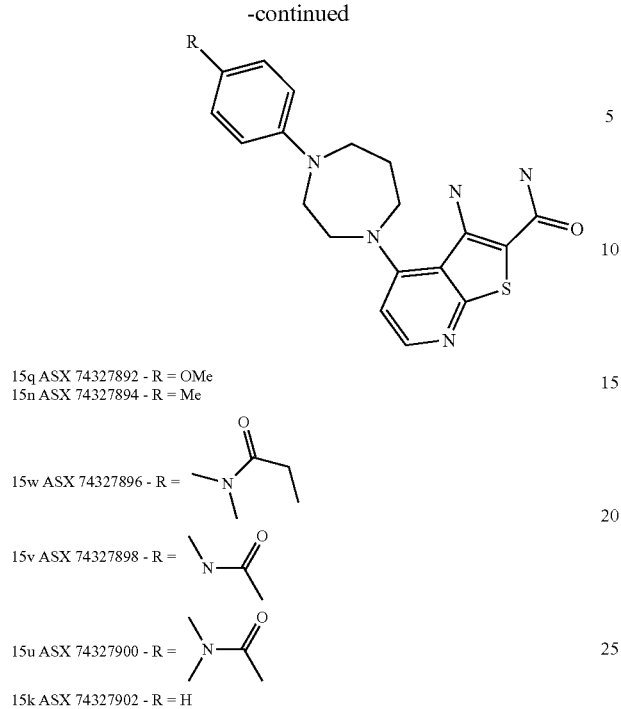

15q ASX 74327892 - R = OMe
15n ASX 74327894 - R = Me
15w ASX 74327896 - R =
15v ASX 74327898 - R =
15u ASX 74327900 - R =
15k ASX 74327902 - R = H

An alternative scheme for preparing the thienopyridine compounds is disclosed in Saito, K. et al., Bioorg Med Chem 2013, 21, 1628-42.

Scheme 2 shows a synthetic scheme for the preparation of pyrrolopyridines, such as 15u_PP. Those of skill in the art may alter Schemes 1 and 2 to prepare furopyridines.

Scheme 2. Synthesis of 15u_PP

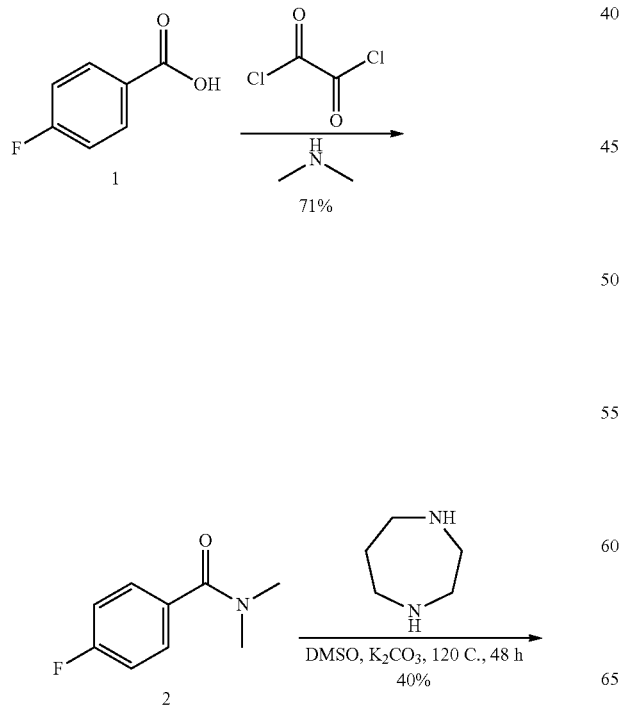

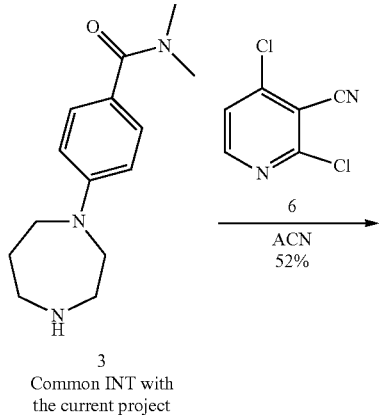

3
Common INT with
the current project

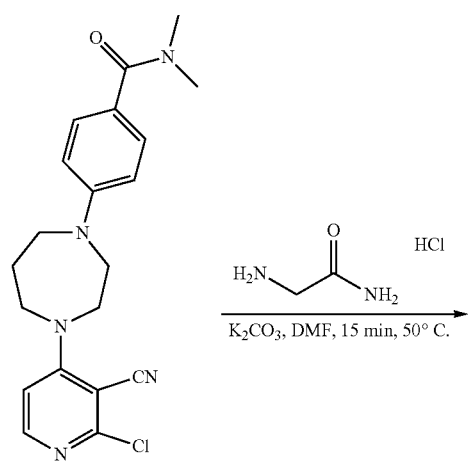

7

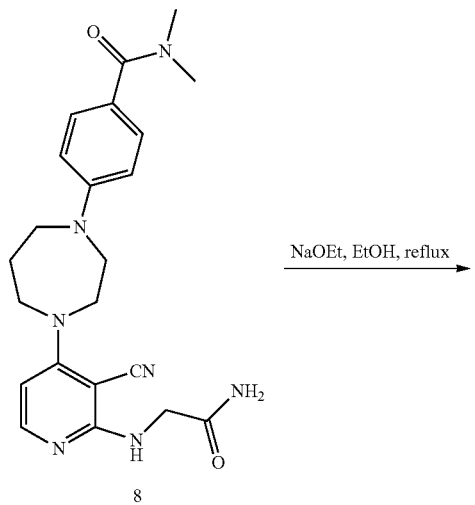

8

47
-continued

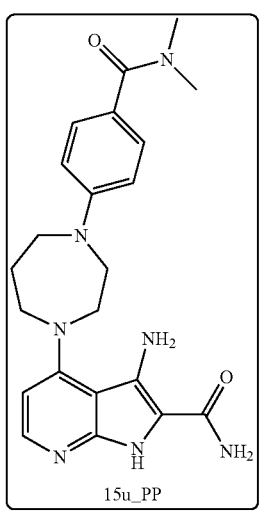

Synthesis of 3-amino-4-(4-(4-(2-(dimethylamino)-2-oxoethyl)phenyl)-1,4-diazepan-1-yl)thieno[2,3-b]pyridine-2-carboxamide (15w)

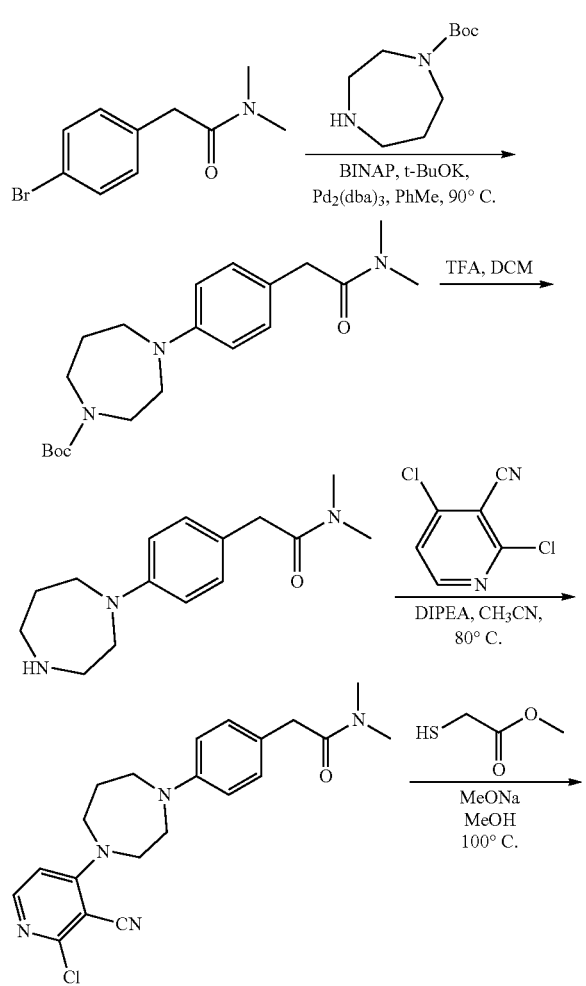

48
-continued

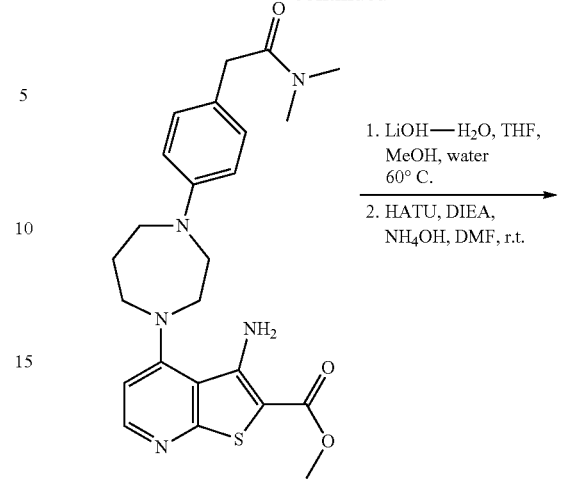

The solution of 2-(4-bromophenyl)-N,N-dimethyl-acetamide (1 eq) and tert-butyl 1,4-diazepane-1-carboxylate (1.2 eq) in t-BuOH and 1,4-dioxane was added with 2-Dicyclohexylphosphino-2'-(N,N-dimethylamino)biphenyl (0.15 eq), t-BuONa (1.4 eq) and Tris(dibenzylideneacetone)dipalladium (0.05 eq). The mixture was degassed and protected with nitrogen, then reflux for 1 h. After that, the mixture was cooled to r.t. and water was added, the mixture was extracted with EA, the organic layers were washed with brine and dried by $Na_2SO_4$, condensed and purified by flash column to get the tert-butyl 4-[4-[2-(dimethylamino)-2-oxo-ethyl]phenyl]-1,4-diazepane-1-carboxylate (yield 92%), ESI-MS m/z: 362 ([M+H]$^+$); the solution of tert-butyl 4-[4-[2-(dimethylamino)-2-oxo-ethyl]phenyl]-1,4-diazepane-1-carboxylate (1 eq) in DCM, then TFA (5 eq) was added and the mixture was stirred at r.t. for 3 h, after that, the mixture was condensed to remove the TFA and resulted the 2-(4-(1,4-diazepan-1-yl)phenyl)-N,N-dimethylacetamide which was used without further purification, ESI-MS m/z: 262 ([M+H]$^+$); the solution of 2-(4-(1,4-diazepan-1-yl)phenyl)-N,N-dimethylacetamide (1 eq) in acetonitrile was added with 2,4-dichloronicotinonitrile (1 eq) and DIPEA (2 eq). Then the mixture was stirred at 80° C. for overnight. After that, the mixture was cooled to r.t. and condensed, the mixture was then dissolved in DCM and water was added, the mixture was extracted with DCM, the organic layers were collected and washed with brine and dried by $Na_2SO_4$, condensed and purified by flash column to get the 2-(4-(4-(2-chloro-3-cyanopyridin-4-yl)-1,4-diazepan-1-yl)phenyl)-N,N-dimethylacetamide (yield 55%), ESI-MS m/z: 398 ([M+H]⁺); the solution of 2-(4-(4-(2-chloro-3-cyanopyridin-4-yl)-1,4-diazepan-1-yl)phenyl)-N,N-dimethylacetamide (1 eq) in MeOH was added with MeONa (2 eq) and methyl thioglycolate (2 eq), then the mixture was stirred at 100° C. for overnight. After that, the mixture was cooled to r.t. and condensed and purified by flash column to get the methyl 3-amino-4-(4-(4-(2-(dimethylamino)-2-oxoethyl)phenyl)-1,4-diazepan-1-yl)thieno[2,3-b]pyridine-2-carboxylate (yield 72%), ESI-MS m/z: 468 ([M+H]⁺); the solution of methyl 3-amino-4-(4-(4-(2-(dimethylamino)-2-oxoethyl)phenyl)-1,4-diazepan-1-yl)thieno[2,3-b]pyridine-2-carboxylate (1 eq) in THF and water, then LiOH (2 eq) was added and the mixture was stirred at 60° C. for overnight. After that, the mixture was cooled to r.t. and condensed and dissolved in DMF, then HATU (1.5 eq) and DIPEA (2 eq) were added and the mixture was stirred at r.t. for 15 min, then NH₄OH (6 eq) was added to the above mixture and stirred at r.t. for another 2 h. After that, water was added and the mixture was extracted with DCM, the organic layers were combined and dried by Na₂SO4, condensed and purified by flash column to get the 3-amino-4-(4-(4-(2-(dimethylamino)-2-oxoethyl)phenyl)-1,4-diazepan-1-yl)thieno[2,3-b]pyridine-2-carboxamide (yield 45%) as light yellow solid, ESI-MS m/z: 453 ([M+H]⁺).

Synthesis of 3-amino-4-(4-(4-(2-(bis(methyl-d3)amino)-2-oxoethyl)phenyl)-1,4-diazepan-1-yl)thieno[2,3-b]pyridine-2-carboxamide (15w_D6)

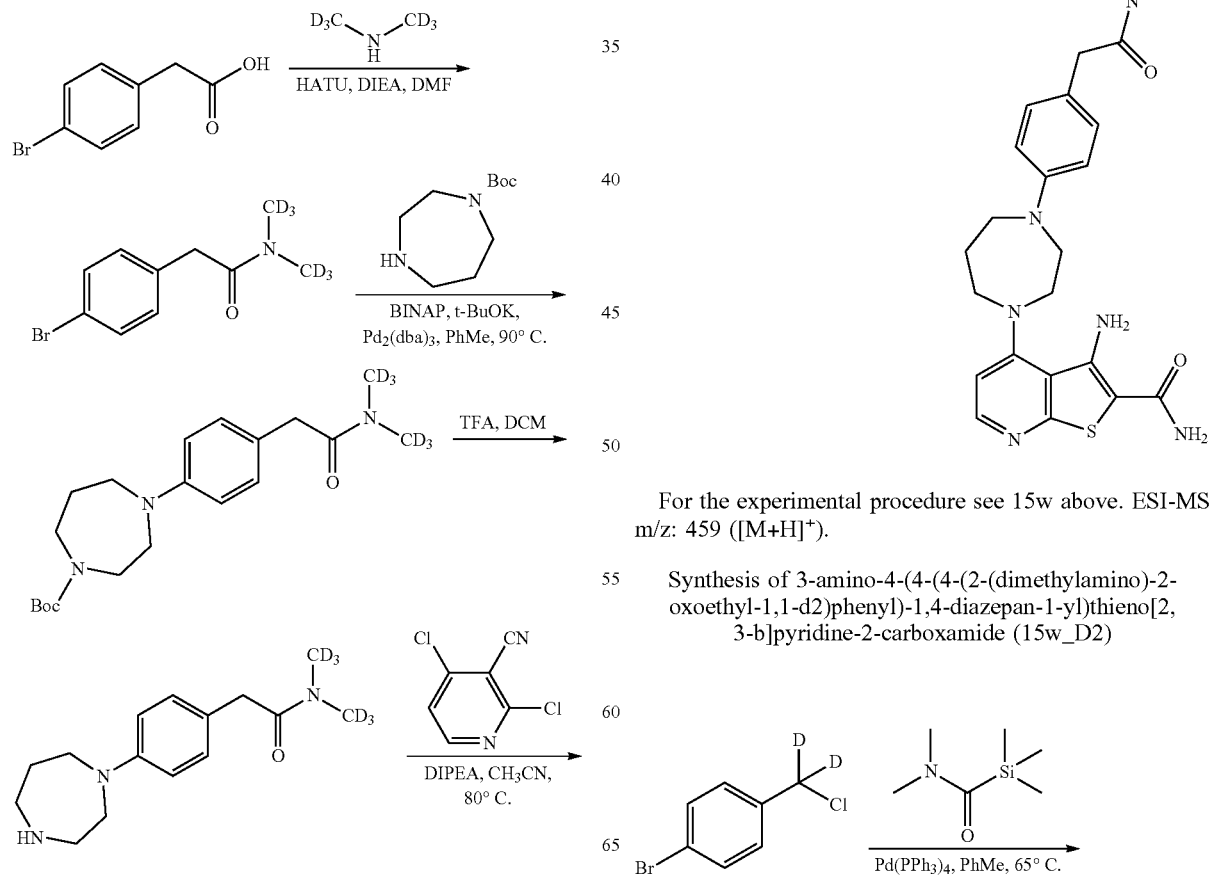

For the experimental procedure see 15w above. ESI-MS m/z: 459 ([M+H]⁺).

Synthesis of 3-amino-4-(4-(4-(2-(dimethylamino)-2-oxoethyl-1,1-d2)phenyl)-1,4-diazepan-1-yl)thieno[2,3-b]pyridine-2-carboxamide (15w_D2)

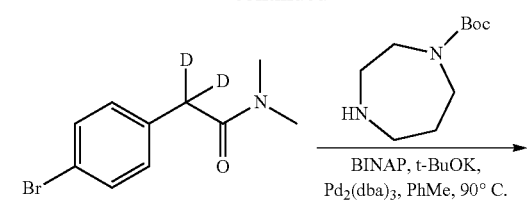
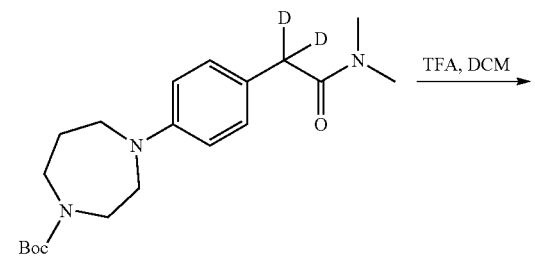
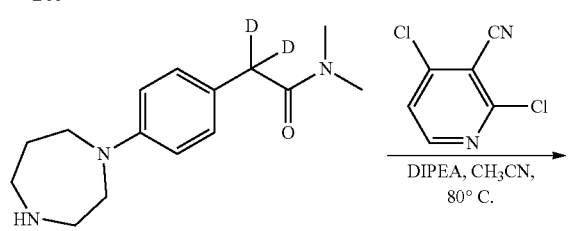
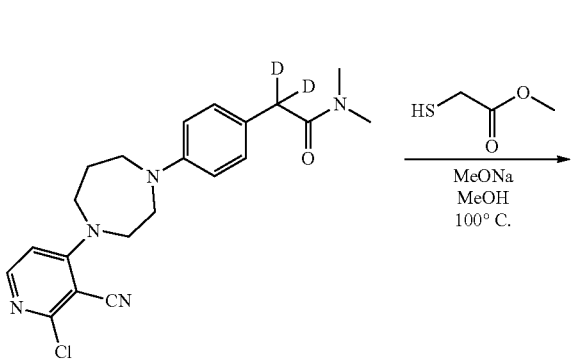
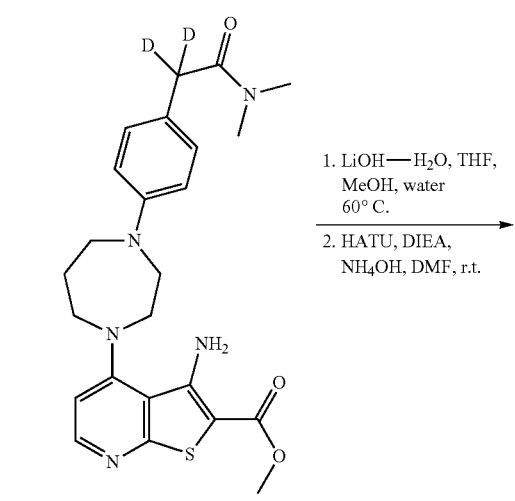
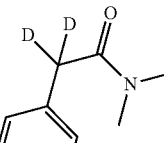
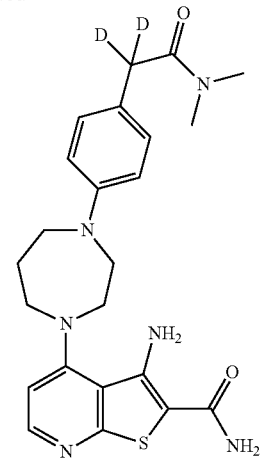 [SMILES: [2H]C([2H])(C(=O)N(C)C)c1ccc(N2CCCN(c3ccnc4sc(C(N)=O)c(N)c34)CC2)cc1]
For the experimental procedure see 15w above. ESI-MS m/z: 455 ([M+H]⁺).
Synthesis of 3-amino-4-(4-(4-(dimethylcarbamoyl)phenyl)-1,4-diazepan-1-yl)thieno[2,3-b]pyridine-2-carboxamide (15u)
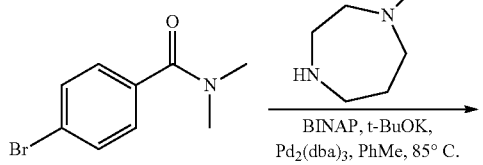
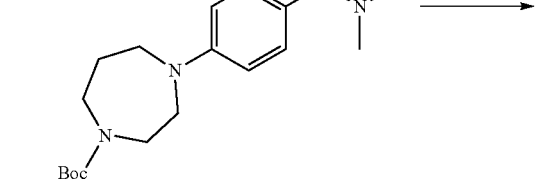
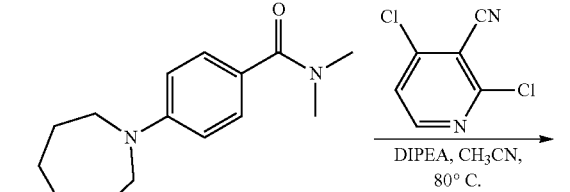
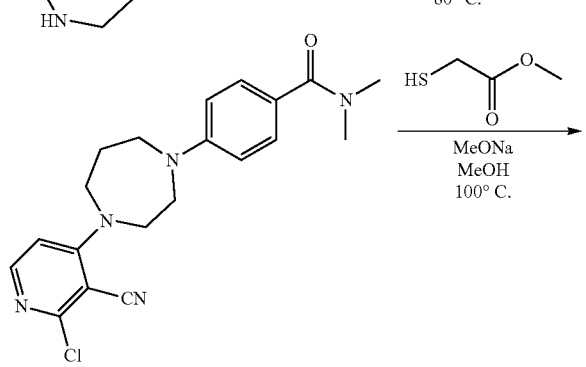

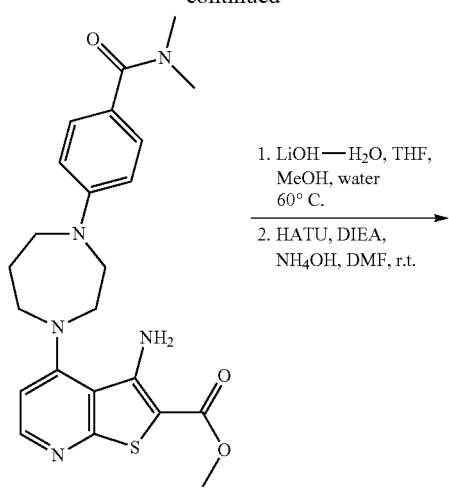
For the experimental procedure see 15w above. A light yellow solid was obtained. ESI-MS m/z: 439 ([M+H]⁺).
Synthesis of 3-amino-4-(4-(4-(bis(methyl-d3)carbamoyl)phenyl)-1,4-diazepan-1-yl)thieno[2,3-b]pyridine-2-carboxamide (15u_D6)
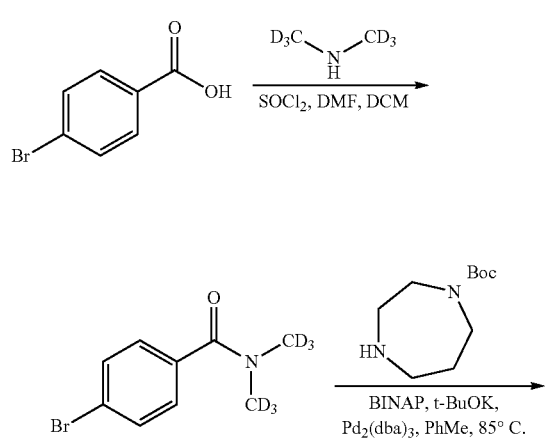
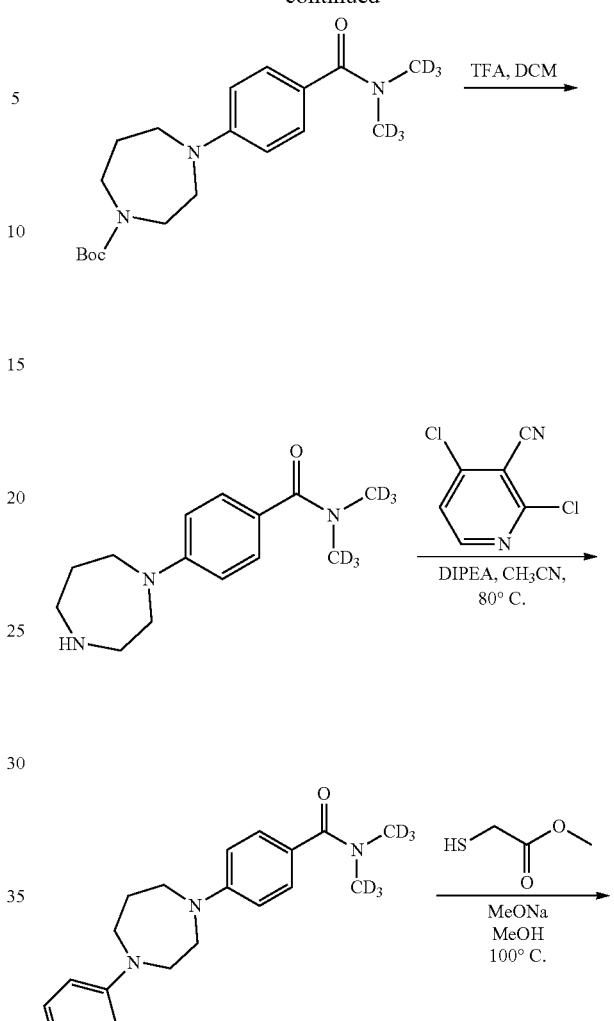
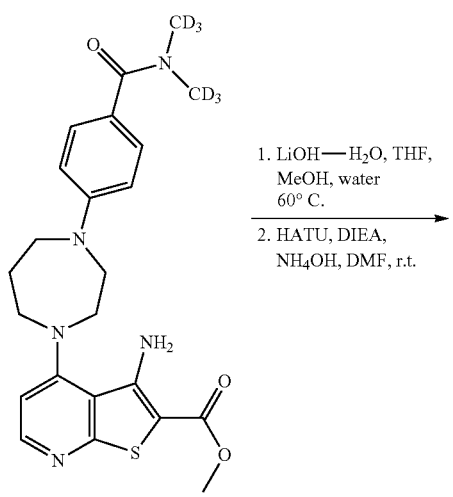

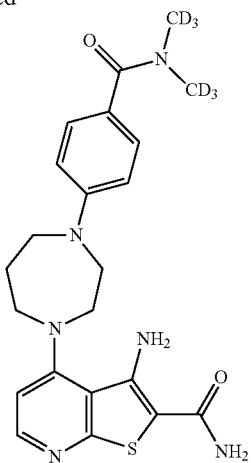

Figure 14A:
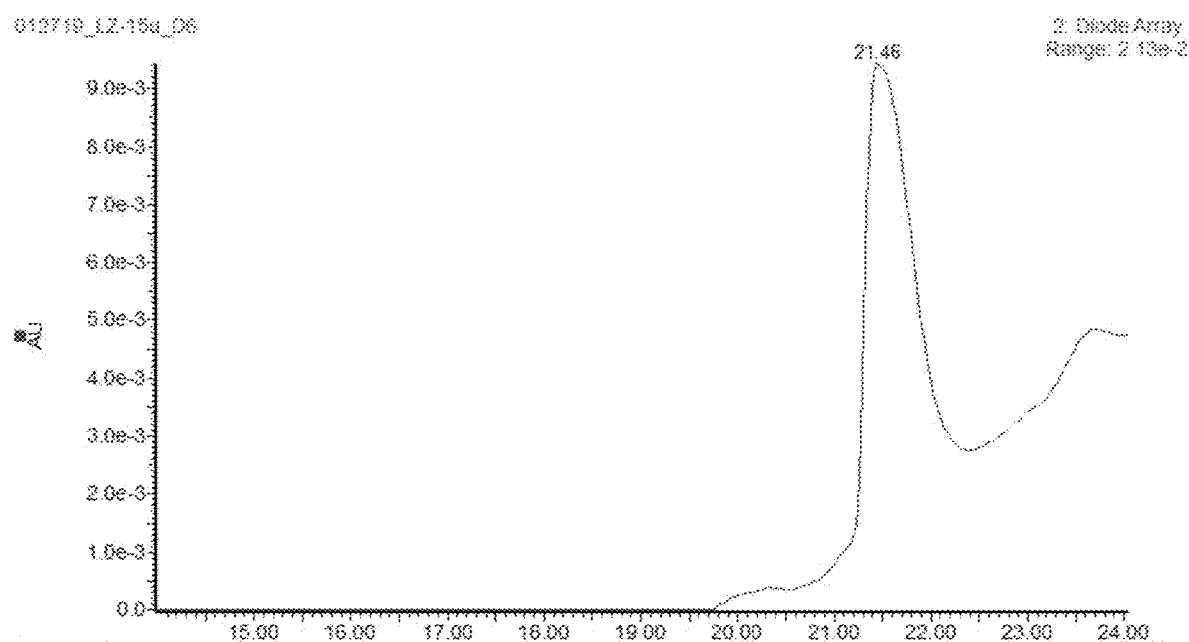
FIGS. 14A-14C confirm the synthesis of 15u_D6 via LCMS.
Figure 14B:
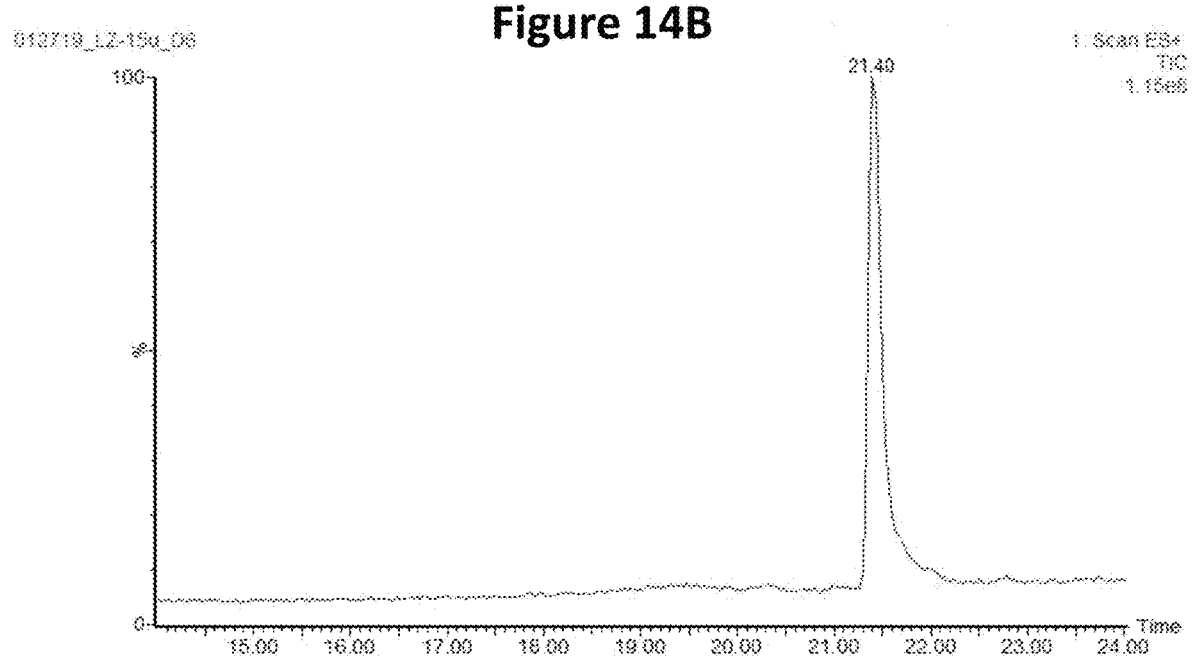
Figure 14C:
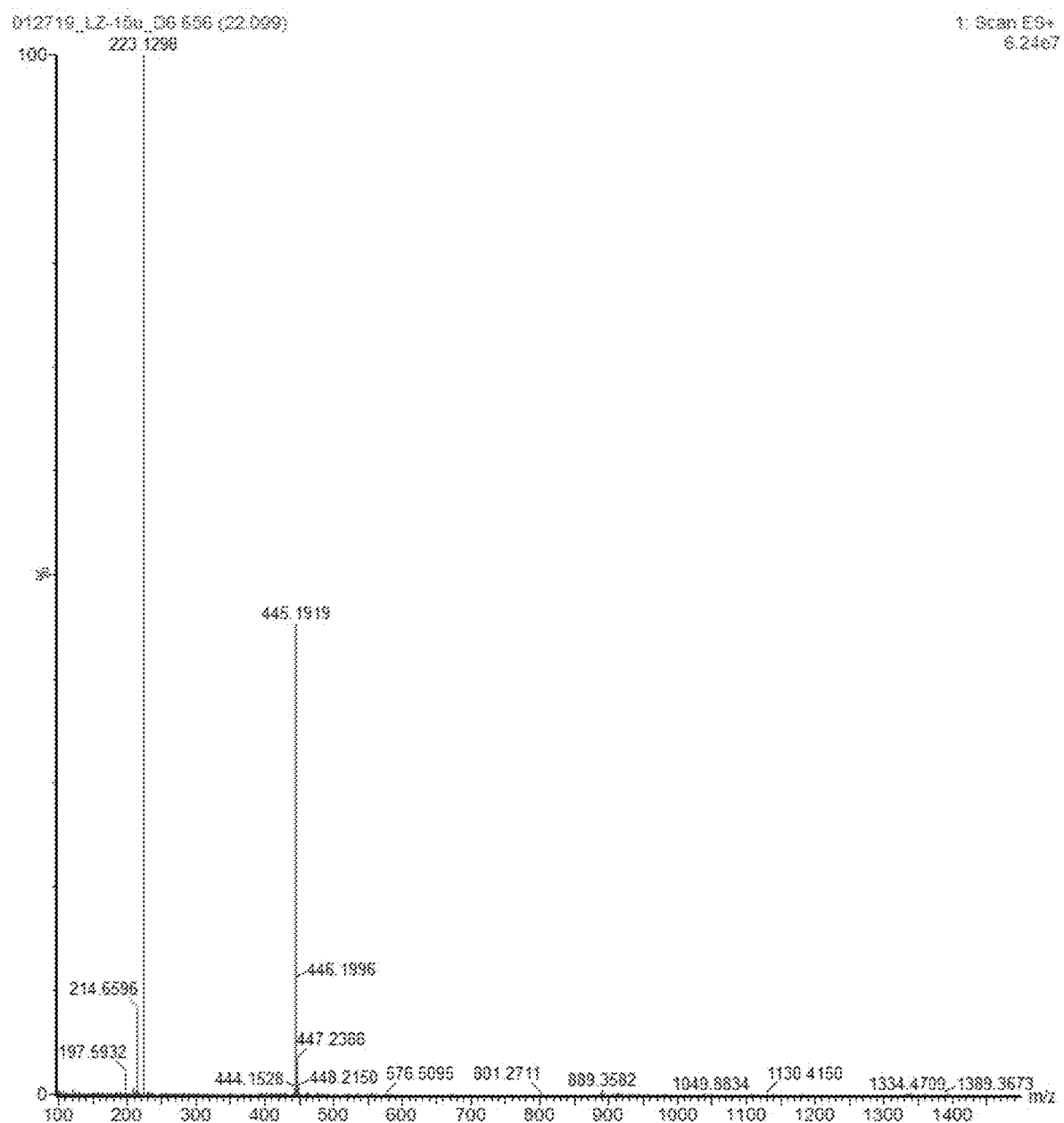

For the experimental procedure see 15w above. The synthesis of 15u_D6 was confirmed by analysis on a Waters HPLC-MS (LCA-232 SQ MS detector). Retention time was 21.40 minutes (5-95% TFA, 0.1% Formic acid) and the Parent Ion (M+1) observed at 445.1919. FIG. 14A shows a UV chromatograph of the 15u_D6 compound eluting at around 21 minutes. FIG. 14B shows an ESI chromatograph of compound 15u_D6 eluting at around 21 minutes. FIG. 14C confirms the synthesis of 15u_D6, ESI-MS m/z: 445 ([M+H]$^+$).

Synthesis of 3-amino-4-(4-(4-((4-methylpiperazin-1-yl)methyl)phenyl)-1,4-diazepan-1-yl)thieno[2,3-b]pyridine-2-carboxamide (6300)

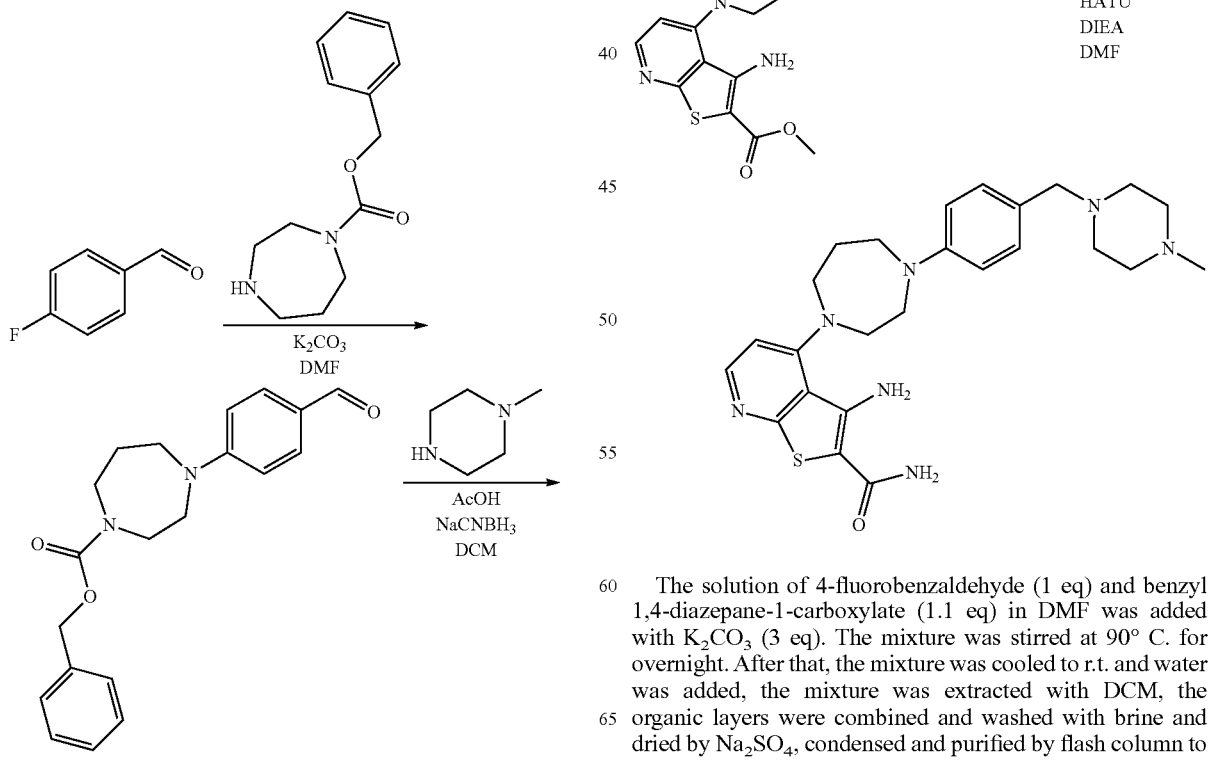

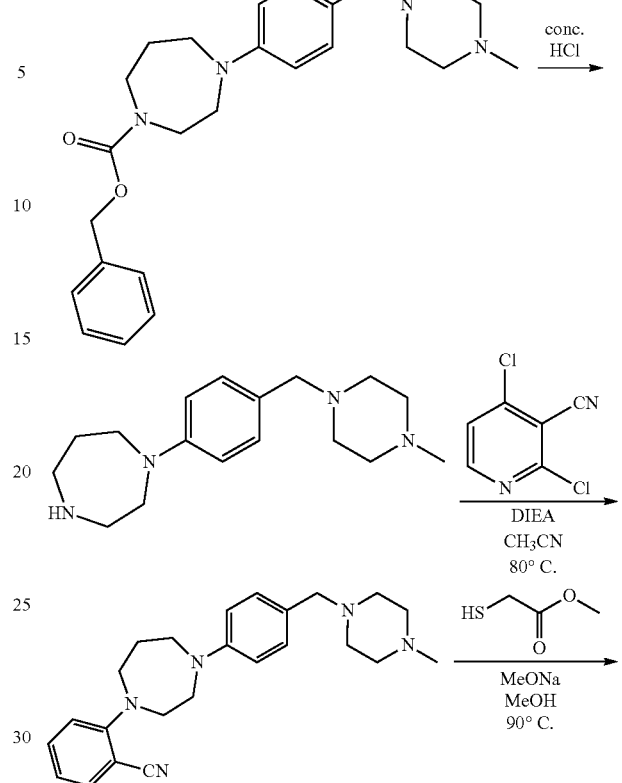

The solution of 4-fluorobenzaldehyde (1 eq) and benzyl 1,4-diazepane-1-carboxylate (1.1 eq) in DMF was added with K$_2$CO$_3$ (3 eq). The mixture was stirred at 90° C. for overnight. After that, the mixture was cooled to r.t. and water was added, the mixture was extracted with DCM, the organic layers were combined and washed with brine and dried by Na$_2$SO$_4$, condensed and purified by flash column to get the benzyl 4-(4-formylphenyl)-1,4-diazepane-1-carboxylate (yield 32%), ESI-MS m/z: 339 ([M+H]⁺); the solution of benzyl 4-(4-formylphenyl)-1,4-diazepane-1-carboxylate (1 eq) and 1-methylpiperazine (2 eq) in DCM, the solution was adjusted to pH 5 with acetic acid, then NaBH$_3$CN (1.5 eq) was added and the mixture was stirred at r.t. for overnight. After that, sat NaHCO$_3$ aq was added and the mixture was extracted with DCM, the organic layers were combined and washed with brine and dried by Na$_2$SO$_4$ and condensed and purified by flash column to get the benzyl 4-[4-[(4-methylpiperazin-1-yl)methyl]phenyl]-1,4-diazepane-1-carboxylate (yield 66%), ESI-MS m/z: 423 ([M+H]⁺); the solution of benzyl 4-[4-[(4-methylpiperazin-1-yl)methyl]phenyl]-1,4-diazepane-1-carboxylate (1 eq) was dissolved in concentrated HCl and stirred at r.t. for 2 h, then condensed and got the 1-(4-((4-methylpiperazin-1-yl)methyl)phenyl)-1,4-diazepane which is used without further purification, ESI-MS m/z: 289 ([M+H]⁺); the solution of 1-(4-((4-methylpiperazin-1-yl)methyl)phenyl)-1,4-diazepane (1 eq) in acetonitrile was added with 2,4-dichloronicotinonitrile (1 eq) and DIPEA (2 eq). Then the mixture was stirred at 80° C. for overnight. After that, the mixture was cooled to r.t. and condensed, the mixture was then dissolved in DCM and water was added, the mixture was extracted with DCM, the organic layers were collected and washed with brine and dried by Na$_2$SO$_4$, condensed and purified by flash column to get the 2-chloro-4-(4-(4-((4-methylpiperazin-1-yl)methyl)phenyl)-1,4-diazepan-1-yl)nicotinonitrile (yield 44%), ESI-MS m/z: 425 ([M+H]⁺); the solution of 2-chloro-4-(4-(4-((4-methylpiperazin-1-yl)methyl)phenyl)-1,4-diazepan-1-yl)nicotinonitrile (1 eq) in MeOH was added with MeONa (2 eq) and methyl thioglycolate (2 eq), then the mixture was stirred at 90° C. for overnight. After that, the mixture was cooled to r.t. and condensed and purified by flash column to get the methyl 3-amino-4-(4-(4-((4-methylpiperazin-1-yl)methyl)phenyl)-1,4-diazepan-1-yl)thieno[2,3-b]pyridine-2-carboxylate (yield 79%), ESI-MS m/z: 495 ([M+H]⁺); the solution of methyl 3-amino-4-(4-(4-((4-methylpiperazin-1-yl)methyl)phenyl)-1,4-diazepan-1-yl)thieno[2,3-b]pyridine-2-carboxylate (1 eq) in THF and water, then LiOH (2 eq) was added and the mixture was stirred at 60° C. for overnight. After that, the mixture was cooled to r.t. and condensed and dissolved in DMF, then HATU (1.5 eq) and DIPEA (2 eq) were added and the mixture was stirred at r.t. for 15 min, then NH$_4$OH (6 eq) was added to the above mixture and stirred at r.t. for another 2 h. After that, water was added and the mixture was extracted with DCM, the organic layers were combined and dried by Na$_2$SO$_4$, condensed and purified by flash column to get the 3-amino-4-(4-(4-((4-methylpiperazin-1-yl)methyl)phenyl)-1,4-diazepan-1-yl)thieno[2,3-b]pyridine-2-carboxamide (yield 30%). $^1$H NMR (300 MHz, DMSO-d6) δ: 8.39 (d, J=5.2 Hz, 1H), 7.08 (d, J=9.6 Hz, 3H), 7.07 (s, 2H), 6.97 (s, 2H), 6.71 (d, J=8.4 Hz, 2H), 3.75 (m, 2H), 3.52 (t, J=6.1 Hz, 2H), 3.32 (s, 2H), 3.29 (m, 2H), 2.33 (m, 8H), 2.16 (s, 3H), 2.13 (m, 2H); $^{13}$C NMR (300 MHz, DMSO-d6) δ: 167.07, 160.35, 159.35, 150.53, 147.59, 146.38, 130.06, 130.06, 124.87, 119.21, 111.74, 111.34, 111.34, 94.99, 61.68, 55.83, 54.76, 54.66, 54.66, 52.30, 52.30, 47.99, 47.99, 45.63, 27.39; ESI-MS m/z: 480 ([M+H]⁺).

Synthesis of 3-amino-4-(4-(4-(dimethylcarbamoyl)phenyl)-1,4-diazepan-1-yl)-6-methylthieno[2,3-b]pyridine-2-carboxamide (6304)

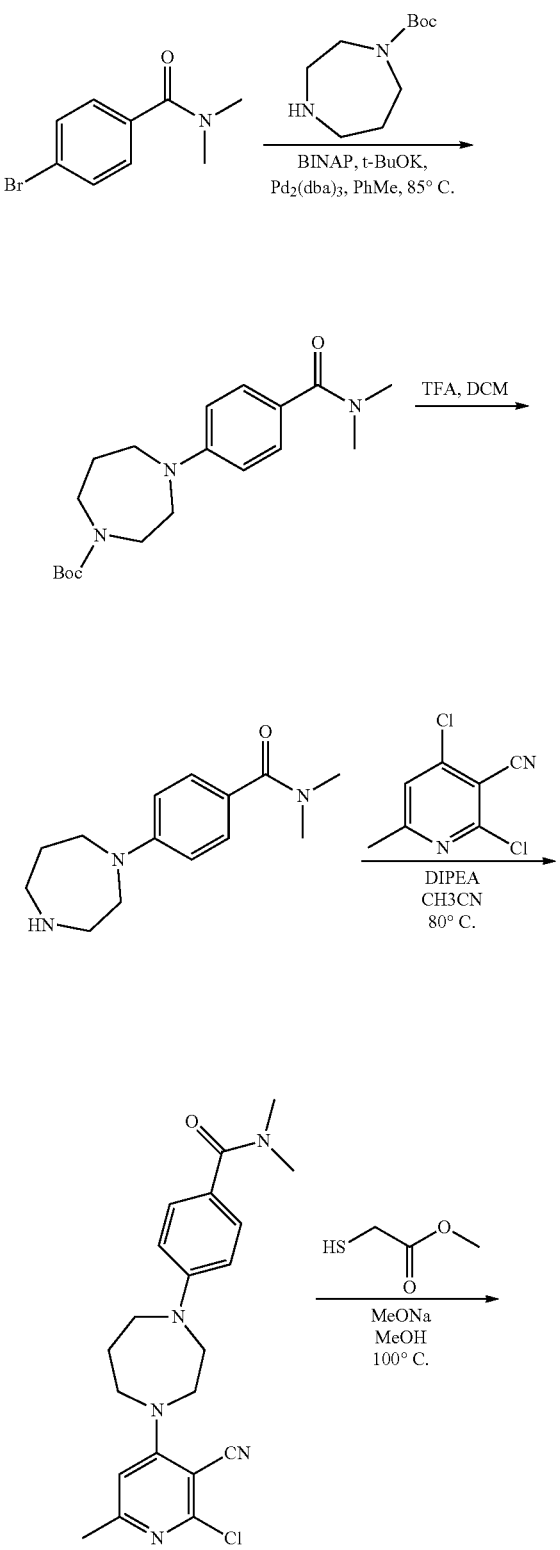

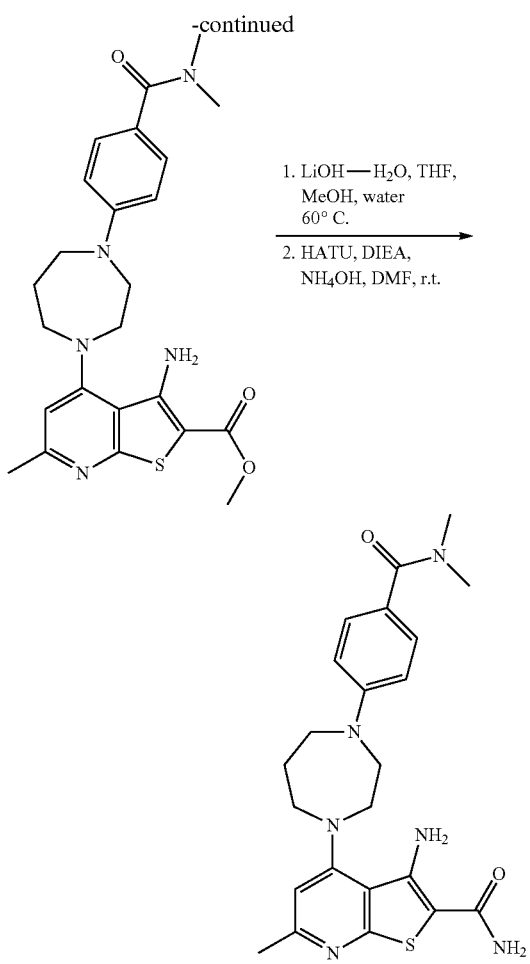

The solution of 4-bromo-N,N-dimethylbenzamide (1 eq) and tert-butyl 1,4-diazepane-1-carboxylate (1.2 eq) in t-BuOH and 1,4-dioxane was added with 2-Dicyclohexylphosphino-2'-(N,N-dimethylamino)biphenyl (0.15 eq), t-BuONa (1.4 eq) and Tris(dibenzylideneacetone)dipalladium (0.05 eq). The mixture was degassed and protected with nitrogen, then reflux for 1 h. After that, the mixture was cooled to r.t. and water was added, the mixture was extracted with EA, the organic layers were washed with brine and dried by $Na_2SO_4$, condensed and purified by flash column to get the tert-butyl 4-(4-(dimethylcarbamoyl)phenyl)-1,4-diazepane-1-carboxylate (yield 94%), ESI-MS m/z: 348 ([M+H]$^+$); the solution of tert-butyl 4-(4-(dimethylcarbamoyl)phenyl)-1,4-diazepane-1-carboxylate (1 eq) in DCM, then TFA (5 eq) was added and the mixture was stirred at r.t. for 3 h, after that, the mixture was condensed to remove the TFA and resulted the 4-(1,4-diazepan-1-yl)-N,N-dimethylbenzamide which was used without further purification, ESI-MS m/z: 248 ([M+H]$^+$); the solution of 4-(1,4-diazepan-1-yl)-N,N-dimethylbenzamide (1 eq) in acetonitrile was added with 2,4-dichloro-6-methylnicotinonitrile (1 eq) and DIPEA (2 eq). Then the mixture was stirred at 80° C. for overnight. After that, the mixture was cooled to r.t. and condensed, the mixture was then dissolved in DCM and water was added, the mixture was extracted with DCM, the organic layers were collected and washed with brine and dried by $Na_2SO_4$, condensed and purified by flash column to get the 4-(4-(2-chloro-3-cyano-6-methylpyridin-4-yl)-1,4-diazepan-1-yl)-N,N-dimethylbenzamide (yield 66%), ESI-MS m/z: 398 ([M+H]$^+$); the solution of 4-(4-(2-chloro-3-cyano-6-methylpyridin-4-yl)-1,4-diazepan-1-yl)-N,N-dimethylbenzamide (1 eq) in MeOH was added with MeONa (2 eq) and methyl thioglycolate (2 eq), then the mixture was stirred at 100° C. for overnight. After that, the mixture was cooled to r.t. and condensed and purified by flash column to get the methyl 3-amino-4-(4-(4-(dimethylcarbamoyl)phenyl)-1,4-diazepan-1-yl)-6-methylthieno[2,3-b]pyridine-2-carboxylate (yield 77%), ESI-MS m/z: 468 ([M+H]$^+$); the solution of methyl 3-amino-4-(4-(4-(dimethylcarbamoyl)phenyl)-1,4-diazepan-1-yl)-6-methylthieno[2,3-b]pyridine-2-carboxylate (1 eq) in THF and water, then LiOH (2 eq) was added and the mixture was stirred at 60° C. for overnight. After that, the mixture was cooled to r.t. and condensed and dissolved in DMF, then HATU (1.5 eq) and DIPEA (2 eq) were added and the mixture was stirred at r.t. for 15 min, then NH$_4$OH (6 eq) was added to the above mixture and stirred at r.t. for another 2 h. After that, water was added and the mixture was extracted with DCM, the organic layers were combined and dried by Na$_2$SO4, condensed and purified by flash column to get the 3-amino-4-(4-(4-(dimethylcarbamoyl)phenyl)-1,4-diazepan-1-yl)-6-methylthieno[2,3-b]pyridine-2-carboxamide (yield 33%) as a light yellow solid, $^1$H NMR (300 MHz, DMSO-d6) δ: 7.30 (d, J=8.9 Hz, 2H), 7.02 (s, 2H), 6.96 (s, 3H), 6.77 (d, J=8.9 Hz, 2H), 3.81 (m, 2H) 3.58 (m, 2H), 3.27 (m, 2H), 3.16 (m, 2H), 2.97 (s, 6H), 2.45 (s, 3H), 2.14 (m, 2H); $^{13}$C NMR (300 MHz, DMSO-d6) δ: 170.50, 167.18, 160.03, 159.94, 159.39, 149.42, 146.46, 129.35, 129.35, 122.56, 117.13, 111.78, 110.45, 110.45, 94.25, 55.52, 54.93, 47.88, 47.75, 39.52, 39.52, 27.23, 24.22; ESI-MS m/z: 453 ([M+H]$^+$).

Synthesis of 3-amino-4-(4-(4-((3-hydroxypropyl)(methyl)carbamoyl)phenyl)-1,4-diazepan-1-yl)thieno[2,3-b]pyridine-2-carboxamide (6264)

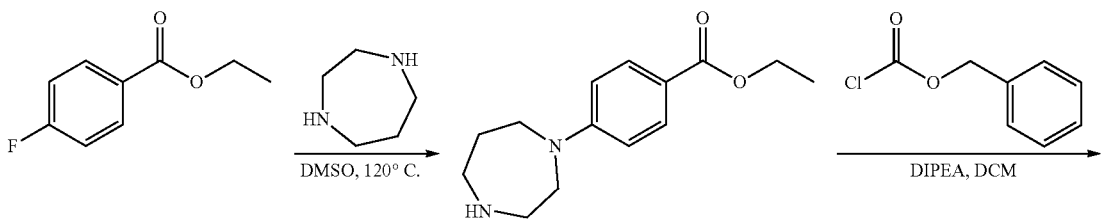

-continued
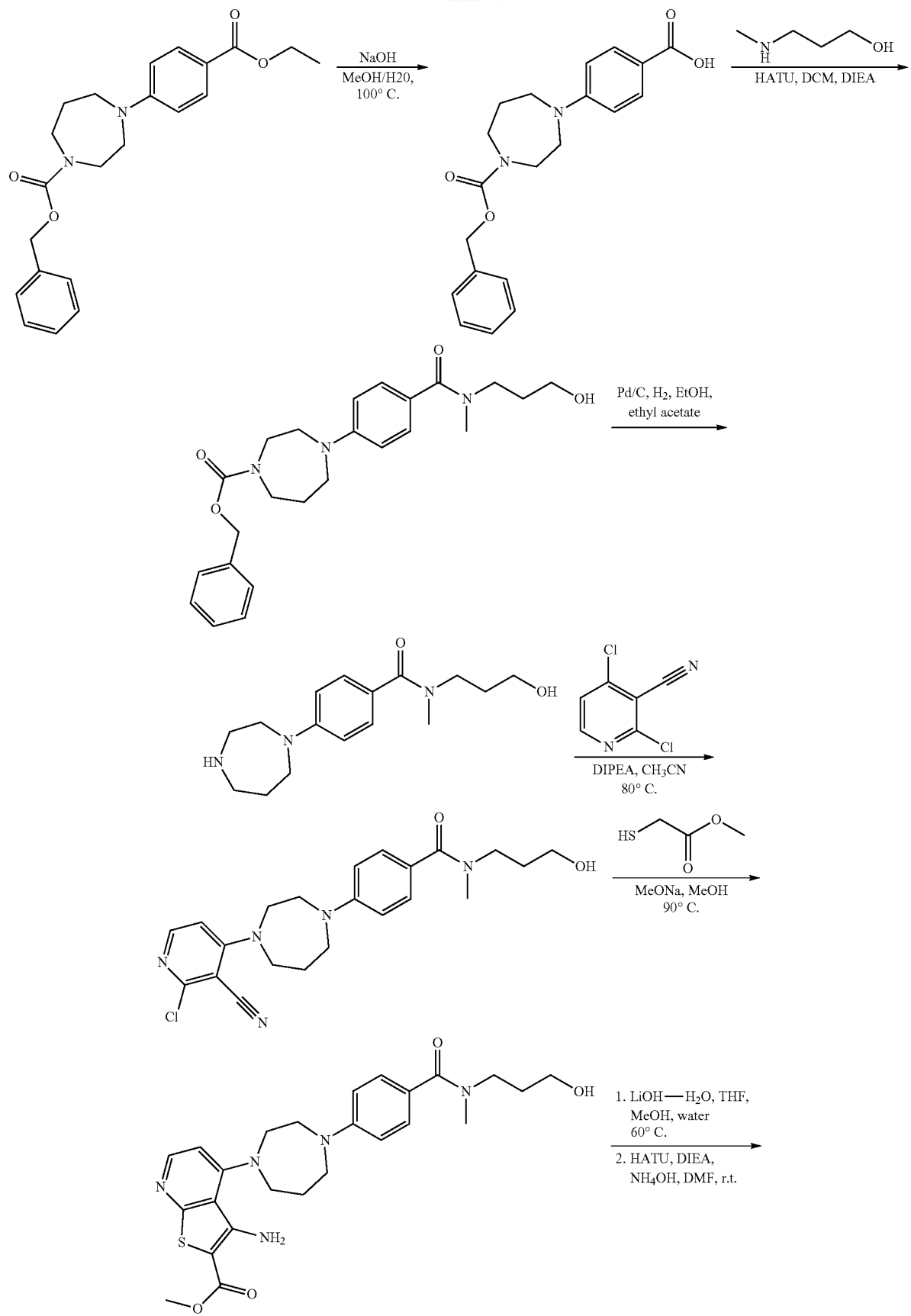

-continued

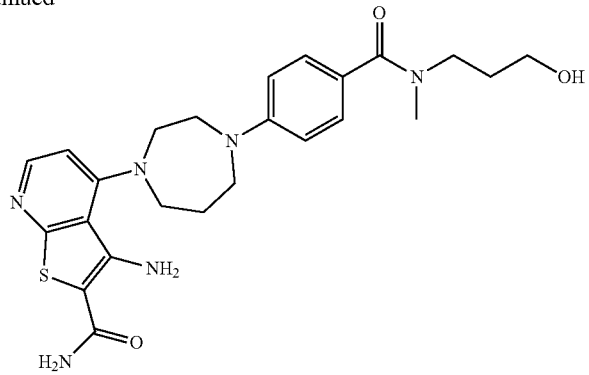

The solution of ethyl 4-fluorobenzoate (1 eq) and 1,4-diazepane (2 eq) in DMSO was added was stirred at 120° C. for overnight. After that, the mixture was cooled to r.t. and water was added, the mixture was extracted with DCM, the organic layers were combined and washed with brine and dried by Na$_2$SO$_4$, condensed and purified by flash column to get ethyl 4-(1,4-diazepan-1-yl)benzoatethe (yield 83%), ESI-MS m/z: 249 ([M+H]$^+$); the solution of ethyl 4-(1,4-diazepan-1-yl)benzoate (1 eq) and benzyl carbonochloridate (1.5 eq) in DCM was added with DIPEA (2 eq), the mixture was then stirred at r.t. for overnight. After that, sat NaHCO$_3$ aq was added and the mixture was extracted with DCM, the organic layers were combined and washed with brine and dried by Na$_2$SO$_4$ and condensed and purified by flash column to get the benzyl 4-(4-(ethoxycarbonyl)phenyl)-1,4-diazepane-1-carboxylate (yield 80%), ESI-MS m/z: 383 ([M+H]$^+$); the solution of benzyl 4-(4-(ethoxycarbonyl)phenyl)-1,4-diazepane-1-carboxylate (1 eq) was dissolved in MeOH and water, then NaOH (2.5 eq) was added and the mixture was refluxed for 2 h, the mixture was then cooled to r.t. and condensed, water was added and the mixture was acidified by 1N HCl to pH=4, and extracted with DCM for three times, the organic layers were combined and dried by Na2SO4 and condensed to get the 4-(4-((benzyloxy)carbonyl)-1,4-diazepan-1-yl)benzoic acid which was used without further purification, ESI-MS m/z: 355 ([M+H]$^+$); the solution of 4-(4-((benzyloxy)carbonyl)-1,4-diazepan-1-yl) benzoic acid in DCM was added with HATU (1.5 eq) and DIPEA (3 eq), then the mixture was stirred at r.t. for 20 min, after that, 3-(methylamino)propan-1-ol (1.5 eq) was added and the mixture was stirred at r.t. for another 4 h. After that, water was added and the mixture was extracted with DCM, the organic layers were combined and dried by Na$_2$SO$_4$, condensed and purified by flash column to get the benzyl 4-(4-((3-hydroxypropyl)(methyl)carbamoyl)phenyl)-1,4-diazepane-1-carboxylate (yield 85%), ESI-MS m/z: 426 ([M+H]$^+$); the solution of benzyl 4-(4-((3-hydroxypropyl)(methyl)carbamoyl)phenyl)-1,4-diazepane-1-carboxylate (1 eq) in EtOH and ethyl acetate was added with Pd/C and the solution was then saturated with hydrogen and stirred at r.t. for overnight. After that, the mixture was filtered and the residue was washed with methanol, the solution was collected and combined and condensed to get the 4-(1,4-diazepan-1-yl)-N-(3-hydroxypropyl)-N-methylbenzamide (yield 90%), ESI-MS m/z: 292 ([M+H]$^+$); the solution of 4-(1,4-diazepan-1-yl)-N-(3-hydroxypropyl)-N-methylbenzamide (1 eq) in acetonitrile was added with 2,4-dichloronicotinonitrile (1 eq) and DIPEA (2 eq). Then the mixture was stirred at 80° C. for overnight. After that, the mixture was cooled to r.t. and condensed, the mixture was then dissolved in DCM and water was added, the mixture was extracted with DCM, the organic layers were collected and washed with brine and dried by Na$_2$SO$_4$, condensed and purified by flash column to get the 4-(4-(2-chloro-3-cyanopyridin-4-yl)-1,4-diazepan-1-yl)-N-(3-hydroxypropyl)-N-methylbenzamide (yield 47%), ESI-MS m/z: 428 ([M+H]$^+$); the solution of 4-(4-(2-chloro-3-cyanopyridin-4-yl)-1,4-diazepan-1-yl)-N-(3-hydroxypropyl)-N-methylbenzamide (1 eq) in MeOH was added with MeONa (2 eq) and methyl thioglycolate (2 eq), then the mixture was stirred at 90° C. for overnight. After that, the mixture was cooled to r.t. and condensed and purified by flash column to get the methyl 3-amino-4-(4-(4-((3-hydroxypropyl)(methyl)carbamoyl)phenyl)-1,4-diazepan-1-yl)thieno[2,3-b]pyridine-2-carboxylate (yield 78%), ESI-MS m/z: 498 ([M+H]$^+$); the solution of methyl 3-amino-4-(4-(4-((3-hydroxypropyl)(methyl)carbamoyl) phenyl)-1,4-diazepan-1-yl)thieno[2,3-b]pyridine-2-carboxylate (1 eq) in THF and water, then LiOH (2 eq) was added and the mixture was stirred at 60° C. for overnight. After that, the mixture was cooled to r.t. and condensed and dissolved in DMF, then HATU (1.5 eq) and DIPEA (2 eq) were added and the mixture was stirred at r.t. for 15 min, then NH$_4$OH (6 eq) was added to the above mixture and stirred at r.t. for another 2 h. After that, water was added and the mixture was extracted with DCM, the organic layers were combined and dried by Na$_2$SO4, condensed and purified by flash column to get the 3-amino-4-(4-(4-((3-hydroxypropyl)(methyl)carbamoyl)phenyl)-1,4-diazepan-1-yl) thieno[2,3-b]pyridine-2-carboxamide (yield 51%) as yellow solid, $^1$H NMR (300 MHz, DMSO-d6) δ: 8.40 (d, J=5.6 Hz, 1H), 7.27 (d, J=8.7 Hz, 2H), 7.10 (s, 2H), 7.08 (d, J=5.6 Hz, 1H), 7.00 (s, 2H), 6.78 (d, J=8.7 Hz, 2H), 4.47 (t, J=5.4 Hz, 1H), 3.81 (m, 2H), 3.59 (t, J=6.5 Hz, 2H), 3.41 (m, 4H), 3.30 (m, 2H), 3.20 (m, 2H), 2.95 (s, 3H), 2.16 (m, 2H), 1.70 (m, 2H); $^{13}$C NMR (300 MHz, DMSO-d6) δ: 170.69, 167.08, 160.35, 159.23, 150.55, 149.36, 146.38, 129.03, 129.03, 123.02, 119.19, 111.70, 110.50, 110.50, 95.13, 58.36, 58.36, 55.72, 54.82, 47.82, 47.82, 39.53, 39.53, 27.21; ESI-MS m/z: 483 ([M+H]$^+$).

We claim:

1. A compound of Formula 1

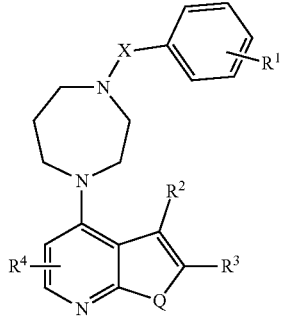

(Formula 1)

wherein Q is selected from sulfur, —NH—, or oxygen;

wherein X is selected from —(CH$_2$)$_n$— and n is selected from 0, 1, or 2;

wherein R$^4$ is hydrogen or a saturated or unsaturated, branched or unbranched, substituted or unsubstituted C$_1$-C$_6$ alkyl;

wherein R$^3$ is selected from hydrogen, cyano, a halo, a substituted or unsubstituted amino, a substituted or unsubstituted amido, or a substituted or unsubstituted sulfonamido;

wherein R$^2$ is selected from hydrogen, cyano, a halo, a substituted or unsubstituted amino, a substituted or unsubstituted amido or a substituted or unsubstituted sulfonamido; and wherein
(ii) when Q is sulfur, n is 0, R$^4$ is hydrogen, R$^3$ is —C(O)NH$_2$, and R$^2$ is —NH$_2$, R$^1$ is selected from a deuterated hydroxyl, a deuterated carboxy, a substituted or unsubstituted, deuterated amino; a substituted or unsubstituted, deuterated amido; a substituted or unsubstituted, deuterated or undeuterated sulfonamide, a saturated or unsaturated, branched or unbranched, substituted or unsubstituted, deuterated C$_1$-C$_6$ alkyl; a saturated or unsaturated, branched or unbranched, substituted or unsubstituted, deuterated C$_1$-C$_6$ alkoxyl; or (ii) when at least one of Q is not sulfur, n is not 0, R$^4$ is not hydrogen, R$^3$ is not —C(O)NH$_2$, and R$^2$ is nots —NH$_2$, R$^1$ is selected from a cyano; a deuterated or undeuterated hydroxyl, a deuterated or undeuterated carboxy, a halo, a substituted or unsubstituted, deuterated or undeuterated amino; a substituted or unsubstituted, deuterated or undeuterated amido; a substituted or unsubstituted, deuterated or undeuterated sulfonamide, a saturated or unsaturated, branched or unbranched, substituted or unsubstituted, deuterated or undeuterated C$_1$-C$_6$ alkyl; a saturated or unsaturated, branched or unbranched, substituted or unsubstituted, deuterated or undeuterated C$_1$-C$_6$ alkoxyl.

2. The compound of claim 1, wherein R$^1$ is

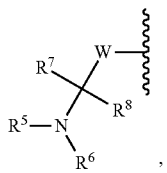

wherein W is selected from —(CH$_2$)$_m$— or —(CD$_2$)$_m$— and m is selected from 0, 1, or 2;

wherein R$^5$ and R$^6$ are independently selected from hydrogen, deuterium, a deuterated or undeuterated, saturated or unsaturated, branched or unbranched, substituted or unsubstituted C$_1$-C$_6$ alkyl; and wherein R$^7$ and R$^8$ are hydrogen, R$^7$ and R$^8$ are deuterium, or R$^7$ and R$^8$ together are oxo and wherein when Q is sulfur, n is 0, R$^4$ is hydrogen, R$^3$ is —C(O)NH$_2$, and R$^2$ is —NH$_2$, R$^1$ comprises a deuterium.

3. The compound of claim 2, wherein R$^1$ is N,N-bis(methyl-d3)formamide, N,N-bis(methyl-d3)acetamide, or N,N-dimethylacetamide-2,2-d2.

4. A compound of formula

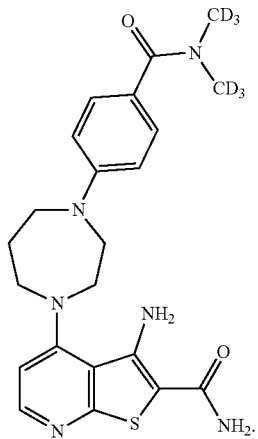 [SMILES: [2H]C([2H])([2H])N(C(=O)c1ccc(N2CCCN(c3ccnc4sc(C(N)=O)c(N)c34)CC2)cc1)C([2H])([2H])[2H]]

5. The compound of claim 1, wherein R$^1$ is

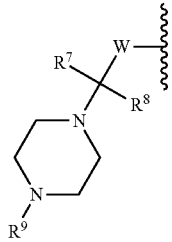

and wherein W is selected from —(CH$_2$)$_m$— or —(CD$_2$)$_m$— and m is selected from 0, 1, or 2;

wherein R$^9$ is selected from hydrogen, deuterium, or a deuterated or undeuterated, saturated or unsaturated, branched or unbranched, substituted or unsubstituted C$_1$-C$_6$ alkyl; wherein R$^7$ and R$^8$ are hydrogen, R$^7$ and R$^8$ are deuterium, or R$^7$ and R$^8$ together are oxo and, optionally, wherein the C$_4$N$_2$ heterocycle is deuterated.

6. A pharmaceutical composition comprising a therapeutically effective amount of the compound according to claim 1 and a pharmaceutically acceptable carrier, excipient, or diluent.

7. A method for treatment of a subject having a cancer, the method comprising administering a therapeutically effective amount of a compound of Formula 1

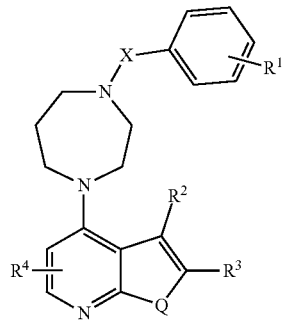
(Formula 1)

wherein Q is selected from sulfur, —NH—, or oxygen;
wherein X is selected from —(CH$_2$)$_n$— and n is selected from 0, 1, or 2;
wherein R$^4$ is hydrogen or a saturated or unsaturated, branched or unbranched, substituted or unsubstituted C$_1$-C$_6$ alkyl;
wherein R$^3$ is selected from hydrogen, cyano, a halo, a substituted or unsubstituted amino, a substituted or unsubstituted amido, or a substituted or unsubstituted sulfonamido;
wherein R$^2$ is selected from hydrogen, cyano, a halo, a substituted or unsubstituted amino, a substituted or unsubstituted amido or a substituted or unsubstituted sulfonamido; and
wherein R$^1$ is selected from hydrogen; a cyano; a deuterated or undeuterated hydroxyl, a deuterated or undeuterated carboxy, a halo, a substituted or unsubstituted, deuterated or undeuterated amino; a substituted or unsubstituted, deuterated or undeuterated amido; a substituted or unsubstituted, deuterated or undeuterated sulfonamide, a saturated or unsaturated, branched or unbranched, substituted or unsubstituted, deuterated or undeuterated C$_1$-C$_6$ alkyl; a saturated or unsaturated, branched or unbranched, substituted or unsubstituted, deuterated or undeuterated C$_1$-C$_6$ alkoxyl.

8. The method of claim 7, wherein the cancer is a prostate cancer, a leukemia, a breast cancer, colon cancer, ovarian cancer, pancreatic cancer, or melanoma.

9. The method of claim 8, wherein cancer is a prostate cancer.

10. The method of claim 9, wherein the prostate cancer is a castration refractory prostate cancer or is resistant to an androgen deprivation therapy.

11. The method of claim 9, wherein the subject has undergone the androgen deprivation therapy prior to administration of the compound to the subject or is undergoing the androgen deprivation therapy concurrently with administration of the compound to the subject.

12. The method of claim 8, wherein the cancer is a leukemia.

13. The method of claim 12, wherein the leukemia is acute myeloid leukemia.

14. The method of claim 8, wherein the cancer is a breast cancer.

15. The method of claim 14, wherein the breast cancer is metastatic breast cancer or a triple negative breast cancer.

16. The method of claim 7, wherein R$^1$ is

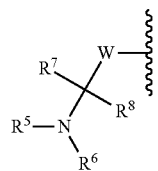

and wherein W is selected from —(CH$_2$)$_m$— or —(CD$_2$)$_m$— and m is selected from 0, 1, or 2;
wherein R$^5$ and R$^6$ are independently selected from hydrogen, deuterium, a deuterated or undeuterated, saturated or unsaturated, branched or unbranched, substituted or unsubstituted C$_1$-C$_6$ alkyl; and wherein R$^7$ and R$^8$ are hydrogen, R$^7$ and R$^8$ are deuterium, or R$^7$ and R$^8$ together are oxo.

17. The method of claim 16, wherein R$^1$ is N,N-bis(methyl-d3)formamide, N,N-bis(methyl-d3)acetamide, or N,N-dimethylacetamide-2,2-d2.

18. The method of claim 7, wherein the compound is

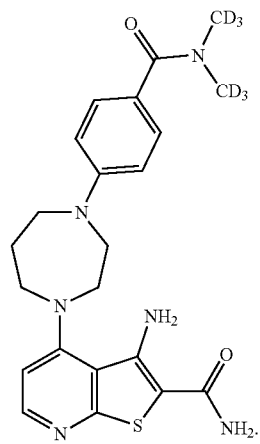 [SMILES: [2H]C([2H])([2H])N(C(=O)c1ccc(N2CCCN(c3ccnc4sc(C(N)=O)c(N)c34)CC2)cc1)C([2H])([2H])[2H]]

19. The method of claim 16, wherein R1 is N,N-dimethylformamide, N,N-dimethylacetamide, or N-methylformamide.

20. The method of claim 7, wherein the compound is

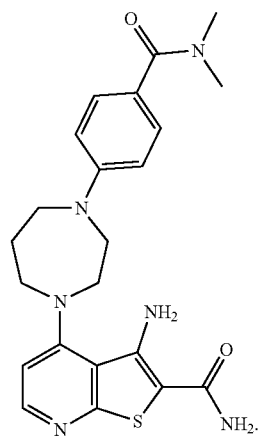 [SMILES: CN(C)C(=O)c1ccc(N2CCCN(c3ccnc4sc(C(N)=O)c(N)c34)CC2)cc1]

* * * * *